(12) United States Patent
Bossenmaier et al.

(10) Patent No.: US 7,429,605 B2
(45) Date of Patent: Sep. 30, 2008

(54) PHENYLPYRIDINE DERIVATIVES

(75) Inventors: Birgit Bossenmaier, Seefeld (DE); Thomas Friess, Diessen-Dettenhofen (DE); Rolf Juchem, Lampertheim (DE); Lothar Kling, Mannheim (DE); Irene Kolm, Wielheim (DE); Hans-Willi Krell, Penzberg (DE); Thomas von Hirschheydt, Penzberg (DE); Edgar Voss, Bichl (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 120 days.

(21) Appl. No.: 11/497,145

(22) Filed: Aug. 1, 2006

(65) Prior Publication Data

US 2007/0032530 A1    Feb. 8, 2007

(30) Foreign Application Priority Data

Aug. 4, 2005    (EP)    ................... 05016956

(51) Int. Cl.
*A61K 31/4439*    (2006.01)
*C07D 401/12*    (2006.01)

(52) U.S. Cl. .................... 514/340; 546/268.4
(58) Field of Classification Search ............. 546/268.4; 514/340
See application file for complete search history.

(56) References Cited

U.S. PATENT DOCUMENTS

| | | |
|---|---|---|
| 6,716,863 B2 | 4/2004 | Tasaka et al. |
| 6,743,924 B2 | 6/2004 | Ikemoto et al. |
| 6,984,653 B2 | 1/2006 | Tasaka et al. |
| 2004/0242659 A1 | 12/2004 | Tasaka et al. |

FOREIGN PATENT DOCUMENTS

| | | |
|---|---|---|
| EP | 284 174 | 9/1988 |
| WO | WO 98/03505 | 1/1998 |
| WO | WO 01/77107 | 10/2001 |
| WO | WO 03/031442 | 4/2003 |
| WO | WO 03/059907 | 7/2003 |
| WO | WO 03/068749 | 8/2003 |
| WO | WO 2004/007439 | 1/2004 |
| WO | WO 2004/085434 | 10/2004 |
| WO | WO 2005/049573 | 6/2005 |

OTHER PUBLICATIONS

Al-Saleh et al., J. Heterocyclic Chem., 39, pp. 1035-1038 (2002).

*Primary Examiner*—Patricia L Morris
(74) *Attorney, Agent, or Firm*—George W. Johnston; Patricia S. Rocha-Tramaloni; Gene J. Yao

(57) ABSTRACT

The present invention relates to the compounds of formula I:

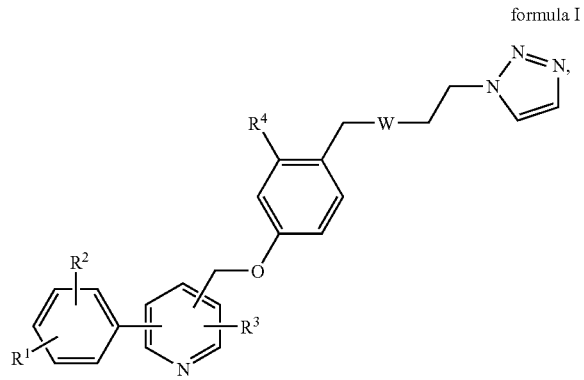

formula I their pharmaceutically acceptable salts, enantiomeric forms, diastereoisomers and racemates, the preparation of the above-mentioned compounds, pharmaceutical compositions containing such compounds and their manufacture, as well as the use of such compounds in the control or prevention of illnesses such as cancer.

38 Claims, No Drawings

PHENYLPYRIDINE DERIVATIVES

PRIORITY TO RELATED APPLICATIONS

This application claims the benefit of European Application No. 05016956.4, filed Aug. 4, 2005, which is hereby incorporated by reference in its entirety.

The present invention relates to novel phenylpyridine derivatives, to a process for their manufacture, pharmaceutical compositions containing them and their manufacture as well as the use of these compounds as pharmaceutically active agents.

BACKGROUND OF THE INVENTION

The treatment of cancer diseases is of great importance in medicine. There is a worldwide need for effective cancer therapies in order to achieve a treatment which is appropriate to a patient and is target-orientated. This can be seen in the large number of scientific studies which have recently appeared in the fields of applied oncology and fundamental research relating to cancer therapy. The effects of tumor inhibitors are due to a very wide variety of mechanisms, only some of which are known. It is not unusual for known tumor drugs to be found to have new mechanisms of action. This is also to be expected in the case of the compounds according to the invention. Many tumor drugs act by way of mechanisms such as blockading the mechanism of cell division in the cell, preventing the tumor from being supplied with nutrients and oxygen (antiangiogenesis), preventing metastasis, preventing the reception and the onward transmission of growth signals to the tumor cell or forcing the tumor cell into programmed cell death (apoptosis).

Because they have different mechanisms of action, including interacting with different intracellular targets, the clinically relevant cytostatic agents are frequently administered in combination in order to achieve a synergistic therapeutic effect.

WO 98/03505, WO 01/77107, WO 03/031442 and WO 03/059907 relate to heterocyclic compounds as tyrosine kinase inhibitors which are useful as anticancer agents.

SUMMARY OF THE INVENTION

The present invention relates to compounds of the general formula I and all pharmaceutically acceptable salts thereof wherein formula I is:

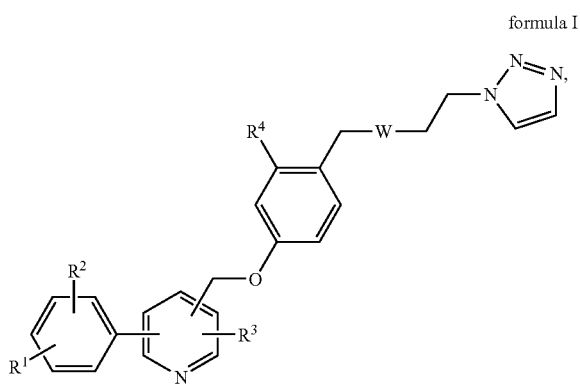

formula I wherein:
(a) $R^1$ is halogen) alkyl, alkoxy, halogenated alkyl or halogenated alkoxy;
(b) $R^2$ is hydrogen or halogen;
(c) $R^3$ is hydrogen or $(C_1-C_3)$alkyl;
(d) $R^4$ is hydrogen or $(C_1-C_3)$alkyl; and
(e) W is —$CH_2$—, —O—, —S—, —S(O)— or —$S(O)_2$—.

The compounds of the present invention show anti-proliferative activity. The present invention provides compounds of formula I and their pharmaceutically acceptable salts, enantiomeric forms, diastereoisomers and racemates; the preparation or manufacture of the above-mentioned compounds; pharmaceutical compositions containing such compounds and their manufacture; as well as the use of the above-mentioned compounds in the control or prevention of illnesses, disorders, diseases, and/or conditions such as common human cancers such as breast cancer, gastrointestinal cancer (i.e., colon cancer, rectal cancer or stomach cancer), leukemia, ovarian cancer, bronchial cancer, or pancreatic cancer.

DETAILED DESCRIPTION OF THE INVENTION

The term "alkyl" as used herein means a saturated, straight-chain or branched-chain hydrocarbon containing from 1 to 6 carbon atoms, preferably 1 to 4 carbon atoms, such as methyl, ethyl, n-propyl, isopropyl, n-butyl, 2-butyl, t-butyl, n-pentyl, 3-methyl-butyl, 2-methyl-butyl, n-hexyl, 3-methyl-pentyl, 2-ethyl-butyl, 3,3-dimethyl-butyl, 2,2-dimethyl-butyl or 2,3-dimethyl-butyl.

The term "alkoxy" as used herein means an alkyl-O-group wherein the alkyl is defined as above.

The term "halogenated alkyl" as used herein means an alkyl group as defined above which is substituted one to five times, preferably one to three times, by halogen, preferably by fluorine or chlorine, and more preferably by fluorine. Examples are difluoromethyl, trifluoromethyl, 2,2,2-trifluoroethyl, perfluoroethyl, and the like, preferably trifluoromethyl.

The term "halogenated alkoxy" as used herein means an alkoxy group as defined above which is substituted one to five times, preferably one to three times, by halogen, preferably by fluorine or chlorine, and more preferably by fluorine. Examples are difluoromethoxy, trifluoromethoxy, 2,2,2-trifluoroethoxy, perfluoroethoxy and the like, preferably trifluoromethoxy.

The term "halogen" as used herein means fluorine, chlorine, or bromine, preferably fluorine or chlorine.

A preferred position of the substituent $R^1$ on the phenyl ring in formulas I, Ia and Ie is para relative to the direct bond between the phenyl and the pyridyl ring of formulas I, Ia and Ie.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

As used herein, in relation to mass spectrometry (MS) the term "ESI+" refers to positive electrospray ionization mode.

An embodiment are the compounds according to formula I, wherein
$R^2$ is hydrogen.

Another embodiment are the compounds according to formula I, wherein
$R^1$ is halogen, halogenated alkyl or halogenated alkoxy.

Another embodiment are the compounds according to formula I, wherein
W is —$CH_2$—.

Another embodiment are the compounds according to formula I, wherein
$R^2$ is hydrogen and
W is —$CH_2$—.

Another embodiment are the compounds according to formula I, wherein
W is —O—.

Another embodiment are the compounds according to formula I, wherein
$R^2$ is hydrogen and W is —O—.

Another embodiment are the compounds according to formula I, wherein
W is —S(O)—.

Another embodiment are the compounds according to formula I, wherein
$R^2$ is hydrogen and
W is —S(O)—.

Another embodiment are the compounds according to formula I, wherein
$R^4$ is hydrogen.

Another embodiment are the compounds according to formula I, wherein
$R^2$ and $R^4$ are both hydrogen.

Another embodiment are the compounds according to formula I, wherein
$R^4$ is hydrogen and
W is —$CH_2$—.

Another embodiment are the compounds according to formula I, wherein
$R^2$ and $R^4$ are both hydrogen and
W is —$CH_2$—.

Another embodiment are the compounds according to formula I, wherein
$R^4$ is hydrogen and
W is —O—.

Another embodiment are the compounds according to formula I, wherein
$R^2$ and $R^4$ are both hydrogen and
W is —O—.

Another embodiment are the compounds according to formula I, wherein
$R^4$ is hydrogen and
W is —S(O)—.

Another embodiment are the compounds according to formula I, wherein
$R^2$ and $R^4$ are both hydrogen and
W is —S(O)—.

Another embodiment are the compounds according to formula I, wherein
$R^4$ is ($C_1$-$C_3$)alkyl.

Another embodiment are the compounds according to formula I, wherein
$R^2$ is hydrogen and
$R^4$ is ($C_1$-$C_3$)alkyl.

Another embodiment are the compounds according to formula I, wherein
$R^4$ is ($C_1$-$C_3$)alkyl and
W is —$CH_2$—.

Another embodiment are the compounds according to formula I, wherein:
(a) $R^2$ is hydrogen;
(b) $R^4$ is ($C_1$-$C_3$)alkyl; and
(c) W is —$CH_2$—.

Another embodiment are the compounds according to formula I, wherein
$R^4$ is ($C_1$-$C_3$)alkyl and
W is —O—.

Another embodiment are the compounds according to formula I, wherein:
(a) $R^2$ is hydrogen;
(b) $R^4$ is ($C_1$-$C_3$)alkyl; and
(c) W is —O—.

Another embodiment are the compounds according to formula I, wherein
$R^4$ is ($C_1$-$C_3$)alkyl and
W is —S(O)—.

Another embodiment are the compounds according to formula I, wherein:
(a) $R^2$ is hydrogen;
(b) $R^4$ is ($C_1$-$C_3$)alkyl; and
(c) W is —S(O)—.

Another embodiment are the compounds according to formula I, wherein:
(a) $R^2$ is hydrogen; and
(b) W is —$CH_2$—, —O—, —S— or —S(O)—.

Another embodiment are the compounds according to formula I, wherein:
(a) $R^1$ is halogen, halogenated alkyl or halogenated alkoxy; and
(b) W is —$CH_2$—, —O—, —S— or —S(O)—.

Another embodiment of the present invention are the compounds according to formula I-a and all pharmaceutically acceptable salts thereof, wherein formula I-a is:

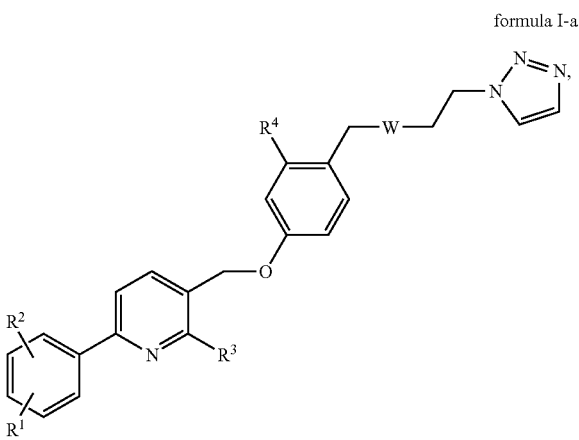

formula I-a wherein:
(a) $R^1$ is halogen, alkyl, alkoxy, halogenated alkyl or halogenated alkoxy;
(b) $R^2$ is hydrogen or halogen;
(c) $R^3$ is hydrogen or $(C_1$-$C_3)$alkyl;
(d) $R^4$ is hydrogen or $(C_1$-$C_3)$alkyl; and
(e) W is —$CH_2$—, —O—, —S—, —S(O)— or —S(O)$_2$—.

Another embodiment are the compounds according to formula I-a, wherein $R^1$ is halogen, halogenated alkyl or halogenated alkoxy.

Another embodiment are the compounds according to formula I-a, wherein
$R^2$ is hydrogen and
W is —$CH_2$—, —O— or —S(O)—.

Another embodiment are the compounds according to formula I-a, wherein
$R^2$ is hydrogen; and
W is —$CH_2$—, —O—, —S— or —S(O)—.

Another embodiment are the compounds according to formula I-a, wherein:
(a) $R^1$ is halogen, halogenated alkyl or halogenated alkoxy; and
(b) W is —$CH_2$—, —O—, —S— or —S(O)—.

Another embodiment are the compounds according to formula I-a, wherein:
(a) $R^1$ is halogen, halogenated alkyl or halogenated alkoxy;
(b) $R^2$ is hydrogen; and
(c) W is —$CH_2$—.

Another embodiment are the compounds according to formula I-a, wherein:
(a) $R^1$ is halogen;
(b) $R^2$ is hydrogen; and
(c) W is —$CH_2$—.

Such compounds, for example, may be selected from the group consisting of:
(a) 6-(4-Fluoro-phenyl)-2-methyl-3-[4-(4-[1,2,3]triazol-1-yl-butyl)-phenoxymethyl]-pyridine;
(b) 6-(4-Fluoro-phenyl)-2-methyl-3-[3-methyl-4-(4-[1,2,3]triazol-1-yl-butyl)-phenoxymethyl]-pyridine;
(c) 6-(4-Chloro-phenyl)-2-methyl-3-[4-(4-[1,2,3]triazol-1-yl-butyl)-phenoxymethyl]-pyridine;
(d) 6-(4-Chloro-phenyl)-2-methyl-3-[3-methyl-4-(4-[1,2,3]triazol-1-yl-butyl)-phenoxymethyl]-pyridine;
(e) 2-(4-Chloro-phenyl)-5-[4-(4-[1,2,3]triazol-1-yl-butyl)-phenoxymethyl]-pyridine; and
(f) 2-(4-Chloro-phenyl)-5-[3-methyl-4-(4-[1,2,3]triazol-1-yl-butyl)-phenoxymethyl]-pyridine.

Another embodiment are the compounds according to formula I-a, wherein:
(a) $R^1$ is halogenated alkyl;
(b) $R^2$ is hydrogen; and
(c) W is —$CH_2$—.

Such compounds, for example, may be selected from the group consisting of:
(a) 5-[4-(4-[1,2,3]Triazol-1-yl-butyl)-phenoxymethyl]-2-(4-trifluoromethyl-phenyl)-pyridine;
(b) 5-[3-Methyl-4-(4-[1, 2,3]triazol-1-yl-butyl)-phenoxymethyl]-2-(4-trifluoromethyl-phenyl)-pyridine;
(c) 2-Methyl-3-[3-methyl-4-(4-[1,2,3]triazol-1-yl-butyl)-phenoxymethyl]-6-(4-trifluoromethyl-phenyl)-pyridine;
(d) 2-Methyl-3-[4-(4-[1,2,3]triazol-1-yl-butyl)-phenoxymethyl]-6-(4-trifluoromethyl-phenyl)-pyridine;
(e) 2-Methyl-3-[4-(4-[1,2,3]triazol-1-yl-butyl)-phenoxymethyl]-6-(3-trifluoromethyl-phenyl)-pyridine;
(f) 2-Methyl-3-[2-methyl-4-(4-[1,2,3]triazol-1-yl-butyl)-phenoxymethyl]-6-(3-trifluoromethyl-phenyl)-pyridine;
(g) 5-[4-(4-[1,2,3]Triazol-1-yl-butyl)-phenoxymethyl]-2-(3-trifluoromethyl-phenyl)-pyridine; and
(h) 5-[3-Methyl-4-(4-[1,2,3]triazol-1-yl-butyl)-phenoxymethyl]-2-(3-trifluoromethyl-phenyl)-pyridine.

Another embodiment are the compounds according to formula I-a, wherein:
(a) $R^1$ is halogenated alkoxy;
(b) $R^2$ is hydrogen; and
(c) W is —$CH_2$—.

Such compounds, for example, may be selected from the group consisting of:
(a) 5-[3-Methyl-4-(4-[1,2,3]triazol-1-yl-butyl)-phenoxymethyl]-2-(4-trifluoromethoxy-phenyl)-pyridine;
(b) 2-Methyl-3-[4-(4-[1,2,3]triazol-1-yl-butyl)-phenoxymethyl]-6-(4-trifluoromethoxy-phenyl)-pyridine;
(c) 2-Methyl-3-[3-methyl-4-(4-[1,2,3]triazol-1-yl-butyl)-phenoxymethyl]-6-(4-trifluoromethoxy-phenyl)-pyridine;
(d) 2-Methyl-3-[4-(4-[1,2,3]triazol-1-yl-butyl)-phenoxymethyl]-6-(3-trifluoromethoxy-phenyl)-pyridine; and
(e) 2-Methyl-3-[2-methyl-4-(4-[1,2,3]triazol-1-yl-butyl)-phenoxymethyl]-6-(3-trifluoromethoxy-phenyl)-pyridine.

Another embodiment are the compounds according to formula I-a, wherein:
(a) $R^1$ is halogenated alkyl;
(b) $R^2$ is fluorine; and
(c) W is —$CH_2$—.

Such compounds, for example, may be selected from the group consisting of:
6-(2-Fluoro-4-trifluoromethyl-phenyl)-2-methyl-3-[3-methyl-4-(4-[1,2,3]triazol-1-yl-butyl)-phenoxymethyl]-pyridine; and
6-(2-Fluoro-4-trifluoromethyl-phenyl)-2-methyl-3-[4-(4-[1,2,3]triazol-1-yl-butyl)-phenoxymethyl]-pyridine.

Another embodiment are the compounds according to formula I-a, wherein:
(a) $R^2$ is hydrogen;
(b) $R^3$ is $(C_1$-$C_3)$alkyl; and
(c) W is —$CH_2$—.

Another embodiment are the compounds according to formula I-a, wherein $R^2$ and $R^3$ are both hydrogen and W is —$CH_2$—.

Another embodiment are the compounds according to formula I-a, wherein W is —O—.

Such a compound is for example:
2-Methyl-3-[4-(2-[1,2,3]triazol-1-yl-ethoxymethyl)-phenoxymethyl]-6-(4-trifluoromethyl-phenyl)-pyridine.

Another embodiment are the compounds according to formula I-a, wherein W is —S(O)—.

Such a compound is for example:

2-Methyl-3-[4-(2-[1,2,3]triazol-1-yl-ethanesulfinylmethyl)-phenoxymethyl]-6-(4-trifluoromethyl-phenyl)-pyridine.

Another embodiment are the compounds according to formula I-a, wherein W is —S—.

Another embodiment are the compounds according to formula I-a, wherein:
(a) $R^1$ is halogen or halogenated alkyl;
(b) $R^2$ is hydrogen; and
(c) W is —S—.

Such compounds, for example, may be selected from the group consisting of:
(a) 2-Methyl-3-[4-(2-[1,2,3]triazol-1-yl-ethylsulfanylmethyl)-phenoxymethyl]-6-(4-trifluoromethyl-phenyl)-pyridine;
(b) 6-(4-Fluoro-phenyl)-2-methyl-3-[4-(2-[1,2,3]triazol-1-yl-ethylsulfanylmethyl)-phenoxymethyl]-pyridine;
(c) 6-(4-Chloro-phenyl)-2-methyl-3-[4-(2-[1,2,3]triazol-1-yl-ethylsulfanylmethyl)-phenoxymethyl]-pyridine; and
(d) 2-(4-Chloro-phenyl)-5-[4-(2-[1,2,3]triazol-1-yl-ethylsulfanylmethyl)-phenoxymethyl]-pyridine.

Another embodiment are the compounds according to formula I-a, wherein W is —S(O)$_2$—.

Such a compound is for example:

2-Methyl-3-[4-(2-[1,2,3]triazol-1-yl-ethanesulfonylmethyl)-phenoxymethyl]-6-(4-trifluoromethyl-phenyl)-pyridine.

Another embodiment are the compounds according to formula I-a, wherein:
(a) $R^2$ is hydrogen;
(b) $R^4$ is $(C_1-C_3)$alkyl; and
(c) W is —CH$_2$—.

Another embodiment are the compounds according to formula I-a, wherein:
(a) $R^1$ is halogen, halogenated alkyl or halogenated alkoxy;
(b) $R^2$ is hydrogen;
(c) $R^4$ is $(C_1-C_3)$alkyl; and
(d) W is —CH$_2$—.

Another embodiment are the compounds according to formula I-a, wherein:
(a) $R^1$ is halogen, halogenated alkyl or halogenated alkoxy, which is attached at the para position relative to the direct bond between the phenyl and the pyridyl ring of formula I-a;
(b) $R^2$ is hydrogen;
(c) $R^4$ is $(C_1-C_3)$alkyl; and
(d) W is —CH$_2$—.

Another embodiment are the compounds according to formula I-a, wherein:
(a) $R^1$ is chlorine or halogenated alkyl, which is attached at the para position relative to the direct bond between the phenyl and the pyridyl ring of formula I-a;
(b) $R^2$ is hydrogen; and
(c) W is —CH$_2$—, —O— or —S—.

Another embodiment are the compounds according to formula I-a, wherein:
(a) $R^1$ is chlorine or halogenated alkyl, which is attached at the para position relative to the direct bond between the phenyl and the pyridyl ring of formula I-a;
(b) $R^2$ is hydrogen; and
(c) W is —CH$_2$—.

Another embodiment are the compounds according to formula I-a, wherein:
(a) $R^1$ is chlorine or halogenated alkyl, which is attached at the para position relative to the direct bond between the phenyl and the pyridyl ring of formula I-a;
(b) $R^2$ is hydrogen;
(c) $R^4$ is $(C_1-C_3)$alkyl; and
(d) W is —CH$_2$—.

Another embodiment are the compounds according to formula I-a, wherein:
(a) $R^1$ is chlorine which is attached at the para position relative to the direct bond between the phenyl and the pyridyl ring of formula I-a;
(b) $R^2$ is hydrogen; and
(c) W is —CH$_2$—.

Another embodiment are the compounds according to formula I-a, wherein:
(a) $R^1$ is halogenated alkyl, which is attached at the para position relative to the direct bond between the phenyl and the pyridyl ring of formula I-a;
(b) $R^2$ is hydrogen; and
(c) W is —CH$_2$—.

Another embodiment are the compounds according to formula I-b and all pharmaceutically acceptable salts thereof, wherein formula I-b is:

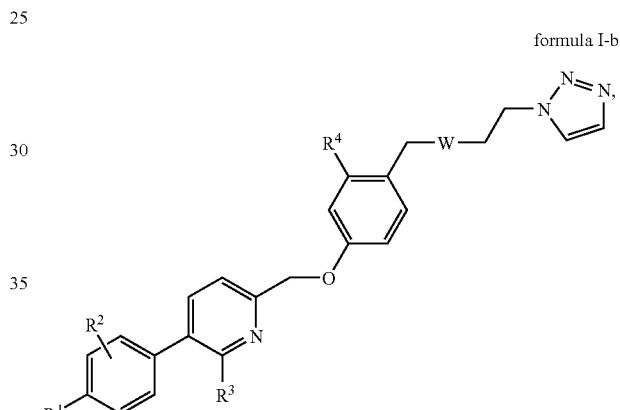

formula I-b wherein:
(a) $R^1$ is halogen, alkyl, alkoxy, halogenated alkyl or halogenated alkoxy;
(b) $R^2$ is hydrogen or halogen;
(c) $R^3$ is hydrogen or $(C_1-C_3)$alkyl;
(d) $R^4$ is hydrogen or $(C_1-C_3)$alkyl; and
(e) W is —CH$_2$—, —O—, —S—, —S(O)— or —S(O)$_2$—.

Another embodiment are the compounds according to formula I-b, wherein:
(a) $R^2$ is hydrogen; and
(b) W is —CH$_2$—, —O— or —S(O)—.

Another embodiment are the compounds according to formula I-b, wherein
$R^2$ is hydrogen and
W is —CH$_2$—.

Another embodiment are the compounds according to formula I-b, wherein:
(a) $R^1$ is halogenated alkyl;
(b) $R^2$ is hydrogen; and
(c) W is —CH$_2$—.

Such compounds, for example, may be selected from the group consisting of:
(a) 2-[4-(4-[1,2,3]Triazol-1-yl-butyl)-phenoxymethyl]-5-(4-trifluoromethyl-phenyl)-pyridine; and (b) 2-[3-Methyl-4-(4-[1,2,3]triazol-1-yl-butyl)-phenoxymethyl]-5-(4-trifluoromethyl-phenyl)-pyridine.

Another embodiment are the compounds according to formula I-b, wherein:
(a) $R^1$ is halogen, halogenated alkyl or halogenated alkoxy;
(b) $R^2$ is hydrogen;
(c) $R^4$ is $(C_1-C_3)$alkyl; and
(d) W is —$CH_2$—.

Another embodiment are the compounds according to formula I-b, wherein:
(a) $R^1$ is halogenated alkyl;
(b) $R^2$ and $R^3$ are both hydrogen;
(c) $R^4$ is $(C_1-C_3)$alkyl; and
(d) W is —$CH_2$—.

Another embodiment are the compounds according to formula I-c and all pharmaceutically acceptable salts thereof, wherein formula I-c is:

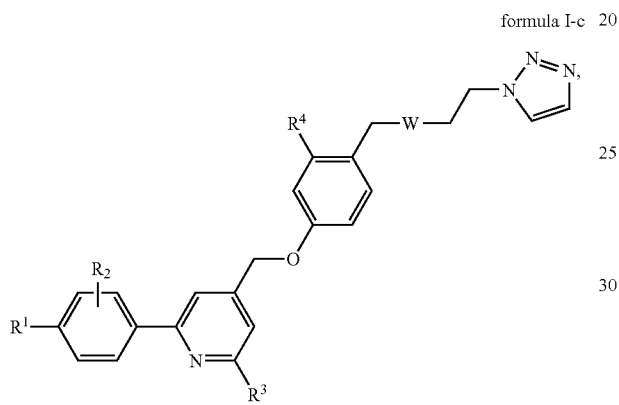

formula I-c wherein:
(a) $R^1$ is halogen, alkyl, alkoxy, halogenated alkyl or halogenated alkoxy;
(b) $R^2$ is hydrogen or halogen;
(c) $R^3$ is hydrogen or $(C_1-C_3)$alkyl;
(d) $R^4$ is hydrogen or $(C_1-C_3)$alkyl; and
(e) W is —$CH_2$—, —O—, —S—, —S(O)— or —$S(O)_2$—.

Another embodiment are the compounds according to formula I-c, wherein:
(a) $R^2$ is hydrogen; and
(b) W is —$CH_2$—, —O— or —S(O)—.

Another embodiment are the compounds according to formula I-c, wherein $R^2$ is hydrogen and W is —$CH_2$—.

Such compounds, for example, may be selected from the group consisting of:
(a) 4-[4-(4-[1,2,3]Triazol-1-yl-butyl)-phenoxymethyl]-2-(4-trifluoromethyl-phenyl)-pyridine;
(b) 4-[3-Methyl-4-(4-[1,2,3]triazol-1-yl-butyl)-phenoxymethyl]-2-(4-trifluoromethyl-phenyl)-pyridine;
(c) 4-[4-(4-[1,2,3]Triazol-1-yl-butyl)-phenoxymethyl]-2-(4-trifluoromethoxy-phenyl)-pyridine; and
(d) 4-[3-Methyl-4-(4-[1,2,3]triazol-1-yl-butyl)-phenoxymethyl]-2-(4-trifluoromethoxy-phenyl)-pyridine.

Another embodiment are the compounds according to formula I-c, wherein:
(a) $R^1$ is halogen, halogenated alkyl or halogenated alkoxy;
(b) $R^2$ is hydrogen;
(c) $R^4$ is $(C_1-C_3)$alkyl; and
(d) W is —$CH_2$—.

Another embodiment are the compounds according to formula I-c, wherein:
(a) $R^1$ is halogenated alkyl or halogenated alkoxy;
(b) $R^2$ is hydrogen;
(c) $R^4$ is $(C_1-C_3)$alkyl; and
(d) W is —$CH_2$—.

Another embodiment are the compounds according to formula I-d and all pharmaceutically acceptable salts thereof, wherein formula I-d is:

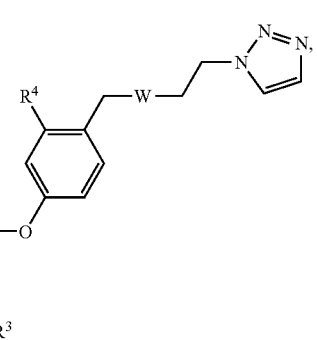

formula I-d wherein:
(a) $R^1$ is halogen, alkyl, alkoxy, halogenated alkyl or halogenated alkoxy;
(b) $R^2$ is hydrogen or halogen;
(c) $R^3$ is hydrogen or $(C_1-C_3)$alkyl;
(d) $R^4$ is hydrogen or $(C_1-C_3)$alkyl; and
(e) W is —$CH_2$—, —O—, —S—, —S(O)— or —$S(O)_2$—.

Another embodiment are the compounds according to formula I-d, wherein:
(a) $R^2$ is hydrogen; and
(b) W is —$CH_2$—, —O— or —S(O)—.

Another embodiment are the compounds according to formula I-d, wherein
$R^2$ is hydrogen and
W is —$CH_2$—.

Another embodiment are the compounds according to formula I-d, wherein
$R^2$ and $R^3$ are both hydrogen and
W is —$CH_2$—.

Another embodiment are the compounds according to formula I-d, wherein:
(a) $R^1$ is halogen, halogenated alkyl or halogenated alkoxy;
(b) $R^2$ and $R^3$ are both hydrogen; and
(c) W is —$CH_2$—.

Such compounds, for example, may be selected from the group consisting of:
(a) 2-[4-(4-[1,2,3]Triazol-1-yl-butyl)-phenoxymethyl]-6-(4-trifluoromethyl-phenyl)-pyridine;
(b) 2-[3-Methyl-4-(4-[1,2,3]triazol-1-yl-butyl)-phenoxymethyl]-6-(4-trifluoromethyl-phenyl)-pyridine;
(c) 2-[3-Methyl-4-(4-[1,2,3]triazol-1-yl-butyl)-phenoxymethyl]-6-(4-trifluoromethoxy-phenyl)-pyridine
(d) 3-[4-(4-[1,2,3]Triazol-1-yl-butyl)-phenoxymethyl]-5-(4-trifluoromethyl-phenyl)-pyridine;
(e) 2-(4-Chloro-phenyl)-6-[3-methyl-4-(4-[1,2,3]triazol-1-yl-butyl)-phenoxymethyl]-pyridine;
(f) 2-(4-Chloro-phenyl)-6-[4-(4-[1,2,3]triazol-1-yl-butyl)-phenoxymethyl]-pyridine; and (g) 2-(3-Chloro-phenyl)-6-[3-methyl-4-(4-[1,2,3]triazol-1-yl-butyl)-phenoxymethyl]-pyridine.

Another embodiment are the compounds according to formula I-d, wherein:
(a) $R^1$ is halogen, halogenated alkyl or halogenated alkoxy;
(b) $R^2$ and $R^3$ are hydrogen; and
(c) W is —$CH_2$—.

Another embodiment are the compounds according to formula I-d, wherein:
(a) $R^1$ is halogen, halogenated alkyl or halogenated alkoxy;
(b) $R^2$ and $R^3$ are hydrogen;
(c) $R^4$ is ($C_1$-$C_3$)alkyl; and
(d) W is —$CH_2$—.

Another embodiment are the compounds according to formula I-e and all pharmaceutically acceptable salts thereof, wherein formula I-e is:

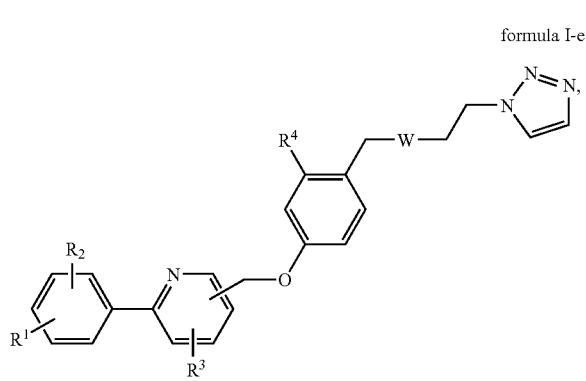

formula I-e wherein:
(a) $R^1$ is halogen, alkyl, alkoxy, halogenated alkyl or halogenated alkoxy;
(b) $R^2$ is hydrogen or halogen;
(c) $R^3$ is hydrogen or ($C_1$-$C_3$)alkyl;
(d) $R^4$ is hydrogen or ($C_1$-$C_3$)alkyl; and
(e) W is —$CH_2$—, —O—, —S—, —S(O)— or —$S(O)_2$—.

Another embodiment are the compounds according to formula I-e, wherein $R^2$ is hydrogen and W is —$CH_2$—, —O— or —S(O)—.

Another embodiment are the compounds according to formula I-e, wherein:
(a) $R^1$ is halogen, halogenated alkyl or halogenated alkoxy; and
(b) W is —$CH_2$—, —O—, —S— or —S(O)—.

Another embodiment are the compounds according to formula I-e, wherein
$R^2$ is hydrogen and
W is —$CH_2$—.

Another embodiment are the compounds according to formula I-e, wherein:
(a) $R^1$ is halogen, halogenated alkyl or halogenated alkoxy;
(b) $R^2$ is hydrogen; and
(c) W is —$CH_2$—.

Another embodiment are the compounds according to formula I-f and all pharmaceutically acceptable salts thereof, wherein formula I-f is:

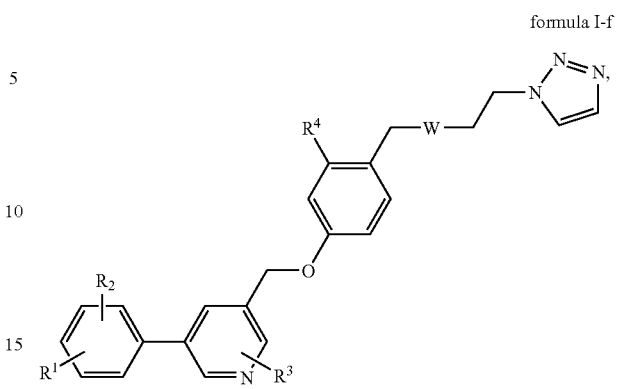

formula I-f wherein:
(a) $R^1$ is halogen, alkyl, alkoxy, halogenated alkyl or halogenated alkoxy,
(b) $R^2$ is hydrogen or halogen;
(c) $R^3$ is hydrogen or ($C_1$-$C_3$)alkyl;
(d) $R^4$ is hydrogen or ($C_1$-$C_3$)alkyl; and
(e) W is —$CH_2$—, —O—, —S—, —S(O)— or —$S(O)_2$—.

Another embodiment are the compounds according to formula I-f, wherein
$R^2$ and $R^3$ are both hydrogen and
W is —$CH_2$—.

Another embodiment are the compounds according to formula I-f, wherein:
(a) $R^1$ is halogen, halogenated alkyl or halogenated alkoxy;
(b) $R^2$ and $R^3$ are hydrogen; and
(c) W is —$CH_2$—.

Such compounds, for example, may be selected from the group consisting of:
(a) 2-[4-(4-[1,2,3]Triazol-1-yl-butyl)-phenoxymethyl]-6-(4-trifluoromethoxy-phenyl)-pyridine;
(b) 3-[3-Methyl-4-(4-[1,2,3]triazol-1-yl-butyl)-phenoxymethyl]-5-(4-trifluoromethyl-phenyl)-pyridine;
(c) 3-[3-Methyl-4-(4-[1,2,3]triazol-1-yl-butyl)-phenoxymethyl]-5-(4-trifluoromethoxy-phenyl)-pyridine;
(d) 3-[4-(4-[1,2,3]Triazol-1-yl-butyl)-phenoxymethyl]-5-(4-trifluoromethoxy-phenyl)-pyridine;
(e) 3-(4-Chloro-phenyl)-5-[3-methyl-4-(4-[1,2,3]triazol-1-yl-butyl)-phenoxymethyl]-pyridine;
(f) 3-(4-Chloro-phenyl)-5-[4-(4-[1,2,3]triazol-1-yl-butyl)-phenoxymethyl]-pyridine; and
(g) 3-(3-Chloro-phenyl)-5-[3-methyl-4-(4-[1,2,3]triazol-1-yl-butyl)-phenoxymethyl]-pyridine.

Another embodiment are the compounds according to formula I-f, wherein:
(a) $R^1$ is halogen, halogenated alkyl or halogenated alkoxy;
(b) $R^2$ and $R^3$ are hydrogen;
(c) $R^4$ is ($C_1$-$C_3$)alkyl; and
(d) W is —$CH_2$—.

Another embodiment are the compounds according to formula I, wherein W is —S—.

Another embodiment are the compounds according to formula I, wherein W is —$S(O)_2$—.

Another embodiment are the compounds according to formula I, wherein
$R^2$ is hydrogen and
W is —O—, —S—, —S(O)—, or —$S(O)_2$—.

Another embodiment are the compounds according to formula I, wherein
R$^4$ is (C$_1$-C$_3$)alkyl and
W is —O—, —S—, —S(O)—, or —S(O)$_2$—.

Another embodiment are the compounds according to formula I, wherein:
(a) R$^2$ is hydrogen;
(b) R$^4$ is (C$_1$-C$_3$)alkyl; and
(c) W is —O—, —S—, —S(O)—, or —S(O)$_2$—.

Another embodiment are the compounds according to formula I-a, wherein:
(a) R$^2$ is hydrogen;
(b) R$^4$ is (C$_1$-C$_3$)alkyl; and
(c) W is —O—, —S—, —S(O)—, or —S(O)$_2$—.

Another embodiment are the compounds according to formula I-b, wherein:
(a) R$^2$ is hydrogen;
(b) R$^4$ is (C$_1$-C$_3$)alkyl; and
(c) W is —O—, —S—, —S(O)—, or —S(O)$_2$—.

Another embodiment are the compounds according to formula I-c, wherein:
(a) R$^2$ is hydrogen;
(b) R$^4$ is (C$_1$-C$_3$)alkyl; and
(c) W is —O—, —S—, —S(O)—, or —S(O)$_2$—.

Another embodiment are the compounds according to formula I-d, wherein:
(a) R$^2$ and R$^3$ are both hydrogen;
(b) R$^4$ is (C$_1$-C$_3$)alkyl; and
(c) W is —O—, —S—, —S(O)—, or —S(O)$_2$—.

Another embodiment are the compounds according to formula I-e, wherein:
(a) R$^2$ is hydrogen;
(b) R$^4$ is (C$_1$-C$_3$)alkyl; and
(c) W is —O—, —S—, —S(O)—, or —S(O)$_2$—.

Another embodiment are the compounds according to formula I-d, wherein:
(a) R$^2$ is halogen, halogenated alkyl or halogenated alkoxy;
(b) R$^4$ is (C$_1$-C$_3$)alkyl; and
(c) W is —CH$_2$—, —O—, —S— or —S(O)—.

Another embodiment are the compounds according to formula I-d, wherein:
(a) R$^1$ is halogen, halogenated alkyl or halogenated alkoxy;
(b) R$^4$ is (C$_1$-C$_3$)alkyl; and
(c) W is —CH$_2$—.

Another embodiment are the compounds according to formula I-d, wherein:
(a) R$^1$ is halogen, halogenated alkyl or halogenated alkoxy;
(b) R$^2$ is hydrogen;
(c) R$^4$ is (C$_1$-C$_3$)alkyl; and
(d) W is —CH$_2$—.

Another embodiment of the invention is a process for the manufacture of the compounds of formula I, wherein:
(a) the compound of formula II:

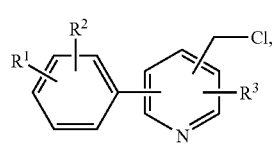

formula II wherein R$^1$, R$^2$ and R$^3$ have the significance as given in formula I previously, is reacted with a compound of formula III:

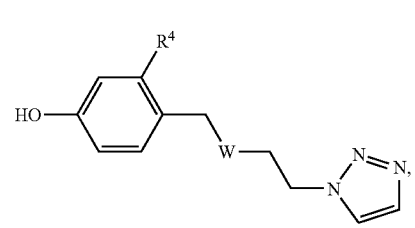

formula III wherein R$^4$ and W have the significance given in formula I previously, to obtain the respective compound of formula I;

(b) said compound is optionally isolated from the reaction mixture, and (c) optionally converted into a pharmaceutically acceptable salt.

The compounds of formula I or I-a, or a pharmaceutically acceptable salt thereof, which are subject of the present invention, may be prepared by any process known to be applicable to the preparation of chemically-related compounds. Such processes, when used to prepare a compound of the formula I or I-a, or a pharmaceutically-acceptable salt thereof, are illustrated by the following representative schemes 1 to 3 and examples in which, unless otherwise stated, R$^1$, R$^2$, R$^3$, R$^4$, and W have the significance given previously for formula I. Necessary starting materials are either commercially available or they may be obtained by standard procedures of organic chemistry. The preparation of such starting materials is e.g. described within the accompanying examples or in the literature cited below with respect to scheme 1 to 3. Alternatively necessary starting materials are obtainable by analogous procedures to those illustrated which are within the ordinary skill of an organic chemist or they can be prepared according to WO 2005/049573, WO 03/068749, WO 2004/007439, EP 0 284 174, U.S. Pat. No. 6,716,863 or U.S. Pat. No. 6,743,924.

Scheme 1

In scheme 1 a preferred method for the preparation of the compounds of formula I is described.

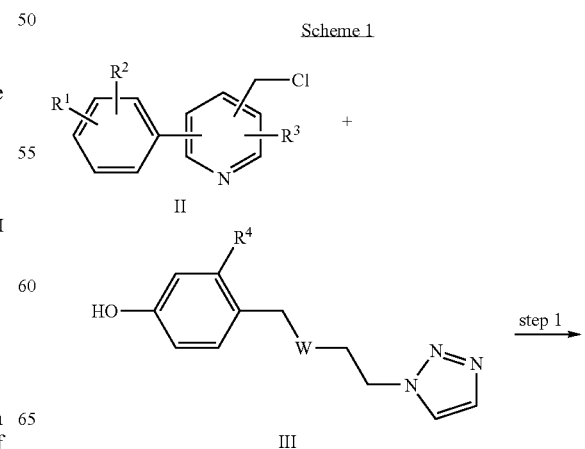

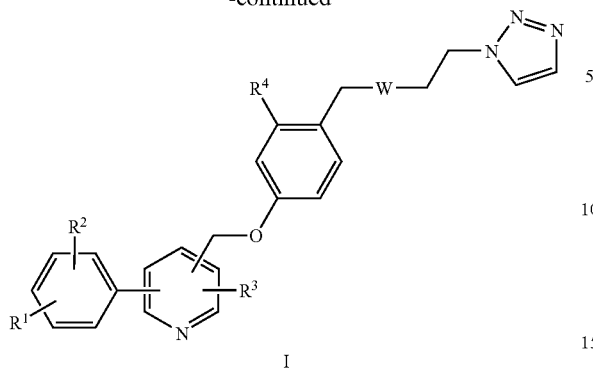

In scheme 1, $R^1$, $R^2$, $R^3$, $R^4$ and W have the significance as given previously for formula I.

The derivatives of formula I can be obtained by reactions well known to someone skilled in the art, e.g. by alkylation of compounds of formula III with compounds of formula II according to step 1 scheme 1. The alkylation can be carried out in the presence of potassium iodide or sodium iodide in solvents like N,N-dimethylformamide (DMF), methanol, ethanol, isopropanol and 2-butanone. Typical bases for this reaction are sodium methylate, sodium hydride, lithium diisopropyl amide or cesium carbonate. The reaction temperatures may vary from 0° C. to 150° C. The preparation of the chloromethyl-phenylpyridines of formula II is described in scheme 2 and scheme 3 below.

The phenolic intermediates of formula III, wherein W is —CH$_2$—, can be prepared e.g. according to U.S. Pat. No. 6,743,924 or U.S. Pat. No. 6,716,863.

The phenolic intermediates of formula III, wherein W is —O—, —S—, —S(O)— or —S(O)$_2$, may be prepared by reaction of a compound of formula IV with a compound of formula V:

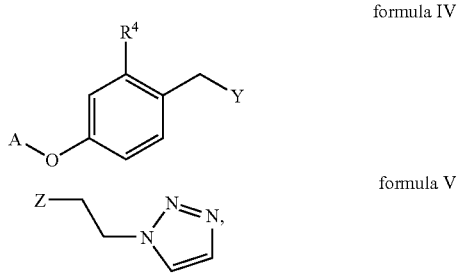

wherein:
A denotes a suitable protecting group as defined below,
Y denotes a thiol group and
Z denotes a suitable leaving group as defined below, optional oxidation (with e.g. meta-chloro-perbenzoic acid (mCPBA) or Oxone®) of the obtained thioether to yield a sulfoxide or a sulfone, and subsequent removal of the protecting group A; or alternatively, wherein:
A denotes a suitable protecting group as defined below, and one of Y or Z denotes a hydroxy group, while the other denotes a suitable leaving group E as defined below, and subsequent removal of the protecting group A.

Reactions of compounds of formula IV with compounds of formula V are well known in the art. Typically, such alkylation reaction may be carried out in solvents like N,N-dimethylformamide (DMF), methanol, ethanol and isopropanol. Typical bases for this reaction are alkaline carbonates, sodium methylate, sodium hydride or lithium diisopropyl amide. The reaction temperatures may vary from 20° C. to 150° C. Other preferred alkylation procedures make use of alkaline carbonates as bases in solvents like ketones, for example cesium carbonate in butanone at reflux temperature, or sodium hydride in DMF at room temperature. Suitable leaving groups Y are those typically used in alkylation reactions and well known to the skilled artisan. Examples of such leaving groups are, among others, the anions of halogens, especially iodide, bromide or chloride, p-toluenesulfonate (tosylate), methanesulfonate (mesylate), trifluoromethansulfonate (triflate) or the azido group.

The hydroxy protecting group A as mentioned herein is a conventional protecting group as known by the skilled artisan. Examples are tert-butoxycarbonyl (boc), propen-3-yl (allyl), triphenylmethyl (trityl) and silyl groups, e.g. tert.-butyl-dimethyl-silyl, triisopropyl-silyl.

Removal of a protecting group on a hetero atom depends on the nature of such group. Typical examples are the removal of a trityl group under acidic conditions, for example with aqueous formic acid in tetrahydrofuran (THF) under reflux or the removal of a tert-butoxycarbonyl group with trifluoroacetic acid in dichloromethane at room temperature or the removal of a substituted silyl group with tetrabutylammonium fluoride in aqueous THF at room temperature. An allyl group can smoothly be removed by treating the substrate with catalytic amounts of a palladium complex, e.g. Pd(PPh$_3$)$_4$ in dichloromethane in the presence of an allyl-acceptor such as 1,3-dimethylbarbituric acid.

Scheme 2 and Scheme 3

In scheme 2 and scheme 3 a preferred method for the preparation of the chloromethyl-phenylpyridines of formula II or formula II-a, which represent important intermediates for the preparation of the compounds of formula I or I-a is described.

The chloromethyl-phenylpyridines of formula II can be prepared by two general methods, the first one shown in scheme 2 involving a Suzuki-Miyaura-Coupling, which allows a more general access to this compound class. The second method, that is shown in scheme 3, gives easy access to compounds with a phenyl substitution at the ortho-position of the pyridine ring (formula II-a).

Scheme 2

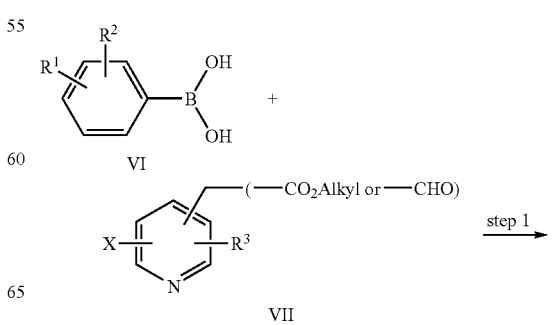

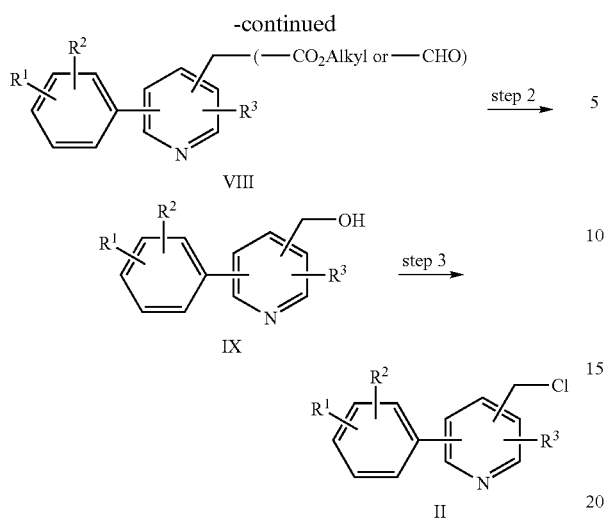

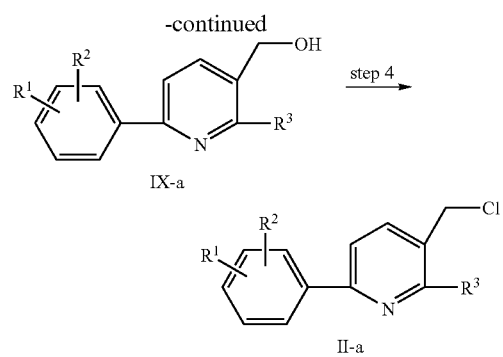

In scheme 2, $R^1$, $R^2$ and $R^3$ have the significance as given previously for formula I and X is iodine or bromine.

In step 1, the compounds of formula VI and formula VII are reacted in a coupling reaction (Suzuki-coupling, step 1) which can be performed under different reaction conditions well known in the literature. Preferred reaction conditions are described in Meier, P., et al, Synthesis (2003) 551-554 and WO 2005/040100, including a mixture of 1,2-dimethoxyethane and aqueous sodium carbonate solution, the latter also working as the required base, together with the use of palladium tetrakistriphenylphosphine as catalyst.

Transformation of the obtained phenylpyridine derivatives of VIII in step 2, scheme 2, to the corresponding alcohols IX is achieved by complex hydrides, most conveniently with diisobutylaluminiumhydrid (DIBAL) or lithium aluminum hydride in tetrahydrofuran (THF). In step 3, scheme 3, the obtained alcohols of formula IX are reacted with thionyl chloride in dichloromethane to yield the chlorides of formula II.

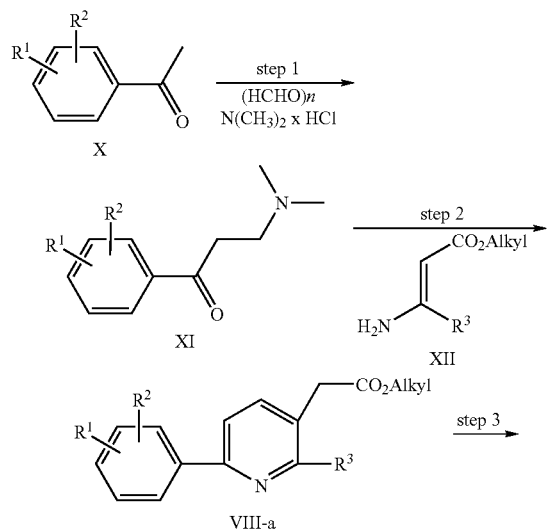

In scheme 3, $R^1$, $R^2$ and $R^3$ have the significance as previously above for formula I.

Heterocycles of formula II-a can be prepared by an alternative route shown in scheme 3. In a Mannich-type synthesis a mixture of ketones of formula X with paraformaldehyde and dimethylamine hydrochloride in a solvent like ethanol in the presence of an acid like 37% HCl is heated to reflux for 2 to 10 hours to give aminoketones of formula XI (scheme 3, step 1). Reaction of compounds of formula XI with 3-aminocrotonic acid esters of formula XII in acetic acid at reflux for 2 to 8 hours gives esters of formula VIII-a (scheme 3, step 2) (see e.g. WO 2005/049573), which are converted to alcohols of formula IX-a (scheme 3, step 3) and subsequently to chlorides of formula II-a (scheme 3, step 4) by the same methods described for the compounds of formula IX and of formula II in scheme 2, step 2 and scheme 2, step 3). Pyridines II-a can alternatively be synthesized procedures described in Al-Saleh, B., et al, J. Heterocyclic Chem. 39 (2002) 1035-1038.

The compounds according to the present invention may exist in the form of their pharmaceutically acceptable salts. The term "pharmaceutically acceptable salt" refers to conventional acid-addition salts that retain the biological effectiveness and properties of the compounds of formula I and are formed from suitable non-toxic organic or inorganic acids. Examples of acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, naphthalenesulfonic acid, naphthalenedisulfonic acid, methanesulfonic acid, ethanesulfonic acid and the like. The chemical modification of a pharmaceutical compound (i.e. a drug) into a salt is a technique well known to pharmaceutical chemists to obtain improved physical and chemical stability, hygroscopicity, flowability and solubility of compounds. See, e.g., Stahl, P. H., and Wermuth, G., (editors), Handbook of Pharmaceutical Salts, Verlag Helvetica Chimica Acta (VHCA), Zurich, (2002) or Bastin, R. J., et al., Organic Proc. Res. Dev. 4 (2000) 427-435.

Preferred are the pharmaceutically acceptable salts, which are formed with p-toluenesulfonic acid, naphthalenesulfonic acid, naphthalenedisulfonic acid, methanesulfonic acid and hydrochloric acid.

The compounds of formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases which are commercially available.

Pharmacological Activity

The compounds of formula I and their pharmaceutically acceptable salts possess valuable pharmacological properties. It has been found that said compounds show anti-proliferative activity. Consequently the compounds of the present invention are useful in the therapy and/or prevention of proliferative disorders such as cancer. The activity of the present compounds as antiproliferative inhibitors is demonstrated by the following biological assay.

Viability Assay in HEK293 Cells

A viability assay was performed using the CellTiter-Glo® Luminescent Cell Viability Assay (see Promega Corporation's Technical Bulletin No. 288, pp. 1-11 [revised 2/04] which is hereby incorporated by reference in its entirety). This assay is a homogeneous method of determining the number of viable cells in culture based on quantitation of the ATP present, an indicator of metabolically active cells. The assay is designed for use with multiwell formats, making it ideal for automated high-throughput screening (HTS), cell proliferation and cytotoxicity assays. The homogeneous assay procedure involves adding a single reagent (containing luciferase, luciferan substrate, and buffer) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The above-referenced assay generates a "glow-type" luminescent signal, produced by the luciferase reaction, which has a half-life generally greater than five hours, depending on cell type and medium used. The extended half-life eliminates the need to use reagent injectors and provides flexibility for continuous or batch mode processing of multiple plates. The unique homogeneous format avoids errors that may be introduced by other ATP measurement methods that require multiple steps.

HEK293 cells (human embryonic kidney cell line transformed by Adenovirus 5 fragments, ATCC-No. CRL 1573) were cultivated in Dulbecco's Modified Eagle Medium (DMEM) with Glutamax™ (cell culture media that contains L-Alanyl-L-Glutamine [a stabilized form/source of L-Glutamine] from Invitrogen, Cat-No. 31966-021), 5% Fetal Calf Serum (FCS, Sigma Cat-No. F4135 (FBS)), 100 Units/ml penicillin/100 µg/ml streptomycin (=Pen/Strep from Invitrogen Cat. No. 15140). For the assay the cells were seeded in 384 well plates, 5000 cells per well, in the same medium. The next day the test compounds were added in various concentrations ranging from 3 µM to 0.00015 µM (10 concentrations, 1:3 diluted). After 7 days the viability assay was done according to the instructions of the manufacturer. In brief: the cell-plate was equilibrated to room temperature for approximately 30 minutes and than the reagent (containing luciferase, luciferan substrate, and buffer) was added. The contents were carefully mixed for 15 minutes to induce cell lysis. After 45 minutes the luminescent signal was measured in Victor 2, (scanning multiwell spectrophotometer, Wallac).

Details:
  day:
    Medium: Dulbecco's Modified Eagle Medium (DMEM) with Glutamax™ (Invitrogen, 31966-021), 5% Fetal Calf Serum (FCS, Sigma Cat-No. F4135 (FBS)), Pen/Strep (Invitrogen Cat. No. 15140).
    HEK293 (ATCC-No. CRL 1573): 5000 cells in 60 µl per well of 384 well plate (Greiner 781098, white plates)
    Incubate 24 h at 37° C., 5% $CO_2$
  2. day Induction (Substance testing):

In general the dilution steeps are 1:3 a) Add 8 µl of 10 mM stock solution of compound to 72 µl DMSO b) dilute 9×1:3 (always 30 µl to 60 µl DMSO) in this DMSO dilution row (results in 10 wells with concentrations from 1000 µM to 0.06 µM)

c) dilute each concentration 1:4.8 (10 µl compound dilution to 38 µd medium)

d) dilute each concentration 1:10 (10 µl compound dilution to 90 µl medium)

e) add 10 µl of every concentration to 60 µl medium in the cell plate resulting in final concentration of DMSO: 0.3% in every well and resulting in final concentration of compounds from 3 µM to 0.00015 µM Incubate 168 h (7 days) at 37° C., 5% $CO_2$ Analysis:
  Add 30 µl CellTiter-Glo™ Reagent (containing luciferase, luciferan substrate, and buffer)/well,
  shake 15 minutes at room temperature
  incubate further 45 minutes at room temperature without shaking.

Measurement:
  Victor 2 scanning multiwell spectrophotometer (Wallac), Luminescence mode
  Determine $IC_{50}$ with XL-fit (XLfit® software [ID Business Solution Ltd., Guilford, Surrey, UK]).

A significant inhibition of HEK293 cell viability was detected, which is exemplified by the compounds shown in Table 1:

TABLE 1

| Results: | |
|---|---|
| Examples | IC50 HEK293 [nM] |
| 5 | 89 |
| 4 | 365 |
| 3, 6, 7, 8, 11, 16, 17, 19, 20, 21, 22, 27, 42 | 5-1000 |
| 9, 13, 15, 18, 23, 26, 28, 30, 33, 35, 38, 43 | 1000-5000 |

The compounds according to this invention and their pharmaceutically acceptable salts can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically acceptable, inorganic or organic carriers. For example, lactose, corn starch or derivatives thereof, talc, stearic acids or it's salts and the like can be used as carriers for tablets, coated tablets, dragées and hard gelatine capsules. Suitable carriers for soft gelatine capsules are, for example, vegetable oils, waxes, fats, semi-solid and liquid polyols and the like. However, depending on the nature of the active substance, carriers may not be required for some soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions may comprise, for example, the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG (direct tabletting grade) | 125 | 105 | 30 | 150 |
| 3. | Sta-Rx 1500 (pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:

1. Mix items 1, 2, 3 and 4 and granulate with purified water.

2. Dry the granules at 50° C.

3. Pass the granules through suitable milling equipment.

4. Add item 5 and mix for three minutes; compress on a suitable press.

b) Capsule Formulation:

| Item | Ingredients | mg/tablet | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:

1. Mix items 1, 2 and 3 in a suitable mixer for 30 minutes.

2. Add items 4 and 5 and mix for 3 minutes.

3. Fill into a suitable capsule.

The present invention provides pharmaceutical compositions containing a compound of formula I or a pharmaceutically acceptable salt thereof and one or more pharmaceutically acceptable carriers, as well as a process for their production, which comprises bringing one or more compounds of the present invention and/or pharmaceutically acceptable salts and, if desired, one or more other therapeutic substances into a galenical administration form together with one or more pharmaceutically acceptable carriers.

In accordance with the invention the compounds of the present invention as well as their pharmaceutically acceptable salts are useful in the control or prevention of illnesses. Based on their antiproliferative activity, said compounds are useful for the treatment of diseases such as cancer in humans or animals and for the production of corresponding pharmaceutical compositions. The dosage depends on various factors such as manner of administration, species, age and/or individual state of health.

Another embodiment of the invention is pharmaceutical compositions, containing one or more compounds of formula I together with one or more pharmaceutically acceptable carriers.

Another embodiment of the invention is pharmaceutical composition comprising a therapeutically effective amount of one or more compounds of formula I together with one or more pharmaceutically acceptable carriers. Still another embodiment of the invention is said pharmaceutical composition for the inhibition of tumor growth.

Another embodiment of the invention is a pharmaceutical composition, containing one or more compounds according to formula I, for the treatment of cancer.

Another embodiment of the invention is a pharmaceutical composition, containing one or more compounds of formula I as active ingredients together with pharmaceutically acceptable carriers for the treatment of colorectal, breast, lung, prostate, pancreatic, gastric, bladder, ovarian, melanoma, neuroblastoma, cervical, kidney or renal cancers, leukemias or lymphomas.

Still another embodiment of the invention is the use of a compound of formula I for the manufacture of corresponding pharmaceutical compositions for the inhibition of tumor growth. Another embodiment of the invention is the use of a compound according to formula I, for the manufacture of corresponding pharmaceutical compositions for the treatment of cancer.

Another embodiment of the invention is the use of the compounds of formula I as anti-proliferating agents.

Still another embodiment of the invention is the use of a compound of formula I for the treatment of cancer.

The following examples and references are provided to aid the understanding of the present invention, the true scope of which is set forth in the appended claims. It is understood that modifications can be made in the procedures set forth without departing from the spirit of the invention.

EXAMPLES

Example 1

2-[4-(4-[1,2,3]Triazol-1-yl-butyl)-phenoxymethyl]-5-(4-trifluoromethyl-phenyl)-pyridine Preparation of 2-chloromethyl-5-(4-trifluoromethyl-phenyl)-pyridine i) 5-(4-Trifluoromethyl-phenyl)-pyridine-2-carbaldehyde 439 mg (0.38 mmol) Pd(PPh$_3$)$_4$ was added under argon at room temperature (r.t.) to a solution of 823 mg (3.76 mmol) 5-bromo-pyridine-2-carbaldehyde in 30 ml 1,2-dimethoxyethane and stirred for 15 min. 14.5 ml (29.0 mmol) of 2 M sodium carbonate solution and 1.00 g (5.27 mmol) 4-trifluoromethyl-phenylboronic acid were added and the mixture heated to boiling temperature for 18 hours (h). The reaction mixture was cooled to room temperature (r.t.), filtered, and the filtrate evaporated. The residue was taken up with ethyl acetate, washed twice with water, dried over sodium sulphate and evaporated. Chromatography on silica (eluent: ethyl acetate/n-heptane 1:3) gave 630 mg (48%) of 5-(4-trifluoromethyl-phenyl)-pyridine-2-carbaldehyde.

MS: 252.2 (ESI+)

$^1$H-NMR (400 MHz, D$_6$-DMSO): δ=7.49 (d, 2H, Ar—CF$_3$), 8.06 (d, 1H, pyridine), 8.08 (d, 2H, Ar—CF$_3$), 8.43 (d, 1H, pyridine), 9.22 (s, 1H, pyridine), 10.06 s, 1H, CHO).

ii) [5-(4-Trifluoromethyl-phenyl)-pyridin-2-yl]-methanol 178 mg (4.70 mmol) lithium aluminium hydride were given to 5 ml tetrahydrofuran (THF) and stirred at room temperature (r.t.) for 20 min. A solution of 590 mg (2.35 mmol) 5-(4-trifluoromethyl-phenyl)-pyridine-2-carbaldehyde in 5 ml THF was added drop by drop within 15 min., and the mixture stirred for 3 h. 9 ml conc. sodium chloride solution was added slowly at 0° C. and stirring continued for 60 min. The mixture was adjusted to pH=5 by addition of conc. HCl. A formed salt precipitate was isolated by filtration and washed with THF. The combined THF-solutions were evaporated, the residue extracted twice with ethyl acetate, the organic phase dried (sodium sulphate), evaporated, and the obtained material (270 mg, 45%) used without further purification.

MS: 254.1 (ESI+).

iii) 2-Chloromethyl-5-(4-trifluoromethyl-phenyl)-pyridine 658 mg (0.40 ml, 5.53 mmol) thionyl chloride is added drop by drop at 0° C. to a solution of 0.2 ml N,N-dimethylformamide (DMF) and 700 mg (2.76 mmol) [5-(4-Trifluoromethyl-phenyl)-pyridin-2-yl]-methanol, stirred for 5 min. at 0° C., and at room temperature (r.t.) for 1 h. The mixture is poured on ice/sodium bicarbonate solution and the organic phase separated. The water phase is extracted with ethyl acetate. The combined organic phases were washed with water, dried (sodium sulphate), and evaporated. Purification by chromatography on silica (eluent: ethyl acetate/n-heptane 1:4) gave 170 mg (23%) of 2-Chloromethyl-5-(4-trifluoromethyl-phenyl)-pyridine as slightly pink crystals.

MS: 272.1 (ESI+).

$^1$H-NMR (400 MHz, D$_6$-DMSO): δ=4.86 (s, 2H, CH$_2$Cl), 7.69 (d, 1H, 3-H-pyridine), 7.87 (d, 2H, Ar—CF$_3$), 7.99 (d, 2H, Ar—CF$_3$), 8.22 (d, 1H, 4-H-pyridine), 8.95 (s, 1H, 6-H-pyridine).

Preparation of 2-[4-(4-[1,2,3]-Triazol-1-yl-butyl)-phenoxymethyl]-5-(4-trifluoromethyl-phenyl)-pyridine 8.0 mg (0.31 mmol) of 95% sodium hydride were added at 0° C. to a solution of 61 mg (0.28 mmol) 4-(4-[1,2,3]triazol-1-yl-butyl)-phenol in 3.0 ml N,N-dimethylformamide and stirred for 30 min. at 0° C. 76 mg (0.28 mmol) 2-chloromethyl-5-(4-trifluoromethyl-phenyl)-pyridine were given to the reaction mixture and stirring continued at r.t overnight. After addition of 6 ml water the mixture was stirred for 1 h, the formed precipitate isolated by filtration, washed with water, methanol/water 1:1. The residue was purified by chromatography on silica (eluent: ethyl acetate) to give 95 mg (75%) of Preparation of 2-[4-(4-[1,2,3]Triazol-1-yl-butyl)-phenoxymethyl]-5-(4-trifluoromethyl-phenyl)-pyridine as white powder.

MS: 453.5 (ESI+)

$^1$H-NMR (400 MHz, D$_6$-DMSO): δ=1.49 (quintet, 2H, CH$_2$—CH$_2$—Ar), 1.81 (quintet, 2H, CH$_2$—CH$_2$-triazole), 2.54 (t, 2H, CH$_2$—Ar), 4.39 (t, 2H, CH$_2$-triazole), 5.21 (s, 2H, OCH$_2$), 6.95 (d, 2H, OAr), 7.10 (s, 2H, OAr), 7.63 (d, 1H, 3-H-pyridine), 7.70 (s, 1H, triazole), 7.86 (d, 2H, Ar—CF$_3$), 7.98 (d, 2H, Ar—CF$_3$), 8.10 (s, 1H, triazole), 8.20 (d, 1H, 4-H-pyridine), 8.96 (s, 1H, 6-H-pyridine).

Example 2

2-[3-Methyl-4-(4-[1,2,3]triazol-1-yl-butyl)-phenoxymethyl]-5-(4-trifluoromethyl-phenyl)-pyridine 8.0 mg (0.31 mmol) of 95% sodium hydride were added at 0° C. to a solution of 65 mg (0.28 mmol) 3-methyl-4-(4-[1,2,3]triazol-1-yl-butyl)-phenol in 3.0 ml N,N-dimethylformamide and stirred for 30 min. at 0° C. 76 mg (0.28 mmol) 2-chloromethyl-5-(4-trifluoromethyl-phenyl)-pyridine were given to the reaction mixture and stirring continued at r.t overnight. After addition of 6 ml water the mixture was stirred for 1 h, the formed precipitate isolated by filtration, washed with water, methanol/water 1:1. The residue was purified by chromatography on silica (eluent: ethyl acetate) to give 91 mg (70%) of the title compound as white powder.

MS: 467.5 (ESI+)

$^1$H-NMR (400 MHz, D$_6$-DMSO): δ=1.44 (quintet, 2H, CH$_2$—CH$_2$—Ar), 1.86 (quintet, 2H, CH$_2$—CH$_2$-triazole), 2.20 (s, 3H, CH$_3$), 2.52 (t, 2H, CH$_2$—Ar), 4.40 (t, 2H, CH$_2$-triazole), 5.19 (s, 2H, OCH$_2$), 6.78 (d, 1H, 6-H—OAr), 6.85 (s, 1H, 2-H—OAr), 7.01 (d, 1H, 5-H—OAr), 7.61 (d, 1H, 3-H-pyridine), 7.70 (s, 1H, triazole), 7.86 (d, 2H, Ar—CF$_3$), 7.98 (d, 2H, Ar—CF$_3$), 8.11 (s, 1H, triazole), 8.20 (d, 1H, 4-H-pyridine), 8.95 (s, 1H, 6-H-pyridine).

Example 3

5-[4-(4-[1,2,3]triazol-1-yl-butyl)-phenoxymethyl]-[2-(4-trifluoromethyl-phenyl)]-pyridine 23 mg (0.90 mmol) of 95% sodium hydride were added at 0° C. to a solution of 163 mg (0.75 mmol) 4-(4-[1,2,3]triazol-1-yl-butyl)-phenol in 4.0 ml N,N-dimethylformamide and stirred for 30 min. at 0° C. 204 mg (0.75 mmol) 5-chloromethyl-2-(4-trifluoromethyl-phenyl)-pyridine (WO 2005/049573) were given to the reaction mixture and stirring continued at r.t for 2 days. After addition of 8 ml water the mixture was stirred for 1 h, the formed precipitate isolated by filtration, washed with water, methanol/water 1:1, and a small amount of ether. The residue was purified by chromatography on silica (eluent: ethyl acetate) to give 240 mg 71% of the title compound as white powder.

MS: 453.6 (ESI+)

$^1$H-NMR (400 MHz, D$_6$-DMSO): δ=1.48 (quintet, 2H, CH$_2$—CH$_2$—Ar), 1.80 (quintet, 2H, CH$_2$—CH$_2$-triazole), 2.52 (t, 2H, CH$_2$—Ar), 4.39 (t, 2H, CH$_2$-triazole), 5.19 (s, 2H, OCH$_2$), 6.96 (d, 2H, OAr), 7.10 (d, 2H, OAr), 7.70 (s, 1H, triazole), 7.86 (d, 2H, Ar—CF$_3$), 8.00 (d, 1H, 3-H-pyridine), 8.10 (s, 1H, triazole), 8.10 (d, 1H, 4-H-pyridine), 8.32 (d, 2H, Ar—CF$_3$), 8.79 (s, 1H, 6-H-pyridine).

Example 4

5-[3-Methyl-4-(4-[1,2,3]triazol-1-yl-butyl)-phenoxymethyl]-[2-(4-trifluoromethoxy-phenyl)]-pyridine 15 mg (0.60 mmol) of 95% sodium hydride were added at 0° C. to a solution of 116 mg (0.50 mmol) 3-methyl-4-(4-[1,2,3]triazol-1-yl-butyl)-phenol in 4.0 ml N,N-dimethylformamide and stirred for 30 min. at 0° C. 144 mg (0.50 mmol) 5-chloromethyl-2-(4-trifluoromethoxy-phenyl)-pyridine were given to the reaction mixture and stirring continued at room temperature (r.t.) overnight. After addition of 8 ml water the mixture was stirred for 1 h, the formed precipitate isolated by filtration, washed with water, methanol/water 1:1, and a small amount of ether. The residue was purified by chromatography on silica (eluent: ethyl acetate/n-heptane 4:1) to give 136 mg (56%) of the title compound as white powder.

MS: 483.1 (ESI+)

$^1$H-NMR (400 MHz, D$_6$-DMSO): δ=1.42 (quintet, 2H, CH$_2$—CH$_2$—Ar), 1.85 (quintet, 2H, CH$_2$—CH$_2$-triazole), 2.20 (s, 3H, CH$_3$), 2.51 (t, 2H, CH$_2$—Ar), 4.40 (t, 2H, CH$_2$-triazole), 5.15 (s, 2H, OCH$_2$), 6.79 (d, 1H, 6-H—OAr), 6.84 (s, 1H, 2-H—OAr), 7.01 (d, 1H, 5-H—OAr), 7.48 (d, 2H, Ar—OCF$_3$), 7.70 (s, 1H, triazole), 7.95 (d, 1H, 4-H-pyridine), 8.03 (d, 1H, 3-H-pyridine), 8.11 (s, 1H, triazole), 8.22 (d, 2H, Ar—OCF$_3$), 8.74 (s, 1H, 6-H-pyridine).

Example 5

5-[3-Methyl-4-(4-[1,2,3]triazol-1-yl-butyl)-phenoxymethyl]-2-(4-trifluoromethyl-phenyl)-pyridine 15 mg (0.60 mmol) of 95% sodium hydride were added at 0° C. to a solution of 116 mg (0.50 mmol) 3-methyl-4-(4-[1,2,3]triazol-1-yl-butyl)-phenol in 4.0 ml N,N-dimethylformamide and stirred for 30 min. at 0° C. 136 mg (0.50 mmol) 5-chloromethyl-2-(4-trifluoromethyl-phenyl)-pyridine were given to the reaction mixture and stirring continued at r.t overnight. After addition of 8 ml water the mixture was stirred for 1 h, the formed precipitate isolated by filtration, washed with water, methanol/water 1:1, and a small amount of ether to give 165 mg (71%) of the title compound as white powder.

MS: 467.1 (ESI+)

$^1$H-NMR (400 MHz, D$_6$-DMSO): δ=1.42 (quintet, 2H, CH$_2$—CH$_2$—Ar), 1.85 (quintet, 2H, CH$_2$—CH$_2$-triazole), 2.51 (t, 2H, CH$_2$—Ar), 2.21 (s, 3H, CH$_3$), 2.51 (t, 2H, CH$_2$—Ar), 4.40 (t, 2H, CH$_2$-triazole), 5.17 (s, 2H, OCH$_2$), 6.79 (d, 1H, OAr), 6.85 (s, 1H, OAr), 7.01 (d, 1H, OAr), 7.71 (s, 1H, triazole), 7.86 (d, 2H, Ar—CF$_3$), 7.99 (d, 1H, pyridine), 8.10 (d, 1H, pyridine), 8.11 (s, 1H, triazole), 8.32 (d, 2H, Ar—CF$_3$), 8.79 (s, 1H, pyridine).

Example 6

2-Methyl-3-[3-Methyl-4-(4-[1,2,3]triazol-1-yl-butyl)-phenoxymethyl]-6-(4-trifluoromethyl-phenyl)-pyridine 36 mg (0.90 mmol) of 95% sodium hydride were added to at 0° C. to a solution of 173 mg (0.75 mmol) 3-methyl-4-(4-[1,2,3]triazol-1-yl-butyl)-phenol in 4.0 ml N,N-dimethylformamide and stirred for 30 min. at 0° C. 214 mg (0.75 mmol) 3-chloromethyl-2-methyl-6-(4-trifluoromethyl-phenyl)-pyridine (WO 2005/049573) were given to the reaction mixture and stirring continued at room temperature (r.t.) overnight. After addition of 8 ml water the mixture was stirred for 1 h, the formed precipitate isolated by filtration, washed with water, water/methanol 1:1, and ether. The residue was purified by chromatography on silica (eluent: ethyl acetate) to yield 227 mg (63%) of the title compound as white crystals.

MS: 481.6 (ESI+)

$^1$H-NMR (500 MHz, D$_6$-DMSO): δ=1.45 (quintet, 2H, CH$_2$—CH$_2$—Ar), 1.87 (quintet, 2H, CH$_2$—CH$_2$-triazole), 2.22 (s, 3H, OArCH$_3$), 2.53 (t, 2H, CH$_2$—Ar), 2.61 (s, 3H, pyridine-CH$_3$), 4.42 (t, 2H, CH$_2$-triazole), 5.15 (s, 2H, OCH$_2$), 6.81 (d, 1H, 6-H—OAr), 6.87 (s, 1H, 2-H—OAr), 7.03 (d, 1H, 5-H—OAr), 7.71 (s, 1H, triazole), 7.85 (d, 2H, Ar—CF$_3$), 7.92 (s, 2H, pyridine), 8.11 (s, 1H, triazole), 8.31 (d, 2H, Ar—CF$_3$).

Example 7

2-Methyl-3-[4-(4-[1,2,3]triazol-1-yl-butyl)-phenoxymethyl]-6-(4-trifluoromethyl-phenyl)-pyridine 14 mg (0.55 mmol) of 95% sodium hydride were added to at 0° C. to a solution of 109 mg (0.50 mmol) 4-(4-[1,2,3]triazol-1-yl-butyl)-phenol in 4.0 ml N,N-dimethylformamide and stirred for 30 min. at 0° C. 143 mg (0.50 mmol) 3-chloromethyl-2-methyl-6-(4-trifluoromethyl-phenyl)-pyridine were given to the reaction mixture and stirring continued at room temperature (r.t.) overnight. After addition of 8 ml water the mixture was stirred for 1 h, the formed precipitate isolated by filtration, washed twice with water, and twice with heptane. The residue was dried at 40° C. in vacuum to give 191 mg (82%) of the title compound as white powder.

MS: 467.1 (ESI+)

$^1$H-NMR (400 MHz, D$_6$-DMSO): δ=1.49 (quintet, 2H, CH$_1$—CH$_2$—Ar), 1.81 (quintet, 2H, CH$_2$—CH$_2$-triazole), 2.54 (t, 2H, CH$_2$—Ar), 2.61 (s, 3H, CH$_3$), 4.39 (t, 2H, CH$_2$-triazole), 5.16 (s, 2H, OCH$_2$), 6.98 (d, 2H, OAr), 7.11 (s, 2H, OAr), 7.70 (s, 1H, triazole), 7.85 (d, 2H, Ar—CF$_3$), 7.92 (s, 2H, pyridine), 8.11 (s, 1H, triazole), 8.31 (d, 2H, Ar—CF$_3$).

Example 8

2-Methyl-3-[4-(2-[1,2,3]triazol-1-yl-ethoxymethyl)-phenoxymethyl]-6-(4-trifluoromethyl-phenyl)-pyridine Preparation of 4-(2-[1,2,3]-Triazol-1-yl-ethoxymethyl)-phenol i) 1-Allyloxy-4-chloromethyl-benzene 7.67 g (67.0 mmol) methanesulfonyl chloride were given at 0° C. to a solution of 10.0 g (60.9 mmol) (4-allyloxy-phenyl)-methanol and 9.34 ml (67.0 mmol) triethylamine in 35 ml dichloromethane and stirred at room temperature (r.t.) overnight. The mixture was poured in ice water, extracted with dichloromethane and the organic phase dried over Na$_2$SO$_4$. After removal of solvents the residue was purified by chromatography on silica gel (ethyl acetate/n-heptane 1:5) to yield 3.12 g (28%) pale yellow oil.

$^1$H-NMR (400 MHz, [D$_6$]-DMSO): δ=4.57 (m, 2H, OCH$_2$), 4.72 (s, 2H, CH$_2$Cl), 5.26 (d, 1H, =CH$_2$), 5.39 (d, 1H, =CH$_2$), 6.04 (m, 1H, CH=CH$_2$), 6.95 (d, 2H, 2'-/6'-H), 7.35 (d, 2H, 3'-/5'-H).

ii) 1-[2-(4-Allyloxy-benzyloxy)-ethyl]-1H-[1,2,3]-triazole 197 mg (8.21 mmol) 95% sodium hydride were given at −50° C. to a solution of 1.00 g (5.47 mmol) 1-allyloxy-4-chloromethyl-benzene and 619 mg (5.47 mmol) 2-(1H-[1,2,3]-triazol-1-yl)-ethanol in 9.0 ml N,N-dimethylformamide (DMF). The mixture was allowed to warm slowly to room temperature (r.t.), stirred overnight and 10 ml water was added. The formed oil was collected with 10 ml dichloromethane, the aqueous phase extracted with 10 ml dichloromethane and the combined organic phases dried over Na$_2$SO$_4$.

Solvents were removed in vacuum and the residue purified by chromatography on silica gel (ethyl acetate/heptane 1:1) to yield 1.10 g (78%) yellow oil.

MS: M=260.3 (AP+), 258.3 (AP−).

$^1$H-NMR (400 MHz, [D$_6$]-DMSO): δ=3.79 (t, 2H, CH$_2$—CH$_2$-triazole), 4.39 (s, 2H, OCH$_2$Ph), 4.54-4.59 (m, 4H, OCH$_2$-vinyl, CH$_2$-triazole), 5.25 (d, 1H, =CH$_2$), 5.38 (d, 1H, =CH$_2$), 6.06 (m, 1H, CH=CH$_2$), 6.89 (d, 2H, 2'-/6'-H), 7.15 (d, 2H, 3'-/5'-H), 7.16 (s, 1H, triazole), 8.08 (s, 1H, triazole).

iii) 4-(2-[1,2,3]Triazol-1-yl-ethoxymethyl)-phenol

A solution of 500 mg (1.93 mmol) 1-[2-(4-allyloxy-benzyloxy)-ethyl]-1H-[1,2,3]-triazole in 10 ml dichloromethane was added to a solution of 904 mg (5.79 mmol) 1,3-dimethylbarbituric acid and 58 mg (0.05 mmol) Pd(PPh$_3$)$_4$ in 20 ml dichloromethane and stirred for 4.5 h at 40° C. The mixture was extracted with 3×20 ml sat. NaHCO$_3$-solution and 8 ml water and the combined aqueous phases were reextracted with 2×10 ml dichloromethane. The organic extracts were combined and dried over MgSO$_4$. Solvents were distilled off and the residue purified by chromatography on silica gel (ethyl acetate) to yield 248 mg (59%) of the title compound.

$^1$H-NMR (400 MHz, [D$_6$]-DMSO): δ=3.77 (t, 2H, CH$_2$—CH$_2$-triazole), 4.33 (s, 2H, OCH$_2$Ph), 4.56 (t, 2H, CH$_2$-triazole), 6.69 (d, 2H, 2'-/6'-H), 7.03 (d, 2H, 3'-/5'-H), 7.11 (s, 1H, triazole), 8.07 (s, 1H, triazole), 9.37 (s, 1H, PhOH).

14 mg (0.55 mmol) of 95% sodium hydride were added to at 0° C. to a solution of 110 mg (0.50 mmol) 3-chloromethyl-2-methyl-6-(4-trifluoromethyl-phenyl)-pyridine in 4.0 ml N,N-dimethylformamide and stirred for 30 min. at 0° C. 143 mg (0.50 mmol) 4-(2-[1,2,3]triazol-1-yl-ethoxymethyl)-phenol were given to the reaction mixture and stirring continued at room temperature (r.t.) overnight. After addition of 8 ml water the mixture was stirred for 1 h, the formed precipitate isolated by filtration, washed with water, water/methanol 1:1, and a little amount of ether. The residue was purified by chromatography on silica (eluent: ethyl acetate/n-heptane 2:1) to give 136 mg (58%) of the title compound as white powder.

MS: 468.9 (ESI+)

$^1$H-NMR (400 MHz, D$_6$-DMSO): δ=2.61 (s, 3H, CH$_3$), 3.80 (t, 2H, CH$_2$—CH$_2$-triazole), 4.41 (s, 2H, CH$_2$—Ar), 4.58 (t, 2H, CH$_2$-triazole), 5.20 (s, 2H, OCH$_2$), 7.03 (d, 2H, OAr), 7.20 (d, 2H, OAr), 7.72 (s, 1H, triazole), 7.85 (d, 2H, Ar—CF$_3$), 7.92 (s, 2H, pyridine), 8.08 (s, 1H, triazole), 8.31 (d, 2H, Ar—CF$_3$).

Example 9

2-Methyl-3-[4-(2-[1,2,3]triazol-1-yl-ethanesulfinyl-methyl)-phenoxymethyl]-6-(4-trifluoromethyl-phenyl)-pyridine Preparation of 4-(2-[1,2,3]Triazol-1-yl-ethanesulfinylmethyl)-phenol i) (4-Allyloxy-phenyl)-methanethiol

A mixture of 2.00 g (10.9 mmol) 1-allyloxy-4-chloromethyl-benzene and 917 mg (12.1 mmol) thiourea in 3.0 ml ethanol was heated to reflux for 7 h. Solvents were distilled off and the crystalline residue was washed with cold ethanol and isolated by filtration. After addition of 2.5 ml ethanol, 1.0 ml water and 0.7 ml 25% aqueous ammonia, the mixture was heated to reflux for 1 h. Ethanol was distilled off, then acidified with 0.5 ml half conc. HCl and extracted with ethyl acetate. The solution was dried over MgSO$_4$ and solvents were removed in vacuo to yield 1.59 g (81%) colorless oil, which was used immediately.

$^1$H-NMR (400 MHz, [D$_6$]-DMSO): δ=2.75 (s, 1H, SH), 3.68 (s, 2H, CH$_2$SH), 4.54 (m, 2H, OCH$_2$-vinyl), 5.26 (d, 1H, =CH$_2$), 5.38 (d, 1H, =CH$_2$), 6.05 (m, 1H, CH=CH$_2$), 6.89 (d, 2H, 2'-/6'-H), 7.24 (d, 2H, 3'-15'-H).

ii) Toluene-4-sulfonic acid 2-[1,2,3]triazol-1-yl-ethyl ester

A solution of 12.9 g (66.3 mmol) p-toluenesulfonic acid chloride, 2.03 g (16.6 mmol) 4-(N,N-dimethylamino)-pyridine and 11.2 ml (80.2 mmol) triethylamine in 150 ml dichloromethane was cooled to −10° C. A solution of 7.50 g (66.3 mmol) 2-(1H-[1,2,3]triazol-1-yl)-ethanol in 150 ml dichloromethane was added dropwise and the mixture stirred overnight at −4° C. 170 ml Ice and 170 ml dichloromethane were added and stirring continued for 10 min. followed by addition of 3.9 ml conc. HCl. The organic phase was separated, washed with sat. NaHCO$_3$-solution and brine, dried over Na$_2$SO$_4$ and solvents distilled off. Yield 15.3 g (86%) orange crystals.

$^1$H-NMR (400 MHz, [D$_6$]-DMSO): δ=2.41 (s, 3H, CH$_3$), 4.41 (t, 2H, CH$_2$—OTos), 4.67 (t, 2H, CH$_2$-triazole), 7.44 (d, 2H, Ar—H), 7.65 (d, 2H, Ar—H), 7.69 (s, 1H, triazole), 8.03 (s, 1H, triazole).

iii) 1-[2-(4-Allyloxy-benzylsulfanyl)-ethyl]-1H-[1,2,3]triazole 1.58 g (6.14 mmol) (4-allyloxy-phenyl)-methanethiol and 1.64 g (6.14 mmol) toluene-4-sulfonic acid 2-[1,2,3]triazol-1-yl-ethyl ester were dissolved in 15 ml N,N-dimethylformamide (DMF) and cooled to −30° C. 294 mg (12.3 mmol) 95% Sodium hydride were added, the mixture allowed to warm to room temperature (r.t.) and stirred for 12 h. 10 ml Water were added and the residue dissolved in dichloromethane. The organic phase was dried over Na$_2$SO$_4$, solvents removed and the remaining material purified by chromatography on silica gel (ethyl acetate/n-heptane 1:1) to yield 1.33 g (79%) yellow oil.

MS: M=298.0 (M+Na+, AP+).

$^1$H-NMR (400 MHz, [D$_6$]-DMSO): δ=2.86 (t, 2H, CH$_2$—CH$_2$-triazole), 3.65 (s, 2H, OCH$_2$Ph), 4.55 (m, 4H, OCH$_2$-vinyl, CH$_2$-triazole), 5.25 (d, 1H, =CH$_2$), 5.38 (d, 1H, =CH$_2$), 6.05 (m, 1H, CH=CH$_2$), 6.90 (d, 2H, 2'-/6'-H), 7.22 (d, 2H, 3'-/5'-H), 7.73 (s, 1H, triazole), 8.12 (s, 1H, triazole).

iv) 1-[2-(4-Allyloxy-phenylmethanesulfinyl)-ethyl]-1H-[1,2,3]triazole

A solution of 1.86 g (8.29 mmol) 77% 3-chloroperbenzoic acid in 40 ml ethyl acetate was added at −30° C. within 20 min. to a solution of 1.90 g (6.90 mmol) 1-[2-(4-allyloxy-benzylsulfanyl)-ethyl]-1H-[1,2,3]triazole in 160 ml dichloromethane and stirred for 1 h. The mixture was allowed to warm to room temperature (r.t.) washed with sat. NaHCO$_3$-solution, water and evaporated. The residue was purified by chromatography on silica gel (ethyl acetate/methanol 5:1) to give 1.25 g of the title compound as white powder.

$^1$H-NMR (400 MHz, [D$_6$]-DMSO): δ=3.11 (dt, 1H, CH$_2$—CH$_2$-triazole), 3.32 (dt, 1H, CH$_2$—CH$_2$-triazole), 3.94.1 (d, 1H, SO$_2$CH$_2$Ph), 4.12 (d, 1H, SO$_2$CH$_2$Ph), 4.56 (d, 2H, OCH$_2$-vinyl), 4.78 (m, 2H, CH$_2$-triazole), 5.26 (d, 1H, =CH$_2$), 5.39 (d, 1H, =CH$_2$), 6.02 (m, 1H, CH=CH$_2$), 6.95 (d, 2H, 2'-/6'-H), 7.22 (d, 2H, 3'-/5'-H), 7.75 (s, 1H, triazole), 8.16 (s, 1H, triazole).

v) 4-(2-[1,2,3]Triazol-1-yl-ethanesulfinylmethyl)-phenol

A solution of 1.00 g (3.43 mmol) 1-[2-(4-allyloxy-phenylmethanesulfinyl)-ethyl]-1H-[1,2,3]triazole in 60 ml dichloromethane was added to a solution of 1.61 g (10.3 mmol) 1,3-dimethylbarbituric acid and 102 mg (0.09 mmol) Pd(PPh$_3$)$_4$ in 30 ml dichloromethane and stirred for 5 h at 50° C. The mixture was extracted with 3×50 ml sat. NaHCO$_3$-solution and 20 ml water. The organic phase was discarded and the aqueous phase acidified with 2M HCl to pH=4, concentrated to a volume of 50 ml and adjusted to pH=1. After five extractions with ethyl acetate, the organic extracts were combined and dried over MgSO$_4$. After evaporation the residue was purified by chromatography on silica gel (dichloromethane/methanol 100:2) to yield 0.84 g (97%) of 4-(2-[1,2,3]Triazol-1-yl-ethanesulfinylmethyl)-phenol.

$^1$H-NMR (400 MHz, [D$_6$]-DMSO): δ=3.11 (dt, 1H, CH$_2$—CH$_2$-triazole), 3.29 (dt, 1H, CH$_2$—CH$_2$-triazole), 3.90 (d, 1H, SOCH$_2$Ph), 4.06 (d, 1H, SOCH$_2$Ph), 4.77 (m, 2H, CH$_2$-triazole), 6.74 (d, 2H, 2'-/6'-H), 7.10 (d, 2H, 3'-/5'-H), 7.74 (s, 1H, triazole), 8.16 (s, 1H, triazole), 9.49 (s, 1H, OH).

Preparation of 2-Methyl-3-[4-(2-[1,2,3]triazol-1-yl-ethanesulfinylmethyl)-phenoxymethyl]-6-(4-trifluoromethyl-phenyl)-pyridine A solution of 126 mg (mmol) 4-(2-[1,2,3]triazol-1-yl-ethanesulfinylmethyl)-phenol in 4.0 ml N,N-dimethylformamide was treated at 0° C. with 14 mg (0.55 mmol) of 95% sodium hydride and stirred at 0° C. for 30 min., then 143 mg (0.50 mmol) 3-chloromethyl-2-methyl-6-(4-trifluoromethyl-phenyl)-pyridine were added and stirring continued over night. After addition of 8 ml water, the precipitate was isolated, washed thoroughly with water, methanol/water 1:1, and a small amount of ether. The residue was purified by chromatography on silica (eluent: ethyl acetate/methanol 9:1) to give 130 mg (52%) of the title compound as white powder.

MS: 500.9 (ESI+)

$^1$H-NMR (400 MHz, D$_6$-DMSO): δ=2.62 (s, 3H, CH$_3$), 3.13 (dt, 1H, CH$_2$—CH$_2$-triazole), 3.35 (dt, 1H, CH$_2$—CH$_2$-triazole), 3.96 (d, 1H, CH$_2$—Ar), 4.15 (d, 1H, CH$_2$—Ar), 4.79 (t, 2H, CH$_2$-triazole), 5.21 (s, 2H, OCH$_2$), 7.09 (d, 2H, OAr), 7.27 (d, 2H, OAr), 7.75 (s, 1H, triazole), 7.85 (d, 2H, Ar—CF$_3$), 7.93 (s, 2H, pyridine), 8.17 (s, 1H, triazole), 8.31 (d, 2H, Ar—CF$_3$).

Example 10

2-Methyl-3-[4-(4-[1,2,3]triazol-1-yl-butyl)-phenoxymethyl]-6-(4-trifluoromethoxy-phenyl)-pyridine 17 mg (0.42 mmol) of 60% sodium hydride were added to at 0° C. to a solution of 91 mg (0.42 mmol) 4-(4-[1,2,3]triazol-1-yl-butyl)-phenol in 6.0 ml N,N-dimethylformamide and stirred for 30 min. at 0° C. 127 mg (0.42 mmol) 3-chloromethyl-2-methyl-6-(4-trifluoromethoxy-phenyl)-pyridine (WO 2005/049573) were given to the reaction mixture and stirring continued at room temperature (r.t.) overnight. After addition of 12 ml water the mixture was stirred for 1 h, the formed precipitate isolated by filtration, washed with water, n-heptane, and ether. The residue was dried at 40° C. in vacuum to give 102 mg (50%) of the title compound as white powder.

MS: 483.3 (ESI+)

$^1$H-NMR (400 MHz, D$_6$-DMSO): δ=1.48 (quintet, 2H, CH$_2$—CH$_2$—Ar), 1.81 (quintet, 2H, CH$_2$—CH$_2$-triazole), 2.54 (t, 2H, CH$_2$—Ar), 2.59 (s, 3H, CH$_3$), 4.39 (t, 2H, CH$_2$-triazole), 5.14 (s, 2H, OCH$_2$), 6.97 (d, 2H, OAr), 7.11 (s, 2H, OAr), 7.85 (d, 2H, Ar—OCF$_3$), 7.70 (s, 1H, triazole), 7.84 (d, 1H, pyridine), 7.88 (d, 1H, pyridine), 8.11 (s, 1H, triazole), 8.21 (d, 2H, Ar—OCF$_3$).

Example 11

2-Methyl-3-[3-Methyl-4-(4-[1,2,3]triazol-1-yl-butyl)-phenoxymethyl]-6-(4-trifluoromethoxy-phenyl)-pyridine 26 mg (0.66 mmol) of 60% sodium hydride were added to at 0° C. to a solution of 153 mg (0.66 mmol) 3-methyl-4-(4-[1,2,3]triazol-1-yl-butyl)-phenol in 8.0 ml N,N-dimethylformamide and stirred for 30 min. at 0° C. 200 mg (0.66 mmol) 3-chloromethyl-2-methyl-6-(4-trifluoromethoxy-phenyl)-pyridine were given to the reaction mixture and stirring continued at room temperature (r.t.) overnight. After addition of 16 ml water the mixture was stirred for 1 h, the formed precipitate isolated by filtration, washed with water, n-heptane, and ether. The residue was dried at 40° C. in vacuum to give 300 mg (91%) of the title compound as white powder.

MS: 497.4 (ES $^1$H-NMR (400 MHz, D$_6$-DMSO): δ=1.43 (quintet, 2H, CH$_2$—CH$_2$—Ar), 1.86 (quintet, 2H, CH$_2$—CH$_2$-triazole), 2.53 (t, 2H, CH$_2$—Ar), 2.58 (s, 3H, CH$_3$), 4.41 (t, 2H, CH$_2$-triazole), 5.12 (s, 2H, OCH$_2$), 6.80 (d, 1H, 6-H—OAr), 6.86 (s, 1H, 2-H—OAr), 7.02 (d, 1H, 5-H—OAr), 7.47 (d, 2H, Ar—OCF$_3$), 7.71 (s, 1H, triazole), 7.84 (d, 1H, pyridine), 7.88 (d, 1H, pyridine), 8.12 (s, 1H, triazole), 8.21 (d, 2H, Ar—OCF$_3$).

Example 12

2-Methyl-3-[4-(4-[1,2,3]triazol-1-yl-butyl)-phenoxymethyl]-6-(3-trifluoromethyl-phenyl)-pyridine 29 mg (0.73 mmol) of 60% sodium hydride were added to at 0° C. to a solution of 152 mg (0.70 mmol) 4-(4-[1,2,3]triazol-1-yl-butyl)-phenol in 8.0 ml N,N-dimethylformamide and stirred for 30 min. at 0° C. 200 mg (0.70 mmol) 3-chloromethyl-2-methyl-6-(3-trifluoromethyl-phenyl)-pyridine (WO 2005/049573) were given to the reaction mixture and stirring continued at room temperature (r.t.) overnight. After addition of 16 ml water the mixture was stirred for 1 h, the formed precipitate isolated by filtration, washed with water, water/methanol 1:1, n-heptane, and ether. The residue was dried at 40° C. in vacuum to give 288 mg (88%) of the title compound as beige powder.

MS: 467.3 (ESI+)

$^1$H-NMR (400 MHz, D$_6$-DMSO): δ=1.49 (quintet, 2H, CH$_2$—CH$_2$—Ar), 1.81 (quintet, 2H, CH$_2$—CH$_2$-triazole), 2.54 (t, 2H, CH$_2$—Ar), 2.61 (s, 3H, CH$_3$), 4.39 (t, 2H, CH$_2$-triazole), 5.16 (s, 2H, OCH$_2$), 6.98 (d, 2H, OAr), 7.11 (s, 2H, OAr), 7.71 (s, 1H, triazole), 7.74 (t, 1H, 5-H—Ar—CF$_3$), 7.80 (d, 1H, 4-H—Ar—CF$_3$), 7.90 (d, 1H, pyridine), 7.95 (d, 1H, pyridine), 8.11 (s, 1H, triazole), 8.39 (d, 1H, 6-H—Ar—CF$_3$), 8.42 (s, 1H, 2-H—Ar—CF$_3$).

Example 13

2-Methyl-3-[3-Methyl-4-(4-[1,2,3]triazol-1-yl-butyl)-phenoxymethyl]-6-(3-trifluoromethyl-phenyl)-pyridine 30 mg (0.74 mmol) of 60% sodium hydride were added to at 0° C. to a solution of 162 mg (0.70 mmol) 3-methyl-4-(4-[1,2,3]triazol-1-yl-butyl)-phenol in 8.0 ml N,N-dimethylformamide and stirred for 30 min. at 0° C. 200 mg (0.70 mmol) 3-chloromethyl-2-methyl-6-(3-trifluoromethyl-phenyl)-pyridine were given to the reaction mixture and stirring continued at room temperature (r.t.) overnight. After addition of 16 ml water the mixture was stirred for 1 h, the formed precipitate isolated by filtration, washed with water, n-heptane, and ether. The residue was dried at 40° C. in vacuum to give 255 mg (76%) of the title compound as slightly pink powder.

MS: 481.3 (ESI+)

$^1$H-NMR (400 MHz, D$_6$-DMSO): δ=1.43 (quintet, 2H, CH$_2$—CH$_2$—Ar), 1.86 (quintet, 2H, CH$_2$—CH$_2$-triazole), 2.22 (s, 3H, CH$_3$), 2.53 (t, 2H, CH$_2$—Ar), 2.61 (s, 3H, CH$_3$), 4.41 (t, 2H, CH$_2$-triazole), 5.14 (s, 2H, OCH$_2$), 6.81 (d, 1H, 6-H—OAr), 6.87 (s, 1H, 2-H—OAr), 7.02 (d, 1H, 5-H—OAr), 7.71 (s, 1H, triazole), 7.73 (t, 1H, 5-H—Ar—CF$_3$), 7.80 (d, 1H, 4-H—Ar—CF$_3$), 7.90 (d, 1H, pyridine), 7.95 (d, 1H, pyridine), 8.12 (s, 1H, triazole), 8.39 (d, 1H, 6-H—Ar—CF$_3$), 8.43 (s, 1H, 2-H—Ar—CF$_3$).

Example 14

2-Methyl-3-[4-(4-[1,2,3]triazol-1-yl-butyl)-phenoxymethyl]-6-(3-trifluoromethoxy-phenyl)-pyridine 17 mg (0.42 mmol) of 60% sodium hydride were added to at 0° C. to a solution of 87 mg (0.40 mmol) 4-(4-[1,2,3]triazol-1-yl-butyl)-phenol in 6.0 ml N,N-dimethylformamide and stirred for 30 min. at 0° C. 120 mg (0.40 mmol) 3-chloromethyl-2-methyl-6-(3-trifluoromethoxy-phenyl)-pyridine were given to the reaction mixture and stirring continued at room temperature (r.t.) overnight. After addition of 12 ml water the mixture was stirred for 1 h, the formed precipitate isolated by filtration, washed with water, water/methanol 1:1, n-heptane, and ether. The residue was dried at 40° C. in vacuum to give 138 mg (71%) of the title compound as almost colorless powder.

MS: 483.3 (ESI+)

$^1$H-NMR (400 MHz, D$_6$-DMSO): δ=1.48 (quintet, 2H, CH$_2$—CH$_2$—Ar), 1.81 (quintet, 2H, CH$_2$—CH$_2$-triazole), 2.54 (t, 2H, CH$_2$—Ar), 2.60 (s, 3H, CH$_3$), 4.39 (t, 2H, CH$_2$-triazole), 5.16 (s, 2H, OCH$_2$), 6.98 (d, 2H, OAr), 7.11 (s, 2H, OAr), 7.43 (d, 1H, 4-H—Ar—OCF$_3$), 7.63 (t, 1H, 5-H—Ar—CF$_3$), 7.70 (s, 1H, triazole), 7.90 (s, 2H, pyridine), 8.06 (s, 1H, 2-H—Ar—OCF$_3$), 8.11 (s, 1H, triazole), 8.12 (d, 1H, 6-H—Ar—OCF$_3$).

Example 15

2-Methyl-3-[3-Methyl-4-(4-[1,2,3]triazol-1-yl-butyl)-phenoxymethyl]-6-(3-trifluoromethoxy-phenyl)-pyridine 28 mg (0.69 mmol) of 60% sodium hydride were added to at 0° C. to a solution of 153 mg (0.66 mmol) 3-methyl-4-(4-[1,2,3]triazol-1-yl-butyl)-phenol in 6.0 ml N,N-dimethylformamide and stirred for 30 min. at 0° C. 200 mg (0.66 mmol) 3-chloromethyl-2-methyl-6-(3-trifluoromethoxy-phenyl)-pyridine were given to the reaction mixture and stirring continued at room temperature (r.t.) overnight. After addition of 16 ml water the mixture was stirred for 1 h, the formed precipitate isolated by filtration, washed with water, n-heptane, and ether. The residue was dried at 40° C. in vacuum to give 234 mg (72%) of the title compound as slightly yellow powder.

MS: 497.3 (ESI+)

$^1$H-NMR (400 MHz, D$_6$-DMSO): δ=1.43 (quintet, 2H, CH$_2$—CH$_2$—Ar), 1.86 (quintet, 2H, CH$_2$—CH$_2$-triazole), 2.21 (s, 3H, CH$_3$), 2.52 (t, 2H, CH$_2$—Ar), 2.59 (s, 3H, CH$_3$), 4.41 (t, 2H, CH$_2$-triazole), 5.13 (s, 2H, OCH$_2$), 6.81 (d, 1H, 6-H—OAr), 6.86 (s, 1H, 2-H—OAr), 7.02 (d, 1H, 5-H—OAr), 7.43 (d, 1H, 4-H—Ar—OCF$_3$), 7.63 (t, 1H, 5-H—Ar—CF$_3$), 7.70 (s, 1H, triazole), 7.89 (m, 2H, pyridine), 8.06 (s, 1H, 2-H—Ar—OCF$_3$), 8.11 (s, 1H, triazole), 8.12 (d, 1H, 6-H—Ar—OCF$_3$).

Example 16

6-(4-Fluoro-phenyl)-2-methyl-3-[4-(4-[1,2,3]triazol-1-yl-butyl)-phenoxymethyl]-pyridine i) [6-(4-Fluor-phenyl)-2-methyl-pyridin-3-yl]-methanol 4.67 g (123 mmol) lithium aluminium hydride was suspended in 220 ml tetrahydrofuran (THF) and stirred for 20 min. at room temperature. The mixture was cooled to 0° C. and a solution of 15.95 g (61.5 mmol) 6-(4-Fluoro-phenyl)-2-methyl-nicotinic acid ethyl ester (WO 03/068749) in 100 ml added within 15 min. at the same temperature. The mixture was stirred overnight at room temperature (r.t.) and cooled to 0° C. 200 ml of saturated sodium chloride solution were added drop by drop and stirring continued for 60 min. Concentrated HCl was added carefully to adjust the pH to 5. Precipitated salts were filtered off and washed with THF. The combined THF-solutions were evaporated and the residue extracted twice with ethyl acetate. The organic phase was dried (sodium sulphate) and evaporated. The orange resin crystallized after a short time, was stirred with ethyl acetate/n-heptane 1:3, isolated by filtration, washed with tert-butylmethyl ether and dried. The combined mother liquor from the washings was evaporated and the crystalline precipitate treated as above. The combined yield was 9.25 g (69%) of pale yellow powder.

MS: 218.2 (ESI+).

$^1$H-NMR (400 MHz, D$_6$-DMSO): δ=2.50 (s, 3H, CH$_3$), 4.39 (s, 2H, CH$_2$—OH), 5.27 (s, 1H, OH), 7.29 (t, 2H, Ar—F), 7.77 (m, 2H, pyridine), 8.12 (t, 2H, Ar—F).

ii) 3-Chloromethyl-6-(4-fluoro-phenyl)-2-methyl-pyridine 10.1 g (6.2 ml, 85 mmol) thionyl chloride is added drop by drop within 15 min. at 0° C. to a solution of 0.2 ml N,N-dimethylformamide (DMF) and 9.24 g (42.5 mmol) [6-(4-Fluor-phenyl)-2-methyl-pyridin-3-yl]-methanol, and stirred for 3 h at room temperature (r.t.) The mixture is poured on ice/sodium bicarbonate solution, the organic phase separated, washed with water, dried (sodium sulphate), and evaporated. 9.78 g (97%) of the title compound were obtained.

MS: 236.1 (ESI+).

$^1$H-NMR (400 MHz, D$_6$-DMSO): δ=2.63 (s, 3H, CH$_3$), 4.88 (s, 2H, CH$_2$—Cl), 5.27 (s, 1H, OH), 7.31 (t, 2H, Ar—F), 7.80 (d, 1H, pyridine), 7.87 (d, 1H, pyridine), 8.14 (t, 2H, Ar—F).

iii) 6-(4-Fluoro-phenyl)-2-methyl-3-[4-(4-[1,2,3]triazol-1-yl-butyl)-phenoxymethyl]-pyridine 36 mg (0.89 mmol) of 60% sodium hydride were added to at 0° C. to a solution of 185 mg (0.85 mmol) 4-(4-[1,2,3]triazol-1-yl-butyl)-phenol in 8.0 ml N,N-dimethylformamide and stirred for 30 min. at 0° C. 200 mg (0.85 mmol) 3-chloromethyl-6-(4-fluoro-phenyl)-2-methyl-pyridine were given to the reaction mixture and stirring continued at room temperature (r.t.) overnight. After addition of 16 ml water the mixture was stirred for 1 h, the formed precipitate isolated by filtration, washed with water, water/methanol 1:1, and ether. The residue was dried at 40° C. in vacuum to give 295 mg (83%) of the title compound as white powder.

MS: 417.4 (ESI+)

$^1$H-NMR (400 MHz, D$_6$-DMSO): δ=1.48 (quintet, 2H, CH$_2$—CH$_2$—Ar), 1.81 (quintet, 2H, CH$_2$—CH$_2$-triazole), 2.54 (t, 2H, CH$_2$—Ar), 2.58 (s, 3H, CH$_3$), 4.39 (t, 2H, CH$_2$-triazole), 5.13 (s, 2H, OCH$_2$), 6.97 (d, 2H, OAr), 7.11 (s, 2H, OAr), 7.31 (t, 2H, Ar—F), 7.70 (s, 1H, triazole), 7.79 (d, 1H, pyridine), 7.85 (d, 1H, pyridine), 8.11 (s, 1H, triazole), 8.14 (t, 2H, Ar—F).

Example 17

6-(4-Fluoro-phenyl)-2-methyl-3-[3-Methyl-4-(4-[1,2,3]triazol-1-yl-butyl)-phenoxymethyl]-pyridine 36 mg (0.89 mmol) of 60% sodium hydride were added to at 0° C. to a solution of 197 mg (0.85 mmol) 3-methyl-4-(4-[1,2,3]triazol-1-yl-butyl)-phenol in 8.0 ml N,N-dimethylformamide and stirred for 30 min. at 0° C. 200 mg (0.85 mmol) 3-chloromethyl-6-(4-fluoro-phenyl)-2-methyl-pyridine were given to the reaction mixture and stirring continued at room temperature (r.t.) overnight. After addition of 16 ml water the mixture was stirred for 1 h, the formed precipitate isolated by filtration, washed with water, water/methanol 1:1, and ether. 325 mg (89%) of the title compound were obtained as pale beige powder.

MS: 431.4 (ESI+).

$^1$H-NMR (500 MHz, D$_6$-DMSO): δ=1.43 (quintet, 2H, CH$_2$—CH$_2$—Ar), 1.86 (quintet, 2H, CH$_2$—CH$_2$-triazole), 2.21 (s, 3H, OArCH$_3$), 2.53 (t, 2H, CH$_2$—Ar), 2.57 (s, 3H, pyridine-CH$_3$), 4.41 (t, 2H, CH$_2$-triazole), 5.11 (s, 2H, OCH$_2$), 6.80 (d, 1H, 6-H—OAr), 6.86 (s, 1H, 2-H—OAr), 7.02 (d, 1H, 5-H—OAr), 7.31 (t, 1H, Ar—F), 7.71 (s, 1H, triazole), 7.79 (d, 1H, pyridine), 7.84 (d, 1H, pyridine), 8.12 (s, 1H, triazole), 8.15 (t, 1H, Ar—CF$_3$).

Example 18

2-[4-(4-[1,2,3]triazol-1-yl-butyl)-phenoxymethyl]-6-(4-trifluoromethyl-phenyl)-pyridine 16 mg (0.39 mmol) of 60% sodium hydride were added at 0° C. to a solution of 80 mg (0.37 mmol) 4-(4-[1,2,3]triazol-1-yl-butyl)-phenol in 4.0 ml N,N-dimethylformamide and stirred for 30 min. at 0° C. 100 mg (0.37 mmol) 2-chloromethyl-6-(4-trifluoromethyl-phenyl)-pyridine (WO 2004/007439) were given to the reaction mixture and stirring continued at r.t for 2 days. After addition of 8 ml water the mixture was stirred for 1 h, the formed precipitate isolated by filtration, washed with water, methanol/water 1:1, and a small amount of ether. The residue was dried at 40° C. to give 101 mg (60%) of the title compound as white powder.

MS: 453.4 (ESI+)

$^1$H-NMR (400 MHz, D$_6$-DMSO): δ=1.48 (quintet, 2H, CH$_2$—CH$_2$—Ar), 1.81 (quintet, 2H, CH$_2$—CH$_2$-triazole), 2.53 (t, 2H, CH$_2$—Ar), 4.39 (t, 2H, CH$_2$-triazole), 5.24 (s, 2H, OCH$_2$), 6.97 (d, 2H, OAr), 7.10 (d, 2H, OAr), 7.54 (d, 1H, pyridine), 7.70 (s, 1H, triazole), 7.87 (d, 2H, Ar—CF$_3$), 7.98 (d, 1H, pyridine), 8.02 (d, 1H, pyridine), 8.10 (s, 1H, triazole), 8.32 (d, 2H, Ar—CF$_3$).

Example 19

2-[3-Methyl-4-(4-[1,2,3]triazol-1-yl-butyl)-phenoxymethyl]-6-(4-trifluoromethyl-phenyl)-pyridine 16 mg (0.39 mmol) of 95% sodium hydride were added at 0° C. to a solution of 86 mg (0.37 mmol) 3-methyl-4-(4-[1,2,3]triazol-1-yl-butyl)-phenol in 4.0 ml N,N-dimethylformamide and stirred for 30 min. at 0° C. 100 mg (0.37 mmol) 2-chloromethyl-6-(4-trifluoromethyl-phenyl)-pyridine were given to the reaction mixture and stirring continued at r.t overnight. After addition of 8 ml water the mixture was stirred for 1 h, the formed precipitate isolated by filtration, washed with water, methanol/water 1:1, and a small amount of ether. The residue was dried at 40° C. to give 145 mg (84%) of the title compound as white powder.

MS: 467.4 (ESI+)

$^1$H-NMR (400 MHz, D$_6$-DMSO): δ=1.42 (quintet, 2H, CH$_2$—CH$_2$—Ar), 1.85 (quintet, 2H, CH$_2$—CH$_2$-triazole), 2.20 (s, 3H, CH$_3$), 2.53 (t, 2H, CH$_2$—Ar), 4.40 (t, 2H, CH$_2$-triazole), 5.23 (s, 2H, OCH$_2$), 6.79 (d, 1H, 6-H—OAr), 6.87 (s, 1H, 2-H—OAr), 7.01 (d, 1H, 5-H—OAr), 7.54 (d, 1H, pyridine), 7.70 (s, 1H, triazole), 7.87 (d, 2H, Ar—CF$_3$), 7.98 (d, 1H, pyridine), 8.01 (d, 1H, pyridine), 8.11 (s, 1H, triazole), 8.32 (d, 2H, Ar—CF$_3$).

Example 20

6-(4-Chloro-phenyl)-2-methyl-3-[4-(4-[1,2,3]triazol-1-yl-butyl)-phenoxymethyl]-pyridine 33 mg (0.83 mmol) of 60% sodium hydride were added to at 0° C. to a solution of 172 mg (0.85 mmol) 4-(4-[1,2,3]triazol-1-yl-butyl)-phenol in 8.0 ml N,N-dimethylformamide and stirred for 30 min. at 0° C. 200 mg (0.85 mmol) 3-chloromethyl-6-(4-chloro-phenyl)-2-methyl-pyridine (EP 0 284 174) were given to the reaction mixture and stirring continued at room temperature (r.t.) overnight. After addition of 16 ml water the mixture was stirred for 1 h, the formed precipitate isolated by filtration, washed with water, water/methanol 1:1, and ether. The residue was dried at 40° C. in vacuum to give 305 mg (89%) of the title compound as white powder.

MS: 433.4 (ESI+).

$^1$H-NMR (400 MHz, D$_6$-DMSO): δ=1.48 (quintet, 2H, CH$_2$—CH$_2$—Ar), 1.81 (quintet, 2H, CH$_2$—CH$_2$-triazole), 2.54 (t, 2H, CH$_2$—Ar), 2.58 (s, 3H, CH$_3$), 4.39 (t, 2H, CH$_2$-triazole), 5.13 (s, 2H, OCH$_2$), 6.97 (d, 2H, OAr), 7.11 (s, 2H, OAr), 7.54 (d, 2H, Ar—Cl), 7.71 (s, 1H, triazole), 7.82 (d, 1H, pyridine), 7.86 (d, 1H, pyridine), 8.11 (s, 1H, triazole), 8.12 (d, 2H, Ar—Cl).

Example 21

6-(4-Chloro-phenyl)-2-methyl-3-[3-Methyl-4-(4-[1,2,3]triazol-1-yl-butyl)-phenoxymethyl]-pyridine 33 mg (0.83 mmol) of 60% sodium hydride were added to at 0° C. to a solution of 172 mg (0.79 mmol) 3-methyl-4-(4-[1,2,3]triazol-1-yl-butyl)-phenol in 8.0 ml N,N-dimethylformamide and stirred for 30 min. at 0° C. 200 mg (0.79 mmol) 3-chloromethyl-6-(4-chloro-phenyl)-2-methyl-pyridine were given to the reaction mixture and stirring continued at room temperature (r.t.) overnight. After addition of 16 ml water the mixture was stirred for 1 h, the formed precipitate isolated by filtration, washed with water, water/methanol 1:1, ethyl acetate, and ether. 324 mg (91%) of the title compound were obtained as slightly beige powder.

MS: 447.4 (ESI+).
$^1$H-NMR (500 MHz, D$_6$-DMSO): δ=1.43 (quintet, 2H, CH$_2$—CH$_2$—Ar), 1.86 (quintet, 2H, CH$_2$—CH$_2$-triazole), 2.21 (s, 3H, OArCH$_3$), 2.53 (t, 2H, CH$_2$—Ar), 2.58 (s, 3H, pyridine-CH$_3$), 4.41 (t, 2H, CH$_2$-triazole), 5.11 (s, 2H, OCH$_2$), 6.80 (d, 1H, 6-H—OAr), 6.86 (s, 1H, 2-H—OAr), 7.02 (d, 1H, 5-H—OAr), 7.54 (d, 2H, Ar—Cl), 7.71 (s, 1H, triazole), 7.84 (m, 2H, pyridine), 8.12 (m, 3H, triazole, Ar—Cl).

Example 22

2-Methyl-3-[4-(2-[1,2,3]triazol-1-yl-ethylsulfanylmethyl)-phenoxymethyl]-6-(4-trifluoromethyl-phenyl)-pyridine Preparation of 4-(2-[1,2,3]Triazol-1-yl-ethanesulfanylmethyl)-phenol A solution of 300 mg (1.09 mmol) of 1-[2-(4-Allyloxy-benzylsulfanyl-ethyl)-1H-[1,2,3]triazole [Example 9 iii)] in 6 ml dichloromethane was added to a solution of 0.511 g (3.27 mmol) 1,3-dimethylbarbituric acid and 35 mg (0.03 mmol) Pd(PPh$_3$)$_4$ in 12 ml dichloromethane and stirred for 5 h at 50° C. The mixture was extracted with 3×12 ml sat. NaHCO$_3$-solution and 10 ml water. The aqueous phase was extracted twice with 20 ml dichloromethane and the organic extracts were combined and dried over Na$_2$SO$_4$. After evaporation the residue was purified by chromatography on silica gel (ethyl acetate/n-heptane 5:1) to yield 0.154 g (60%) of 4-(2-[1,2,3]Triazol-1-yl-ethanesulfanylmethyl)-phenol.

MS: 236.3 (ESI+)
$^1$H-NMR (400 Hz, [D$_6$]DMSO): δ=2.88 (t, 2H, CH$_2$—CH$_2$-triazole), 3.60 (s, 2H SCH$_2$Ph), 4.53 (t, 2H, CH$_2$-triazole), 6.70 (d, 2H, 2'-/6'H), 7.10 (d, 2H, 3'-/5'H), 7.72 (s, 1H, triazole), 8.11 (s, 1H, triazole), 9.35 (s, 1H, OH).

Preparation of 2-Methyl-3-[4-(2-[1,2,3]triazol-1-yl-ethylsulfanylmethyl)-phenoxymethl]-6-(4-trifluoromethyl-phenyl)-pyridine A solution of 150 mg (0.64 mmol) 4-(2-[1,2,3]Triazol-1-yl-ethanesulfanyl-methyl)-phenol in 6.0 ml N,N-dimethylformamide was treated at 0° C. with 27 mg (0.67 mmol) of 60% sodium hydride and stirred at 0° C. for 30 min. Then 183 mg (0.64 mmol) 3-chloromethyl-2-methyl-6-(trifluoromethyl-phenyl)-pyridine were added and stirred continued over night. After addition of 12 ml water, the precipitate was isolated, washed thoroughly with water, methanol/water 1:1, ethyl acetate/n-heptane 1:3 and ether. The residue was dried at 40° C. to give 251 mg (81%) of the title compound as white powder.

MS: 485.4 (ESI+)
$^1$H-NMR (400 Hz, [D$_6$]DMSO): δ=2.61 (s, 3H, CH$_3$), 2.88 (t, 2H, CH$_2$—CH$_2$-triazole), 3.67 (s, 2H CH$_2$—Ar), 4.56 (t, 2H, CH$_2$-triazole), 5.19 (s, 2H, OCH$_2$), 7.04 (d, 2H, OAr), 7.27 (d, 2H, OAr), 7.73 (s, 1H, triazole), 7.85 (d, 2H, Ar—CF$_3$), 7.92 (s, 2H, pyridine), 8.13 (s, 1H, triazole), 8.31 (d, 2H, Ar—CF$_3$).

Example 23

6-(4-Fluoro-phenyl)-2-methyl-3-[4-(2-[1,2,3]triazol-1-yl-ethylsulfanylmethyl)-phenoxymethyl]-pyridine A solution of 200 mg (0.85 mmol) 4-(2-[1,2,3]Triazol-1-yl-ethanesulfanyl-methyl)-phenol (Example 22) in 8.0 ml N,N-dimethylformamide was treated at 0° C. with 36 mg (0.89 mmol) of 60% sodium hydride and stirred at 0° C. for 30 min. Then 200 mg (0.85 mmol) 3-chloromethyl-6-(4-fluoro-phenyl)-2-methyl-pyridine (Example 16 ii) were added and stirred continued over night. After addition of 12 ml water, the precipitate was isolated, washed thoroughly with water, methanol/water 1:1 and ether. The residue was dried at 40° C. to give 320 mg (87%) of the title compound as white powder.

MS: 435.3 (ESI+)
$^1$H-NMR (400 Hz, [D$_6$]DMSO): δ=2.58 (s, 3H, CH$_3$), 2.87 (t, 2H, CH$_2$—CH$_2$-triazole), 3.67 (s, 2H CH$_2$—Ar), 4.55 (t, 2H, CH$_2$-triazole), 5.16 (s, 2H, OCH$_2$), 7.02 (d, 2H, OAr), 7.26 (d, 2H, OAr), 7.31 (t, 2H, Ar—F), 7.73 (s, 1H, triazole), 7.79 (d, 1H, pyridine), 7.86 (d, 1H, pyridine), 8.14 (t, 2H, Ar—F), 8.14 (s, 1H, triazole).

Example 24

6-(4-Chloro-phenyl)-2-methyl-3-[4-(2-[1,2,3]triazol-1-yl-ethylsulfanylmethyl)-phenoxymethyl]-pyridine A solution of 200 mg (0.85 mmol) 4-(2-[1,2,3]Triazol-1-yl-ethanesulfanyl-methyl)-phenol (Example 22) in 8.0 ml N,N-dimethylformamide was treated at 0° C. with 36 mg (0.89 mmol) of 60% sodium hydride and stirred at 0° C. for 30 min. Then 214 mg (0.85 mmol) 3-chloromethyl-6-(4-chloro-phenyl)-2-methyl-pyridine (EP 0 284 174) were added and stirred continued over night. After addition of 12 ml water, the precipitate was isolated, washed thoroughly with water, methanol/water 1:1 and ether. The residue was dried at 40° C. to give 340 mg (89%) of the title compound as white powder.

MS: 451.3 (ESI+)
$^1$H-NMR (400 Hz, [D$_6$]DMSO): δ=2.58 (s, 3H, CH$_3$), 2.87 (t, 2H, CH$_2$—CH$_2$-triazole), 3.67 (s, 2H CH$_2$—Ar), 4.55 (t, 2H, CH$_2$-triazole), 5.17 (s, 2H, OCH$_2$), 7.03 (d, 2H, OAr), 7.26 (d, 2H, OAr), 7.54 (d, 2H, Ar—Cl), 7.73 (s, 1H, triazole), 7.82 (d, 1H, pyridine), 7.87 (d, 1H, pyridine), 8.12 (d, 2H, Ar—F), 8.12 (s, 1H, triazole).

Example 25

5-[4-(4-[1,2,3]Triazol-1-yl-butyl)-phenoxymethyl]-2-(3-trifluoromethyl-phenyl)-pyridine Preparation of 5-Chloromethyl-2-(3-trifluoromethyl-phenyl)-pyridine i) 6-(3-Trifluoromethyl-phenyl)-pyridine-3-carbaldehyde 1.44 g (1.25 mmol)Pd(PPh$_3$)$_4$ was added under argon at room temperature to a solution of 6-bromo-pyridine-3-carbaldehyde in 60 ml 1,2 dimethoxyethane and stirred for 15 min. 63 ml (125 mmol) of 2 M sodium carbonate solution and 2.5 g (13.16 mmol) of 3-(trifluoromethyl-)-phenylboronic acid were added and the mixture heated to boiling temperature for 18 hours (h). The reaction mixture was cooled to room temperature, filtered, and the filtrate evaporated. The residue was taken up with ethyl acetate, washed twice with water, dried over sodium sulphate and evaporated. Chromatography on silica (eluent: ethyl acetate/n-heptane 1:3) gave 1.18 g (36%) of 6-(3-Trifluoromethyl-phenyl)-pyridine-3-carbaldehyde

MS: 252.1 (ESI+)

$^1$H-NMR (400 Hz, [D$_6$]DMSO): δ=7.86 (t, 1H, Ar—CF$_3$), 7.95 (d, 1H, Ar—CF$_3$), 8.43 (t, 2H, pyridine), 8.57 (d, 1H, Ar—CF$_3$), 8.57 (s, 1H, Ar—CF$_3$), 9.26 (s, 1H, pyridine), 10.23 (s, 1H, CHO), ii) [6-(3-Trifluoromethyl-phenyl)-pyridine-3-yl]-methanol 261 mg (6.87 mmol) lithium aluminium hydride were given to 20 ml tetrahydrofuran (THF) and stirred at room temperature (r.t.) for 20 min. A solution of 1.15 g (4.58 mmol) 6-(3-Trifluoromethyl-phenyl)-pyridine-3-carbaldehyde in 20 ml THF was added drop by drop within 15 min., and the mixture stirred for 3 h. 1.5 ml ice water and 0.6 ml 2 M NaOH were added slowly at 0° C. and stirred continued for 30 min. A formed salt precipitate was isolated by filtration and washed with THF. The combined THF-solutions were evaporated, the residue extracted twice with ethyl acetate, the organic phase dried (sodium sulphate), evaporated, and the obtained material (0.98 g, 85%) used without further purification.

MS: 254.0 (ESI+)

iii) 5-Chloromethyl-2-(3-trifluoromethyl-phenyl)-pyridine 911 mg (0.56 ml, 7.66 mmol) thionyl chloride were added drop by drop at 0° C. to a solution of 0.2 ml N,N-dimethylformamide (DMF) and 970 mg (3.83 mmol) [6-(3-Trifluoromethyl-phenyl)-pyridine-3-yl]-methanol in 30 ml dichloromethane, stirred for 5 min. at 0° C., and at r.t. for 1 h. The mixture is poured on ice/sodium bicarbonate solution and the organic phase separated. The water phase is extracted with dichloromethane. The combined organic phases were washed with water, dried (sodium sulphate), and evaporated. Purification by chromatography on silica (eluent: ethyl acetate/n-heptane 1:3) gave 750 mg (72%) of 5-Chloromethyl-2-(3-trifluoromethyl-phenyl)-pyridine as light yellow crystals

MS: 272.1 (ESI+)

$^1$H-NMR (400 Hz, [D$_6$]DMSO): δ=4.90 (s, 2H, CH$_2$-pyridine), 7.75 (t, 1H, Ar—CF$_3$), 7.82 (d, 1H, Ar—CF$_3$), 8.01 (d, 1H, pyridine), 8.15 (d, 1H, pyridine), 8.42 (d, 1H, Ar—CF$_3$), 8.42 (s, 1H, Ar—CF$_3$), 9.26 (s, 1H, pyridine), 10.23 (s, 1H, CHO), Preparation of 5-[4-(4-[1,2,3]Triazol-1-yl-butyl)-phenoxymethyl]-2-(3-trifluoromethyl-phenyl)-pyridine A solution of 100 mg (0.46 mmol) 4-(4-[1,2,3]triazol-1-yl-butyl)phenol in 4.0 ml N,N-dimethylformamide was treated at 0° C. with 19 mg (0.48 mmol) of 60% sodium hydride and stirred at 0° C. for 30 min. Then 125 mg (0.46 mmol) 5-Chloromethyl-2-(3-trifluoromethyl-phenyl)-pyridine were added and stirred continued at r.t. over night. After addition of 8 ml water, the precipitate was isolated, washed thoroughly with water, methanol/water 1:1 and diisopropylether. The residue was dried at 40° C. to give 170 mg (82%) of the title compound as white powder.

MS: 453.4 (ESI+)

$^1$H-NMR (400 Hz, [D$_6$]DMSO): δ=1.48 (quintet, 2H, CH$_2$—CH$_2$—Ar), 1.80 (quintet, 2H, CH$_2$—CH$_2$-triazole), 2.53 (t, 2H, CH$_2$—Ar), 4.38 (t, 2H, CH$_2$-triazole), 5.18 (s, 2H, OCH$_2$), 6.96 (d, 2H, OAr), 7.10 (d, 2H, OAr), 7.70 (s, 1H, triazole), 7.75 (t, 1H Ar—CF$_3$) 7.81 (d, 1H, Ar—CF$_3$), 7.99 (d, 1H, pyridine), 8.10 (s, 1H, triazole), 8.14 (d, 1H, pyridine), 8.42 (d, 1H Ar—CF$_3$), 8.43 (s, 1H Ar—CF$_3$), 8.79 (s, 1H, 6-H-pyridine).

Example 26

5-[3-Methyl-4-(4-[1,2,3]triazol-1-yl-butyl)-phenoxymethyl]-2-(3-trifluoromethyl-phenyl)-pyridine A solution of 100 mg (0.43 mmol) 3-methyl-4-(4-[1,2,3]triazol-1-yl-butyl)phenol in 4.0 ml N,N-dimethylformamide was treated at 0° C. with 18 mg (0.45 mmol) of 60% sodium hydride and stirred at 0° C. for 30 min. Then 117 mg (0.43 mmol) 5-Chloromethyl-2-(3-trifluoromethyl-phenyl)-pyridine were added and stirred continued at r.t. over night. After addition of 8 ml water, the precipitate was isolated, washed thoroughly with water, methanol/water 1:1 and diisopropylether. The residue was dried at 40° C. to give 160 mg (79%) of the title compound as white powder.

MS: 467.4 (ESI+)

$^1$H-NMR (400 Hz, [D$_6$]DMSO): δ=1.43 (quintet, 2H, CH$_2$—CH$_2$—Ar), 1.85 (quintet, 2H, CH$_2$—CH$_2$-triazole), 2.21 (s, 3H, CH$_3$), 2.52 (t, 2H, CH$_2$—Ar), 4.40 (t, 2H, CH$_2$-triazole), 5.17 (s, 2H, OCH$_2$), 6.78 (d, 1H, OAr), 6.85 (s, 1H, OAr), 7.01 (d, 1H, OAr), 7.70 (s, 1H, triazole), 7.74 (t, 2H, Ar—CF3), 7.81 (d, 1H Ar—CF$_3$), 7.99 (d, 1H, pyridine), 8.12 (s, 1H, triazole), 8.12 (d, 1H, pyridine), 8.41 (d, 1H Ar—CF$_3$), 8.41 (s, 1H Ar—CF$_3$), 8.78 (s, 1H, 6-H-pyridine).

Example 27

2-(4-Chloro-phenyl)-5-[4-(4-[1,2,3]triazol-1-yl-butyl)-phenoxymethyl]-pyridine

A solution of 91 mg (0.42 mmol) 4-(4-[1,2,3]triazol-1-yl-butyl)phenol in 4.0 ml N,N-dimethylformamide was treated at 0° C. with 18 mg (0.44 mmol) of 60% sodium hydride and stirred at 0° C. for 30 min. Then 100 mg (0.42 mmol) 5-Chloromethyl-2-(4-chloro-phenyl)-pyridine (GB 1147068) were added and stirred continued over night. After addition of 8 ml water, the precipitate was isolated, washed thoroughly with water, methanol/water 1:1 and diisopropylether. The residue was dried at 40° C. to give 121 mg (69%) of the title compound as light brown powder.

MS: 419.3 (ESI+)

$^1$H-NMR (400 Hz, [D$_6$]DMSO): δ=1.48 (quintet, 2H, CH$_2$—CH$_2$—Ar), 1.80 (quintet, 2H, CH$_2$—CH$_2$-triazole), 2.53 (t, 2H, CH$_2$—Ar), 4.39 (t, 2H, CH$_2$-triazole), 5.16 (s, 2H, OCH$_2$), 6.95 (d, 2H, OAr), 7.10 (d, 2H, OAr), 7.56 (d, 2H, Ar—Cl), 7.70 (s, 1H, triazole), 7.95 (d, 1H, pyridine), 8.01 (d, 1H, pyridine), 8.11 (d, 4H, Ar—Cl), 8.11 (s, 1H, triazole), 8.73 (1H, 6-H-pyridine).

Example 28

2-(4-Chloro-phenyl)-5-[3-methyl-4-(4-[1,2,3]triazol-1-yl-butyl)-phenoxymethyl]-pyridine A solution of 97 mg (0.42 mmol) 3-methyl-4-(4-[1,2,3]triazol-1-yl-butyl)phenol in 4.0 ml N,N-dimethylformamide was treated at 0° C. with 18 mg (0.44 mmol) of 60% sodium hydride and stirred at 0° C. for 30 min. Then 100 mg (0.42 mmol) 5-Chloromethyl-2-(4-chloro-phenyl)-pyridine (GB 1147068) were added and stirred continued over night. After addition of 8 ml water, the precipitate was isolated, washed thoroughly with water, methanol/water 1:1 and diisopropylether. The residue was dried at 40° C. to give 133 mg (73%) of the title compound as light brown powder.

MS: 433.3 (ESI+)

$^1$H-NMR (400 Hz, [$D_6$]DMSO): δ=1.42 (quintet, 2H, $\underline{CH_2}$—$CH_2$—Ar), 1.85 (quintet, 2H, $\underline{CH_1}$—$CH_2$-triazole), 2.20 (s, 3H, $CH_3$), 2.51 (t, 2H, $\underline{CH_2}$—Ar), 4.40 (t, 2H, $CH_2$-triazole), 5.14 (s, 2H, $OCH_2$), 6.78 (d, 1H, OAr), 6.83 (s, 1H, OAr), 7.01 (d, 2H, OAr), 7.55 (d, 2H, Ar—Cl), 7.70 (s, 1H, triazole), 7.94 (d, 1H, pyridine), 8.01 (d, 1H, pyridine), 8.11 (d, 4H, Ar—Cl), 8.11 (s, 1H, triazole), 8.73 (1H, 6-H-pyridine).

Example 29

2-(4-Chloro-phenyl)-5-[4-(2-[1,2,3]triazol-1-yl-ethylsulfanylmethyl)-phenoxymethyl]-pyridine A solution of 99 mg (0.42 mmol) 4-(2-[1,2,3]Triazol-1-yl-ethanesulfanyl-methyl)-phenol in 4.0 ml N,N-dimethylformamide was treated at 0° C. with 18 mg (0.44 mmol) of 60% sodium hydride and stirred at 0° C. for 30 min. Then 100 mg (0.42 mmol) 5-Chloromethyl-2-(4-chloro-phenyl)-pyridine were added and stirred continued over night. After addition of 8 ml water, the precipitate was isolated, washed thoroughly with water, methanol/water 1:1 and diisopropylether. The residue was dried at 40° C. to give 145 mg (79%) of the title compound as white powder.

MS: 437.1 (ESI+)

$^1$H-NMR (400 Hz, [$D_6$]DMSO): δ=2.86 (t, 2H, $CH_2$—$CH_2$-triazole), 3.66 (s, 2H $CH_2$—Ar), 4.55 (t, 2H, $CH_2$-triazole), 5.19 (s, 2H, $OCH_2$), 7.01 (d, 2H, OAr), 7.26 (d, 2H, OAr), 7.56 (d, 2H, Ar—Cl), 7.72 (s, 1H, triazole), 7.96 (d, 1H, pyridine), 8.01 (d, 1H, pyridine), 8.12 (d, 4H, Ar—Cl), 8.1 (s, 1H, triazole), 8.75 (1H, 6-H-pyridine).

Example 30

2-[3-Methyl-4-(4-[1,2,3]triazol-1-yl-butyl)-phenoxymethyl]-6-(4-trifluoromethoxy-phenyl)-pyridine

Preparation of 2-Chloromethyl-6-(4-trifluoromethoxy-phenyl)-pyridine i) 6-(4-Trifluoromethoxy-phenyl)-pyridine-2-carboxylic acid methyl ester 162 mg (0.14 mmol)Pd(PPh$_3$)$_4$ was added under argon at room temperature to a solution of 2.0 g (9.25 mmol) methyl-6-bromo-pyridine-2-carboxylate in 46 ml N,N-dimethylformamide and the mixture was heated to 80° C. Then 4.52 g (13.9 mmol) cesium carbonate and 2.1 g (10.18 mmol) of 4-(trifluoromethoxy)phenylboronic acid were added and the mixture was stirred at 80° C. over night. The reaction mixture was cooled to room temperature, filtered, and the filtrate evaporated. The residue was taken up with ethyl acetate, washed twice with water, dried over sodium sulphate and evaporated. Chromatography on silica (eluent: ethyl acetate/n-heptane 1:3) gave 1.23 g (39%) of 6-(4-Trifluoromethoxy-phenyl)-pyridine-2-carboxylic acid methyl ester

MS: 298.2 (ESI+)

$^1$H-NMR (400 Hz, [$D_6$]DMSO): δ=3.94 (s, 3H, O—$CH_3$), 7.53 (d, 2H, Ar—O—$CF_3$), 8.05 (d, 1H, pyridine), 8.12 (t, 1H, pyridine), 8.27 (d, 2H, Ar—O—$CF_3$), 8.27 (d, 1H, pyridine)

ii) [6-(4-Trifluoromethoxy-phenyl)-pyridin-2-yl]-methanol 151 mg (3.98 mmol) lithium aluminium hydride were given to 8 ml tetrahydrofuran (THF) and stirred at 0° C. for 10 min. A solution of 591 mg (1.99 mmol) 6-(4-Trifluoromethoxy-phenyl)-pyridine-2-carboxylic acid methyl ester in 8 ml THF was added drop by drop within 10 min., and the mixture stirred for 3 h at 0° C. 15 ml conc. Sodium chloride solution were added slowly at 0° C. and stirred continued for 2 h. The mixture was adjusted to pH=5 by addition of conc. HCl. A formed salt precipitate was isolated by fitration and washed with THF. The combined THF-solutions were evaporated, the residue extracted twice with ethyl acetate, the organic phase dried (sodium sulphate) and evaporated. Chromatography on silica (eluent: ethyl acetate/n-heptane 1:3) gave 0.81 g (92%) of [6-(4-Trifluoromethyl-phenyl)-pyridine-2-yl]-methanol.

MS: 270.2 (ESI+)

$^1$H-NMR (400 Hz, [$D_6$]DMSO): δ=4.64 (d, 2H, $CH_2$), 5.46 (t, 1H, —OH), 7.47 (d, 2H, Ar—O—$CF_3$), 7.47 (d, 1H, pyridine), 7.85 (d, 1H, pyridine), 7.92 (t, 1H, pyridine), 8.20 (d, 2H, Ar—O—$CF_3$)

iii) 2-Chloromethyl-6-(4-trifluoromethoxy-phenyl)-pyridine 607 mg (0.37 ml, 5.10 mmol) thionyl chloride were added drop by drop at 0° C. to a solution of 0.2 ml N,N-dimethylformamide (DMF) and 686 mg (2.55 mmol) [6-(4-Trifluoromethyl-phenyl)-pyridine-2-yl]-methanol in 20 ml dichloromethane and stirred for 2 h at 0° C. The mixture was poured on ice/sodium bicarbonate solution and the organic phase separated. The water phase is extracted with dichloromethane. The combined organic phases were washed with water, dried (sodium sulphate), evaporated and the obtained material (711 mg, 96%) used without further purification.

MS: 288.1 (ESI+)

$^1$H-NMR (400 Hz, [$D_6$]DMSO): δ=4.86 (d, 2H, $CH_2$), 7.50 (d, 2H, Ar—O—$CF_3$), 7.56 (d, 1H, pyridine), 7.97 (m, 2H, pyridine), 8.22 (d, 2H, Ar—O—$CF_3$)

Preparation of 2-[3-Methyl-4-(4-[1,2,3]triazol-1-yl-butyl)-phenoxymethyl]-6-(4-trifluoromethoxy-phenyl)-pyridine A solution of 39 mg (0.17 mmol) 3-methyl-4-(4-[1,2,3]triazol-1-yl-butyl)phenol in 2.0 ml N,N-dimethylformamide was treated at 0° C. with 7 mg (0.17 mmol) of 60% sodium hydride and stirred at 0° C. for 30 min. Then 50 mg (0.17 mmol) 2-Chloromethyl-6-(4-trifluoromethoxy-phenyl)-pyridine were added and stirred continued at r.t. over night. After addition of 4 ml water, the precipitate was isolated, washed thoroughly with water, n-heptane and diisopropylether. The residue was dried at 40° C. to give 65 mg (77%) of the title compound as white powder.

MS: 483.3 (ESI+)

$^1$H-NMR (400 Hz, [D$_6$]DMSO): δ=1.43 (quintet, 2H, CH$_2$—CH$_2$—Ar), 1.86 (quintet, 2H, CH$_2$—CH$_2$-triazole), 2.20 (s, 3H, CH$_3$), 2.51 (t, 2H, CH$_2$—Ar), 4.41 (t, 2H, CH$_2$-triazole), 5.21 (s, 2H, OCH$_2$), 6.79 (d, 1H, OAr), 6.87 (s, 1H, OAr), 7.01 (d, 1H, OAr), 7.49 (d, 2H, Ar—O—CF$_3$), 7.49 (d, 1H, pyridine), 7.71 (s, 1H, triazole), 7.95 (m, 2H, pyridine), 8.11 (s, 1H, triazole), 8.23 (d, 2H, Ar—O—CF$_3$).

Example 31

2-[4-(4-[1,2,3]Triazol-1-yl-butyl)-phenoxymethyl]-6-(4-trifluoromethoxy-phenyl)-pyridine A solution of 37 mg (0.17 mmol) 4-(4-[1,2,3]triazol-1-yl-butyl)phenol in 2.0 ml N,N-dimethylformamide was treated at 0° C. with 7 mg (0.17 mmol) of 60% sodium hydride and stirred at 0° C. for 30 min. Then 50 mg (0.17 mmol) 2-Chloromethyl-6-(4-trifluoromethoxy-phenyl)-pyridine were added and stirred continued at r.t. over night. After addition of 4 ml water, the precipitate was isolated, washed thoroughly with water, n-heptane and diethylether. The residue was dried at 40° C. to give 15 mg (18%) of the title compound as white powder.

MS: 469.3 (ESI+)

$^1$H-NMR (400 Hz, [D$_6$]DMSO): δ=1.48 (quintet, 2H, CH$_2$—CH$_2$—Ar), 1.81 (quintet, 2H, CH$_2$—CH$_2$-triazole), 2.52 (t, 2H, CH$_2$—Ar), 4.39 (t, 2H, CH$_2$-triazole), 5.22 (s, 2H, OCH$_2$), 6.96 (d, 2H, OAr), 7.10 (d, 2H, OAr), 7.49 (d, 1H, Ar—O—CF$_3$), 7.49 (d, 1H, pyridine), 7.70 (s, 1H, triazole), 7.95 (d, 2H, pyridine), 8.10 (s, 1H, triazole), 8.23 (d, 2H, Ar—O—CF$_3$).

Example 32

3-[3-Methyl-4-(4-[1,2,3]triazol-1-yl-butyl)-phenoxymethyl]-5-(4-trifluoromethyl-phenyl)-pyridine Preparation of 3-Chloromethyl-5-(4-trifluoromethyl-phenyl)-pyridine i) 5-(4-Trifluoromethyl-phenyl)-nicotinic acid methyl ester 81 mg (0.07 mmol)Pd(PPh$_3$)$_4$ was added under argon at room temperature to a solution of 1.0 g (4.63 mmol) methyl-5-bromo-pyridine-3-carboxylate in 23 ml N,N-dimethylformamide and the mixture was heated to 80° C. Then 2.26 g (6.94 mmol) cesium carbonate and 0.97 g (5.09 mmol) of 4-(trifluoromethyl)phenyl boronic acid were added and the mixture was stirred at 80° C. over night. The reaction mixture was cooled to room temperature, filtered, and the filtrate evaporated. The residue was taken up with ethyl acetate, washed twice with water, dried over sodium sulphate and evaporated. Chromatography on silica (eluent: ethyl acetate/n-heptane 1:3) gave 1.0 g (68%) of 5-(4-Trifluoromethyl-phenyl)-nicotinic acid methyl ester

MS: 282.1 (ESI+)

$^1$H-NMR (400 Hz, [D$_6$]DMSO): δ=3.94 (s, 3H, O—CH$_3$), 7.88 (d, 2H, Ar—CF$_3$), 8.05 (d, 2H, Ar—CF$_3$), 8.56 (d, 1H, pyridine), 9.14 (s, 1H, pyridine), 9.21 (d, 1H, pyridine)

ii) [5-(4-Trifluoromethyl-phenyl)-pyridin-3-yl]-methanol

A solution of 335 mg (1.17 mmol) 5-(4-Trifluoromethyl-phenyl)-nicotinic acid methyl ester in 10.0 ml ethanol was treated at room temperature (r. t.) with 44 mg (1.17 mmol) of sodium borohydride. The mixture stirred two days at 50° C. Then it was poured on ice and extracted tree times with ethyl acetate. The combined organic phases were washed with water, dried (sodium sulphate) and evaporated. Chromatography on silica (eluent: ethyl acetate/methanol 5:1) gave 195 mg (64%) of [5-(4-Trifluoromethyl-phenyl)-pyridin-3-yl]-methanol.

MS: 254.0 (ESI+)

$^1$H-NMR (400 Hz, [D$_6$]DMSO): δ=4.63 (d, 2H, CH$_2$), 5.42 (t, 1H, —OH), 7.87 (d, 2H, Ar—CF$_3$), 7.96 (d, 2H, Ar—CF$_3$), 8.07 (s, 1H, pyridine), 8.59 (s, 1H, pyridine), 8.85 (s, 1H, pyridine).

iii) 3-Chloromethyl-5-(4-trifluoromethyl-phenyl)-pyridine 177 mg (0.11 ml, 1.49 mmol) thionyl chloride were added drop by drop at 0° C. to a solution of 0.1 ml N,N-dimethyl-formamide (DMF) and 196 mg (0.74 mmol) [5-(4-Trifluoromethyl-phenyl)-pyridin-3-yl]-methanol in 6 ml dichloromethane and stirred for 1.5 h at 0° C. The mixture was poured on ice/sodium bicarbonate solution and the organic phase separated. The water phase is extracted with dichloromethane. The combined organic phases were washed with water, dried (sodium sulphate), evaporated and the obtained material (174 mg, 81%) used without further purification.

MS: 272.1 (ESI+)

$^1$H-NMR (400 Hz, [D$_6$]DMSO): δ=4.90 (d, 2H, CH$_2$), 7.88 (d, 2H, Ar—CF$_3$), 7.99 (d, 2H, Ar—CF$_3$), 8.25 (s, 1H, pyridine), 8.72 (s, 1H, pyridine), 8.94 (s, 1H, pyridine)

Preparation of 3-[3-Methyl-4-(4-[1,2,3]triazol-1-yl-butyl)-phenoxymethyl]-5-(4-trifluoromethyl-phenyl)-pyridine A solution of 39 mg (0.17 mmol) 3-methyl-4-(4-[1,2,3]triazol-1-yl-butyl)phenol in 2.0 ml N,N-dimethylformamide was treated at 0° C. with 7 mg (0.17 mmol) of 60% sodium hydride and stirred at 0° C. for 30 min. Then 50 mg (0.17 mmol) 3-Chloromethyl-5-(4-trifluoromethyl-phenyl)-pyridine were added and stirred continued at r. t. over night. After addition of 4 ml water, the precipitate was isolated, washed thoroughly with water, n-heptane and diisopropylether. The residue was dried at 40° C. to give 33 mg (41%) of the title compound as light brown powder.

MS: 467.3 (ESI+)

$^1$H-NMR (400 Hz, [D$_6$]DMSO): δ=1.43 (quintet, 2H, CH$_2$—CH$_2$—Ar), 1.86 (quintet, 2H, CH$_2$—CH$_2$-triazole), 2.21 (s, 3H, CH$_3$), 2.51 (t, 2H, CH$_2$—Ar), 4.41 (t, 2H, CH$_2$-triazole), 5.19 (s, 2H, OCH$_2$), 6.80 (d, 1H, OAr), 6.86 (s, 1H, OAr), 7.02 (d, 1H, OAr), 7.71 (s, 1H, triazole), 7.88 (d, 2H, Ar—CF$_3$), 7.99 (d, 2H, Ar—CF$_3$), 8.11 (s, 1H, triazole), 8.22 (s, 1H, pyridine), 8.72 (s, 1H, pyridine), 8.93 (s, 1H, pyridine).

Example 33

3-[4-(4-[1,2,3]Triazol-1-yl-butyl)-phenoxymethyl]-5-(4-trifluoromethyl-phenyl)-pyridine A solution of 37 mg (0.17 mmol) 4-(4-[1,2,3]triazol-1-yl-butyl)phenol in 2.0 ml N,N-dimethylformamide was treated at 0° C. with 7 mg (0.17 mmol) of 60% sodium hydride and stirred at 0° C. for 30 min. Then 50 mg (0.17 mmol) 3-Chloromethyl-5-(4-trifluoromethyl-phenyl)-pyridine were added and stirred continued at r. t. over night. After addition of 4 ml water, the precipitate was isolated, washed thoroughly with water, n-heptane and diisopropylether. The residue was dried at 40° C. to give 36 mg (46%) of the title compound as light brown powder.

MS: 453.3 (ESI+)

$^1$H-NMR (400 Hz, [D$_6$]DMSO): δ=1.49 (quintet, 2H, CH$_2$—CH$_2$—Ar), 1.81 (quintet, 2H, CH$_2$—CH$_2$-triazole), 2.51 (t, 2H, CH$_2$—Ar), 4.39 (t, 2H, CH$_2$-triazole), 5.21 (s, 2H, OCH$_2$), 6.97 (d, 2H, OAr), 7.11 (d, 2H, OAr), 7.71 (s, 1H, triazole), 7.88 (d, 2H, Ar—CF$_3$), 7.99 (d, 2H, Ar—CF$_3$), 8.10 (s, 1H, triazole), 8.23 (s, 1H, pyridine), 8.72 (s, 1H, pyridine), 8.93 (s, 1H, pyridine).

Example 34

2-(4-Chloro-phenyl)-6-[3-methyl-4-(4-[1,2,3]triazol-1-yl-butyl)-phenoxymethyl]-pyridine A solution of 97 mg (0.42 mmol) 3-methyl-4-(4-[1,2,3]triazol-1-yl-butyl)phenol in 4.0 ml N,N-dimethylformamide was treated at 0° C. with 17 mg (0.42 mmol) of 60% sodium hydride and stirred at 0° C. for 30 min. Then 100 mg (0.42 mmol) 2-Chloromethyl-6-(4-chloro-phenyl)-pyridine [ZA 6706809] were added and stirred continued at r.t. over night. After addition of 8 ml water, the precipitate was isolated, washed thoroughly with water and n-heptane. The residue was dried at 40° C. to give 143 mg (78%) of the title compound as white powder.

MS: 433.4 (ESI+)

$^1$H-NMR (400 Hz, [D$_6$]DMSO): δ=1.42 (quintet, 2H, CH$_2$—CH$_2$—Ar), 1.85 (quintet, 2H, CH$_2$—CH$_2$-triazole), 2.20 (s, 3H, CH$_3$), 2.51 (t, 2H, CH$_2$—Ar), 4.40 (t, 2H, CH$_2$-triazole), 5.20 (s, 2H, OCH$_2$), 6.78 (d, 1H, OAr), 6.87 (s, 1H, OAr), 7.00 (d, 1H, OAr), 7.47 (t, 1H, pyridine), 7.56 (d, 2H, Ar—Cl), 7.70 (s, 1H, triazole), 7.92 (d, 2H, pyridine), 8.11 (s, 1H, triazole), 8.14 (d, 2H, Ar—Cl).

Example 35

2-(4-Chloro-phenyl)-6-[4-(4-[1,2,3]triazol-1-yl-butyl)-phenoxymethyl]-pyridine

A solution of 89 mg (0.42 mmol) 4-(4-[1,2,3]triazol-1-yl-butyl)phenol in 4.0 ml N,N-dimethylformamide was treated at 0° C. with 17 mg (0.42 mmol) of 60% sodium hydride and stirred at 0° C. for 30 min. Then 100 mg (0.42 mmol) 2-Chloromethyl-6-(4-chloro-phenyl)-pyridine [ZA 6706809] were added and stirred continued at r.t. over night. After addition of 8 ml water, the precipitate was isolated, washed thoroughly with water and n-heptane. The residue was dried at 40° C. and purified by LC-MS to give 80.5 mg (47%) of the title compound as white powder.

MS: 419.0 (ESI+)

$^1$H-NMR (400 Hz, [D$_6$]DMSO): δ=1.48 (quintet, 2H, CH$_2$—CH$_2$—Ar), 1.81 (quintet, 2H, CH$_2$—CH$_2$-triazole), 2.51 (t, 2H, CH$_2$—Ar), 4.38 (t, 2H, CH$_2$-triazole), 5.22 (s, 2H, OCH$_2$), 6.96 (d, 2H, OAr), 7.10 (d, 2H, OAr), 7.48 (t, 1H, pyridin), 7.56 (d, 2H, Ar—Cl), 7.70 (s, 1H, triazole), 7.93 (d, 2H, pyridine), 8.10 (s, 1H, triazole), 8.13 (d, 2H, Ar—Cl).

Example 36

3-[3-Methyl-4-(4-[1,2,3]triazol-1-yl-butyl)-phenoxymethyl]-5-(4-trifluoromethoxy-phenyl)-pyridine Preparation of 3-Chloromethyl-5-(4-trifluoromethoxy-phenyl)-pyridine i) 5-(4-Trifluoromethoxy-phenyl)-nicotinic acid methyl ester 81 mg (0.07 mmol)Pd(PPh$_3$)$_4$ was added under argon at room temperature to a solution of 1.0 g (4.63 mmol) methyl-5-bromo-pyridine-3-carboxylate in 23 ml N,N-dimethylformamide and the mixture was heated to 80° C. Then 2.26 g (6.94 mmol) cesium carbonate and 1.05 g (5.09 mmol) of 4-(trifluoromethoxy)phenyl boronic acid were added and the mixture was stirred at 80° C. over night. The reaction mixture was cooled to room temperature, filtered, and the filtrate evaporated. The residue was taken up with ethyl acetate, washed twice with water, dried over sodium sulphate and evaporated. Chromatography on silica (eluent: ethyl acetate/n-heptane 1:3) gave 0.75 g (49%) of 5-(4-Trifluoromethoxy-phenyl)-nicotinic acid methyl ester

MS: 298.2 (ESI+)

$^1$H-NMR (400 Hz, [D$_6$]DMSO): δ=3.93 (s, 3H, O—CH$_3$), 7.52 (d, 2H, Ar—O—CF$_3$), 7.95 (d, 2H, Ar—O—CF$_3$), 8.50 (s, 1H, pyridine), 9.10 (s, 1H, pyridine), 9.17 (s, 1H, pyridine)

ii) [5-(4-Trifluoromethoxy-phenyl)-pyridin-3-yl]-methanol

A solution of 535 mg (1.76 mmol) 5-(4-Trifluoromethoxy-phenyl)-nicotinic acid methyl ester in 16 ml Ethanol was treated at room temperature (r. t.) with 67 mg (1.76 mmol) of sodium borohydride. The mixture was stirred for 4 h. at r. t., then two days at 80° C. The mixture was poured on ice and extracted tree times with ethyl acetate. The combined organic phases were washed with water, dried (sodium sulphate) and evaporated. Chromatography on silica (eluent: ethyl acetate/methanol 5:1) gave 159 mg (33%) of [5-(4-Trifluoromethoxy-phenyl)-pyridin-3-yl]-methanol.

MS: 270.1 (ESI+)

$^1$H-NMR (400 Hz, [D$_6$]DMSO): δ=4.63 (d, 2H, CH$_2$), 5.39 (t, 1H, —OH), 7.50 (d, 2H, Ar—O—CF$_3$), 7.87 (d, 2H, Ar—O—CF$_3$), 8.01 (t, 1H, pyridine), 8.56 (d, 1H, pyridine), 8.79 (d, 1H, pyridine).

iii) 3-Chloromethyl-5-(4-trifluoromethoxy-phenyl)-pyridine 136 mg (0.083 ml, 1.14 mmol) thionyl chloride were added drop by drop at 0° C. to a solution of 0.1 ml N,N-dimethylformamide (DMF) and 153 mg (0.57 mmol) [5-(4-Trifluoromethoxy-phenyl)-pyridin-3-yl]-methanol in 10 ml dichloromethane and stirred for 2 h at 0° C. The mixture was poured on ice/sodium bicarbonate solution and the organic phase separated. The water phase is extracted with dichloromethane. The combined organic phases were washed with water, dried (sodium sulphate), evaporated and the obtained material (156 mg, 89%) used without further purification.

MS: 288.1 (ESI+)

$^1$H-NMR (400 Hz, [D$_6$]DMSO): δ=4.90 (d, 2H, CH$_2$), 7.51 (d, 2H, Ar—O—CF$_3$), 7.88 (d, 2H, Ar—O—CF$_3$), 8.19 (s, 1H, pyridine), 8.68 (s, 1H, pyridine), 8.89 (s, 1H, pyridine)

Preparation of 3-[3-Methyl-4-(4-[1,2,3]triazol-1-yl-butyl)-phenoxymethyl]-5-(4-trifluoromethoxy-phenyl)-pyridine A solution of 60 mg (0.26 mmol) 3-methyl-4-(4-[1,2,3]triazol-1-yl-butyl)phenol in 4.0 ml N,N-dimethylformamide was treated at 0° C. with 10 mg (0.26 mmol) of 60% sodium hydride and stirred at 0° C. for 30 min. Then 80 mg (0.26 mmol) 3-Chloromethyl-5-(4-trifluoromethoxy-phenyl)-pyridine were added and stirred continued at r.t. over night. After addition of 8 ml water, the precipitate was isolated, washed thoroughly with water, n-heptane and diisopropylether. The residue was dried at 40° C. to give 91 mg (72%) of the title compound as ochre powder.

MS: 483.4 (ESI+)

$^1$H-NMR (400 Hz, [D$_6$]DMSO): δ=1.43 (quintet, 2H, CH$_2$—CH$_2$—Ar), 1.85 (quintet, 2H, CH$_2$—CH$_2$-triazole), 2.21 (s, 3H, CH$_3$), 2.50 (t, 2H, CH$_2$—Ar), 4.40 (t, 2H, CH$_2$-triazole), 5.17 (s, 2H, OCH$_2$), 6.80 (d, 1H, OAr), 6.85 (s, 1H, OAr), 7.01 (d, 1H, OAr), 7.50 (d, 2H, Ar—O—CF$_3$), 7.70 (s, 1H, triazole), 7.88 (d, 2H, Ar—O—CF$_3$), 8.10 (s, 1H, triazole), 8.15 (s, 1H, pyridine), 8.67 (s, 1H, pyridine), 8.87 (s, 1H, pyridine).

Example 37

3-[4-(4-[1,2,3]Triazol-1-yl-butyl)-phenoxymethyl]-5-(4-trifluoromethoxy-phenyl)-pyridine A solution of 56 mg (0.24 mmol) 4-(4-[1,2,3]triazol-1-yl-butyl)phenol in 4.0 ml N,N-dimethylformamide was treated at 0° C. with 10 mg (0.24 mmol) of 60% sodium hydride and stirred at 0° C. for 30 min. Then 74 mg (0.24 mmol) 3-Chloromethyl-5-(4-trifluoromethoxy-phenyl)-pyridine were added and stirred continued at r.t. over night. After addition of 8 ml water, the precipitate was isolated, washed thoroughly with water, n-heptane and diisopropylether. The residue was dried at 40° C. to give 56 mg (49%) of the title compound as light brown powder.

MS: 469.4 (ESI+)

$^1$H-NMR (400 Hz, [D$_6$]DMSO): δ=1.48 (quintet, 2H, CH$_2$—CH$_2$—Ar), 1.80 (quintet, 2H, CH$_2$—CH$_2$-triazole), 2.51 (t, 2H, CH$_2$—Ar), 4.38 (t, 2H, CH$_2$-triazole), 5.19 (s, 2H, OCH$_2$), 6.96 (d, 2H, OAr), 7.10 (d, 2H, OAr), 7.50 (d, 2H, Ar—O—CF$_3$), 7.70 (s, 1H, triazole), 7.88 (d, 2H, Ar—O—CF$_3$), 8.10 (s, 1H, triazole), 8.17 (s, 1H, pyridine), 8.68 (s, 1H, pyridine), 8.88 (s, 1H, pyridine).

Example 38

3-(4-Chloro-phenyl)-5-[3-methyl-4-(4-[1,2,3]triazol-1-yl-butyl)-phenoxymethyl]-pyridine Preparation of 3-Chloromethyl-5-(4-chloro-phenyl)-pyridine i) 5-(4-Chloro-phenyl)-nicotinic acid methyl ester 81 mg (0.07 mmol)Pd(PPh$_3$)$_4$ was added under argon at room temperature to a solution of 1.0 g (4.63 mmol) methyl-5-bromo-pyridine-3-carboxylate in 23 ml N,N-dimethylformamide and the mixture was heated to 80° C. Then 2.26 g (6.94 mmol) cesium carbonate and 0.84 g (5.09 mmol) of 4-chlorophenyl boronic acid were added and the mixture was stirred at 80° C. over night. The reaction mixture was cooled to room temperature, filtered, and the filtrate evaporated. The residue was taken up with ethyl acetate, washed twice with water, dried over sodium sulphate and evaporated. Chromatography on silica (eluent: ethyl acetate/n-heptane 1:3) gave 0.91 g (69%) of 5-(4-Chloro-phenyl)-nicotinic acid methyl ester

MS: 248.1 (ESI+)

$^1$H-NMR (400 Hz, [D$_6$]DMSO): δ=3.93 (s, 3H, O—CH$_3$), 7.59 (d, 2H, Ar—Cl), 7.85 (d, 2H, Ar—Cl), 8.48 (s, 1H, pyridine), 9.09 (s, 1H, pyridine), 9.15 (s, 1H, pyridine)

ii) [5-(4-Chloro-phenyl)-pyridin-3-yl]-methanol

A solution of 900 mg (3.49 mmol) 5-(4-Chloro-phenyl)-nicotinic acid methyl ester in 30.0 ml Ethanol was treated at room temperature (r. t.) with 264 mg (69.9 mmol) of sodium borohydride. The mixture was stirred for two days at 50° C. Then it was poured on ice and extracted tree times with ethyl acetate. The combined organic phases were washed with water, dried (sodium sulphate) and evaporated. Chromatography on silica (eluent: ethyl acetate/methanol 6:1) gave 522 mg (67%) of [5-(4-Chloro-phenyl)-pyridin-3-yl]-methanol.

MS: 219.9 (ESI+)

$^1$H-NMR (400 Hz, [D$_6$]DMSO): δ=4.61 (d, 2H, CH$_2$), 5.37 (t, 1H, —OH), 7.56 (d, 2H, Ar—Cl), 7.75 (d, 2H, Ar—Cl), 7.99 (s, 1H, pyridine), 8.54 (s, 1H, pyridine), 8.78 (s, 1H, pyridine).

iii) 3-Chloromethyl-5-(4-chloro-phenyl)-pyridine 543 mg (0.333 ml, 4.56 mmol) thionyl chloride were added drop by drop at 0° C. to a solution of 0.2 ml N,N-dimethylformamide (DMF) and 500 mg (2.28 mmol) [5-(4-Chloro-phenyl)-pyridin-3-yl]-methanol in 30 ml dichloromethane and stirred for 2 h at 0° C. The mixture was poured on ice/sodium bicarbonate solution and the organic phase separated. The water phase is extracted with dichloromethane. The combined organic phases were washed with water, dried (sodium sulphate), evaporated and the obtained material (444 mg, 75%) used without further purification.

MS: 238.1 (ESI+)

$^1$H-NMR (400 Hz, [D$_6$]DMSO): δ=4.88 (d, 2H, CH$_2$), 7.58 (d, 2H, Ar—Cl), 7.80 (d, 2H, Ar—Cl), 8.17 (s, 1H, pyridine), 8.67 (s, 1H, pyridine), 8.88 (s, 1H, pyridine)

Preparation of 3-(4-Chloro-pheml)-5-[3-methyl-4-(4-[1,2,3]triazol-1-yl-butyl), phenoxymethyl]-pyridine A solution of 90 mg (0.39 mmol) 3-methyl-4-(4-[1,2,3]triazol-1-yl-butyl)phenol in 4.0 ml N,N-dimethylformamide was treated at 0° C. with 16 mg (0.39 mmol) of 60% sodium hydride and stirred at 0° C. for 30 min. Then 100 mg (0.39 mmol) 3-Chloromethyl-5-(4-chloro-phenyl)-pyridine were added and stirred continued at r. t. over night. After addition of 8 ml water, the precipitate was isolated, washed thoroughly with water and n-heptane. The residue was dried at 40° C. to give 124 mg (74%) of the title compound as white powder.

MS: 433.4 (ESI+)

$^1$H-NMR (400 Hz, [D$_6$]DMSO): δ=1.42 (quintet, 2H, CH$_2$—CH$_2$—Ar), 1.85 (quintet, 2H, CH$_2$—CH$_2$-triazole), 2.20 (s, 3H, CH$_3$), 2.51 (t, 2H, CH$_2$—Ar), 4.40 (t, 2H, CH$_2$-triazole), 5.16 (s, 2H, OCH$_2$), 6.80 (d, 1H, OAr), 6.85 (s, 1H, OAr), 7.01 (d, 1H, OAr), 7.57 (d, 2H, Ar—Cl), 7.70 (s, 1H, triazole), 7.77 (d, 2H, Ar—Cl), 8.10 (s, 1H, triazole), 8.14 (s, 1H, pyridine), 8.66 (s, 1H, pyridine), 8.86 (s, 1H, pyridine).

Example 39

3-(4-Chloro-phenyl)-5-[4-(4-[1,2,3]triazol-1-yl-butyl)-phenoxymethyl]-pyridine A solution of 85 mg (0.39 mmol) 4-(4-[1,2,3]triazol-1-yl-butyl)phenol in 4.0 ml N,N-dimethylformamide was treated at 0° C. with 16 mg (0.39 mmol) of 60% sodium hydride and stirred at 0° C. for 30 min. Then 100 mg (0.39 mmol) 3-Chloromethyl-5-(4-chloro-phenyl)-pyridine were added and stirred continued at r. t. over night. After addition of 8 ml water, the precipitate was isolated, washed thoroughly with water and n-heptane. The residue was dried at 40° C. to give 108 mg (67%) of the title compound as light brown powder.

MS: 419.3 (ESI+)

$^1$H-NMR (400 Hz, [D$_6$]DMSO): δ=1.48 (quintet, 2H, CH$_2$—CH$_2$—Ar), 1.80 (quintet, 2H, CH$_2$—CH$_2$-triazole), 2.50 (t, 2H, CH$_2$—Ar), 4.38 (t, 2H, CH$_2$-triazole), 5.18 (s, 2H, OCH$_2$), 6.96 (d, 2H, OAr), 7.10 (d, 2H, OAr), 7.58 (d, 2H, Ar—Cl), 7.70 (s, 1H, triazole), 7.78 (d, 2H, Ar—Cl), 8.10 (s, 1H, triazole), 8.15 (s, 1H, pyridine), 8.66 (s, 1H, pyridine), 8.86 (s, 1H, pyridine).

Example 40

2-(3-Chloro-phenyl)-6-[3-methyl-4-(4-[1,2,3]triazol-1-yl-butyl)-phenoxymethyl]-pyridine Preparation of 2-Chloromethyl-6-(3-chloro-phenyl)-pyridine i) 6-(3-Chloro-phenyl)-pyridine-2-carboxylic acid methyl ester 104 mg (0.09 mmol)Pd(PPh$_3$)$_4$, 1.5 g (6.29 mmol) of 3-chlorophenylboronic acid pinacol ester 2.86 ml (8.58 mmol) and 3M cesium carbonate solution were added under argon at room temperature to a solution of 1.24 g (5.72 mmol) methyl-5-bromo-pyridine-3-carboxylate in 45 ml dimethoxyethane and the mixture was heated to reflux for 30 min. The reaction mixture was cooled to room temperature and evaporated. The residue was taken up with ethyl acetate, washed with water, dried over sodium sulphate and evaporated. Chromatography on silica (eluent: ethyl acetate/n-heptane 1:3) gave 1.42 g (83%) of 6-(3-Chloro-phenyl)-pyridine-2-carboxylic acid methyl ester

MS: 248.1 (ESI+)

ii) [6-(3-Chloro-phenyl)-pyridin-2-yl]-methanol 399 mg (10.50 mmol) lithium aluminium hydride were given to 18 ml tetrahydrofuran (THF) and stirred at room temperature (r. t.) for 10 min. A solution of 1.30 g (5.25 mmol) 6-(3-Chloro-phenyl)-pyridine-2-carboxylic acid methyl ester in 18 ml THF was added drop by drop at 0° C. within 15 min., and the mixture stirred for 2 h at 0° C. 32 ml brine were added slowly at 0° C. and stirred continued for 2 h. The mixture was adjusted to pH=5 by slowly addition of conc. HCl. A formed salt precipitate was isolated by filtration and washed with THF. The combined THF-solutions were evaporated, the residue extracted twice with ethyl acetate, the organic phase dried (sodium sulphate) and evaporated. Chromatography on silica (eluent: ethyl acetate/n-heptane 1:1) gave 0.45 g (35%) of [6-(3-Chloro-phenyl)-pyridin-2-yl]-methanol

MS: 220.1 (ESI+)

$^1$H-NMR (400 Hz, [D$_6$]DMSO): δ=4.65 (d, 2H, CH$_2$), 5.47 (t, 1H, —OH), 7.50 (m, 3H, Ar—Cl), 7.71 (d, 1H, Ar—Cl), 7.89 (m, 1H, Ar—Cl), 8.89 (m, 1H, pyridine), 8.06 (d, 1H, pyridine), 8.14 (s, 1H, pyridine).

iii) 2-Chloromethyl-6-(3-chloro-phenyl)-pyridine 433 mg (0.264 ml, 3.64 mmol) thionyl chloride were added drop by drop at 0° C. to a solution of 0.2 ml N,N-dimethylformamide (DMF) and 400 mg (1.82 mmol) [6-(3-Chloro-phenyl)-pyridin-2-yl]-methanol in 25 ml dichloromethane and stirred for 3 h at 0° C. The mixture was poured on ice/sodium bicarbonate solution and the organic phase separated. The water phase is extracted with dichloromethane. The combined organic phases were washed with water, dried (sodium sulphate), evaporated and the obtained material (409 mg, 94%) used without further purification.

MS: 238.0 (ESI$^+$)

$^1$H-NMR (400 Hz, [D$_6$]DMSO): δ=4.87 (d, 2H, CH$_2$), 7.53 (m, 3H, Ar—Cl), 7.99 (m, 1H, Ar—Cl), 7.99 (m, 1H, pyridine), 8.09 (d, 1H, pyridine), 8.16 (s, 1H, pyridine)

Preparation of 2-(3-Chloro-phenyl)-6-[3-methyl-4-(4-[1,2,3]triazol-1-yl-butyl)-phenoxymethyl]-pyridine A solution of 97 mg (0.42 mmol) 3-methyl-4-(4-[1,2,3]triazol-1-yl-butyl)phenol in 4.0 ml N,N-dimethylformamide was treated at 0° C. with 17 mg (0.42 mmol) of 60% sodium hydride and stirred at 0° C. for 30 min. Then 100 mg (0.42 mmol) 2-Chloromethyl-6-(3-chloro-phenyl)-pyridine were added and stirred continued at r. t. over night. After addition of 8 ml water, the mixture was extracted with ethyl acetate tree times. The combined organic phases were dried (sodium sulphate) and evaporated. Chromatography on silica (eluent: ethyl acetate/n-heptane 2:1) gave 0.151 g (83%) the title compound as white powder.

MS: 433.3 (ESI+)

$^1$H-NMR (400 Hz, [D$_6$]DMSO): δ=1.42 (quintet, 2H, CH$_2$—CH$_2$—Ar), 1.85 (quintet, 2H, CH$_2$—CH$_2$-triazole), 2.20 (s, 3H, CH$_3$), 2.51 (t, 2H, CH$_2$—Ar), 4.40 (t, 2H, CH$_2$-triazole), 5.21 (s, 2H, OCH$_2$), 6.79 (d, 1H, OAr), 6.88 (s, 1H, OAr), 7.00 (d, 1H, OAr), 7.52 (m, 3H, Ar—Cl), 7.70 (s, 1H, triazole), 7.95 (m, 1H, Ar—Cl), 7.95 (m, 1H, pyridine), 8.07 (d, 1H, pyridine), 8.11 (s, 1H, triazole), 8.16 (s, 1H, pyridine)

Example 41

3-(3-Chloro-phenyl)-5-[3-methyl-4-(4-[1,2,3]triazol-1-yl-butyl)-phenoxymethyl]-pyridine Preparation of 3-Chloromethyl-5-(3-chloro-phenyl)-pyridine i) 5-(3-Chloro-phenyl)-nicotinic acid methyl ester 104 mg (0.09 mmol)Pd(PPh$_3$)$_4$, 1.5 g (6.29 mmol) of 3-chlorophenylboronic acid pinacol ester 2.86 ml (8.58 mmol) and 3M cesium carbonate solution were added under argon at room temperature to a solution of 1.24 g (5.72 mmol) methyl-5-bromo-pyridine-3-carboxylate in 45 ml dimethoxyethane and the mixture was heated to reflux for 30 min. The reaction mixture was cooled to room temperature and evaporated. The residue was taken up with ethyl acetate, washed with water, dried over sodium sulphate and evaporated. Chromatography on silica (eluent: ethyl acetate/n-heptane 1:3) gave 1.14 g (72%) of 5-(3-Chloro-phenyl)-nicotinic acid methyl ester

MS: 248.2 (ESI+)

$^1$H-NMR (400 Hz, [D$_6$]DMSO): δ=3.95 (s, 3H, O—CH$_3$), 7.54 (m, 2H, Ar—Cl), 7.79 (d, 1H, Ar—Cl), 7.92 (s, 1H, Ar—Cl), 8.51 (s, 1H, pyridine), 9.10 (s, 1H, pyridine), 9.17 (s, 1H, pyridine)

ii) [5-(3-Chloro-phenyl)-pyridin-3-yl]-methanol

A solution of 1.0 g (4.04 mmol) 5-(3-Chloro-phenyl)-nicotinic acid methyl ester in 60.0 ml Ethanol was treated at room temperature (r. t.) with 304 mg (80.7 mmol) of sodium borohydride. The mixture was stirred over night at 50° C. Then it was poured on ice and extracted tree times with ethyl acetate. The combined organic phases were washed with water, dried (sodium sulphate) and evaporated. Chromatography on silica (eluent: ethyl acetate/n-heptane 1:1) gave 261 mg (26%) of [5-(3-Chloro-phenyl)-pyridin-3-yl]-methanol.

MS: 220.1 (ESI+)

$^1$H-NMR (400 Hz, [D$_6$]DMSO): δ=4.62 (d, 2H, CH$_2$), 5.39 (t, 1H, —OH), 7.51 (m, 2H, Ar—Cl), 7.71 (d, 1H, Ar—Cl), 7.81 (s, 1H, Ar—Cl), 8.03 (s, 1H, pyridine), 8.56 (s, 1H, pyridine), 8.80 (s, 1H, pyridine).

iii) 3-Chloromethyl-5-(3-chloro-phenyl)-pyridine 271 mg (0.165 ml, 2.28 mmol) thionyl chloride were added drop by drop at 0° C. to a solution of 0.2 ml N,N-dimethylformamide (DMF) and 250 mg (1.14 mmol) [5-(3-Chloro-phenyl)-pyridin-3-yl]-methanol in 20 ml dichloromethane and stirred for 3 h at 0° C. The mixture was poured on ice/sodium bicarbonate solution and the organic phase separated. The water phase was extracted with dichloromethane. The combined organic phases were washed with water, dried (sodium sulphate), evaporated and the obtained material (248 mg, 84%) used without further purification.

MS: 238.0 (ESI+)

$^1$H-NMR (400 Hz, [D$_6$]DMSO): δ=4.88 (d, 2H, CH$_2$), 7.53 (m, 2H, Ar—Cl), 7.73 (d, 1H, Ar—Cl), 7.85 (s, 1H, Ar—Cl), 8.22 (s, 1H, pyridine), 8.68 (s, 1H, pyridine), 8.90 (s, 1H, pyridine)

Preparation of 3-(3-Chloro-phenyl)-5-[3-methyl-4-(4-[1,2,3]triazol-1-yl-butyl)-phenoxymethyl]-pyridine A solution of 97 mg (0.42 mmol) 3-methyl-4-(4-[1,2,3]triazol-1-yl-butyl)phenol in 4.0 ml N,N-dimethylformamide was treated at 0° C. with 17 mg (0.42 mmol) of 60% sodium hydride and stirred at 0° C. for 30 min. Then 100 mg (0.42 mmol) 3-Chloromethyl-5-(3-chloro-phenyl)-pyridine were added and stirred continued at r. t. over night. After addition of 8 ml water, the precipitate was isolated, washed thoroughly with water and n-heptane. The residue was dried at 40° C. to give 131 mg (71%) of the title compound as white powder.

MS: 433.3 (ESI+)

$^1$H-NMR (400 Hz, [D$_6$]DMSO): δ=1.42 (quintet, 2H, CH$_2$—CH$_2$—Ar), 1.85 (quintet, 2H, CH$_2$—CH$_2$-triazole), 2.20 (s, 3H, CH$_3$), 2.51 (t, 2H, CH$_2$—Ar), 4.40 (t, 2H, CH$_2$-triazole), 5.16 (s, 2H, OCH$_2$), 6.79 (d, 1H, OAr), 6.85 (s, 1H, OAr), 7.01 (d, 1H, OAr), 7.53 (dt, 2H, Ar—Cl), 7.71 (s, 1H, triazole), 7.72 (d, 1H, Ar—Cl), 7.84 (s, 1H, Ar—Cl), 8.11 (s, 1H, triazole), 8.19 (s, 1H, pyridine), 8.67 (s, 1H, pyridine), 8.89 (s, 1H, pyridine).

Example 42

6-(2-Fluoro-4-trifluoromethyl-phenyl)-2-methyl-3-[3-methyl-4-(4-[1,2,3]triazol-1-yl-butyl)-phenoxymethyl]-pyridine Preparation of 3-Chloromethyl-6-(2-fluoro-4-trifluoromethyl-phenyl)-2-methyl-pyridine i) 3-Dimethylamino-1-(2-fluoro-4-trifluoromethyl-phenyl)-propenone 10.0 g (48.5 mmol) (2-Fluoro-4-(trifluoromethyl)-acetophenone was solved under argon at room temperature in 17.34 g (19.3 ml, 0.146 mol) N,N-dimethylformamide dimethylacetal and stirred for 24 h at 100° C. The reaction mixture was evaporated. Chromatography on silica (eluent: ethyl acetate/n-heptane 2:1) gave 9.95 g (78%) of 3-Dimethylamino-1-(2-fluoro-4-trifluoromethyl-phenyl)-propenone.

MS: 262.1 (ESI+)

$^1$H-NMR (400 Hz, [D$_6$]DMSO): δ=2.87 (s, 3H, N—CH$_3$), 3.13 (s, 3H, N—CH$_3$), 5.42 (d, 1H, Ar—CO—CH), 7.61 (d, 1H, Ar—F—CF$_3$), 7.72 (m, 1H, CH—N(CH$_3$)$_2$), 7.72 (m, 2H, Ar—F—CF$_3$)

ii) 6-(2-Fluoro-4-trifluoromethyl-phenyl)-2-methyl-nicotinic acid methyl ester 7.40 g (7.2 ml, 56.87 mmol) 3-oxo-butyric acid ethyl ester and 3.80 g (49.27 mmol) ammonium acetate were given under argon to a solution of 9.90 g (37.90 mmol) 3-Dimethylamino-1-(2-fluoro-4-trifluoromethyl-phenyl)-propenone in 45 ml acetic acid and the reaction mixture was stirred for 6 h at 125° C. and then over night at room temperature. The reaction mixture was evaporated, the residue was taken up with ethyl acetate and washed twice with water. The water phase was extracted with ethyl acetate tree times. The combined organic were dried (sodium sulphate) and evaporated. The obtained material (11.25 g, 90%) used without further purification.

MS: 328.2 (ESI+)

$^1$H-NMR (400 Hz, [D$_6$]DMSO): δ=1.35 (t, 3H, O—CH$_2$—CH$_3$), 2.81 (s, 3H, pyridine-CH$_3$), 4.36 (q, 2H, O—CH$_2$—CH$_3$), 7.76 (d, 1H, Ar—F—CF$_3$), 7.86 (m, 1H, Ar—F—CF$_3$), 7.86 (m, 1H, pyridine), 8.22 (t, 1H, Ar—F—CF$_3$), 8.32 (d, 1H, pyridine iii) [6-(2-Fluoro-4-trifluoromethyl-phenyl)-2-methyl-pyridin-3-yl]-methanol 2.60 mg (68.44 mmol) lithium aluminium hydride were given to 110 ml tetrahydrofuran (THF) and stirred at room temperature (r. t.) for 20 min. A solution of 11.20 g (34.22 mmol) 6-(2-Fluoro-4-trifluoromethyl-phenyl)-2-methyl-nicotinic acid methyl ester in 110 ml THF was added drop by drop at 0° C. within 15 min., and the mixture stirred for 2 h at 0° C. 140 ml brine were added slowly at 0° C. and stirred continued for 1 h. The mixture was adjusted to pH=5 by slowly addition of conc. HCl. A formed salt precipitate was isolated by filtration and washed with THF. The combined THF-solutions were evaporated, the residue extracted twice with ethyl acetate, the organic phase dried (sodium sulphate) and evaporated. The obtained material (9.69 g, 99%) used without further purification.

MS: 286.1 (ESI+)

$^1$H-NMR (400 Hz, [D$_6$]DMSO): δ=2.51 (s, 3H, pyridine-CH$_3$), 4.59 (d, 2H, —CH$_2$), 4.59 (t, 1H, OH), 7.71 (d, 1H, Ar—F—CF$_3$), 7.71 (d, 1H, pyridine), 7.80 (d, 1H, Ar—F—CF$_3$), 7.87 (d, 1H, pyridine), 8.17 (t, 1H, Ar—F—CF$_3$)

iiii) 3-Chloromethyl-6-(2-fluoro-4-trifluoromethyl-phenyl)-2-methyl-pyridine 1.67 g (1.017 ml, 14.02 mmol) thionyl chloride were added drop by drop at 0° C. to a solution of 0.2 ml N,N-dimethyl-formamide (DMF) and 2.0 g (70.1 mmol) [6-(2-Fluoro-4-trifluoromethyl-phenyl)-2-methyl-pyridin-3-yl]-methanol in 115 ml dichloromethane and stirred for 3 h at 0° C. The mixture was poured on ice/sodium bicarbonate solution and the organic phase separated. The water phase is extracted with dichloromethane. The combined organic phases were washed with water, dried (sodium sulphate) and evaporated. Chromatography on silica (eluent: ethyl acetate/n-heptane 1:6) gave 1.79 g (83%) of 3-Chloromethyl-6-(2-fluoro-4-trifluoromethyl-phenyl)-2-methyl-pyridine.

MS: 304.15 (ESI+)

$^1$H-NMR (400 Hz, [D$_6$]DMSO): δ=2.66 (s, 3H, pyridine-CH$_3$), 4.92 (d, 2H, —CH$_2$), 7.73 (d, 1H, Ar—F—CF$_3$), 7.73 (d, 1H, pyridine), 7.83 (d, 1H, Ar—F—CF$_3$), 7.96 (d, 1H, pyridine), 8.17 (t, 1H, Ar—F—CF$_3$)

Preparation of 6-(2-Fluoro-4-trifluoromethyl-phenyl)-2-methyl-3-[3-methyl-4-(4-[1,2,3]triazol-1-yl-butyl)-phenoxymethyl]-pyridine A solution of 153 mg (0.66 mmol) 3-methyl-4-(4-[1,2,3]triazol-1-yl-butyl)phenol in 8.0 ml N,N-dimethylformamide was treated at 0° C. with 26 mg (0.66 mmol) of 60% sodium hydride and stirred at 0° C. for 30 min. Then 200 mg (0.66 mmol) 3-Chloromethyl-6-(2-fluoro-4-trifluoromethyl-phenyl)-2-methyl-pyridine were added and stirred continued at r. t. over night. After addition of 16 ml water, the precipitate was isolated, washed thoroughly with water and diisopropylether. The residue was dried at 40° C. to give 250 mg (76%) of the title compound as light brown powder.

MS: 499.43 (ESI+)

$^1$H-NMR (400 Hz, [D$_6$]DMSO): δ=1.44 (quintet, 2H, CH$_2$—CH$_2$—Ar), 1.87 (quintet, 2H, CH$_2$—CH$_2$-triazole), 2.22 (s, 3H, Ar—CH$_3$), 2.51 (t, 2H, CH$_2$—Ar), 2.60 (s, 3H, pyridine-CH$_3$), 4.42 (t, 2H, CH$_2$-triazole), 5.16 (s, 2H, OCH$_2$), 6.81 (d, 1H, OAr), 6.87 (s, 1H, OAr), 7.03 (d, 1H, OAr), 7.73 (s, 1H, triazole), 7.73 (d, 1H, Ar—F—CF$_3$), 7.73 (d, 1H, pyridine), 7.83 (d, 1H, Ar—F—CF$_3$), 7.93 (d, 1H, pyridine), 8.12 (s, 1H, triazole), 8.18 (t, 1H, Ar—F—CF$_3$)

Example 43

6-(2-Fluoro-4-trifluoromethyl-phenyl)-2-methyl-3-[4-(4-[1,2,3]triazol-1-yl-butyl)-phenoxymethyl]-pyridine A solution of 359 mg (1.65 mmol) 4-(4-[1,2,3]triazol-1-yl-butyl)phenol in 20.0 ml N,N-dimethylformamide was treated at 0° C. with 66 mg (1.65 mmol) of 60% sodium hydride and stirred at 0° C. for 30 min. Then 500 mg (1.65 mmol) 3-Chloromethyl-6-(2-fluoro-4-trifluoromethyl-phenyl)-2-methyl-pyridine were added and stirred continued at r. t. over night. After addition of 40 ml water, the precipitate was isolated, washed thoroughly with water and diisopropylether. The residue was dried at 40° C. to give 618 mg (77%) of the title compound as light brown powder.

MS: 485.40 (ESI+)

$^1$H-NMR (400 Hz, [D$_6$]DMSO): δ=1.49 (quintet, 2H, CH$_2$—CH$_2$—Ar), 1.82 (quintet, 2H, CH$_2$—CH$_2$-triazole), 2.54 (t, 2H, CH$_2$—Ar), 2.60 (s, 3H, pyridine-CH$_3$), 4.40 (t, 2H, CH$_2$-triazole), 5.18 (s, 2H, OCH$_2$), 6.99 (d, 2H, OAr), 7.12 (d, 2H, OAr), 7.70 (s, 1H, triazole), 7.73 (d, 1H, Ar—F—CF$_3$), 7.73 (d, 1H, pyridine), 7.82 (d, 1H, Ar—F—CF$_3$), 7.94 (d, 1H, pyridine), 8.11 (s, 1H, triazole), 8.19 (t, 1H, Ar—F—CF$_3$)

Unless stated to the contrary, all compounds in the examples were prepared and characterized as described. All ranges recited herein encompass all combinations and sub-combinations included within that range limit. All patents and publications cited herein are hereby incorporated by reference in their entirety for any purpose.

The invention claimed is:

1. A compound according to formula I,

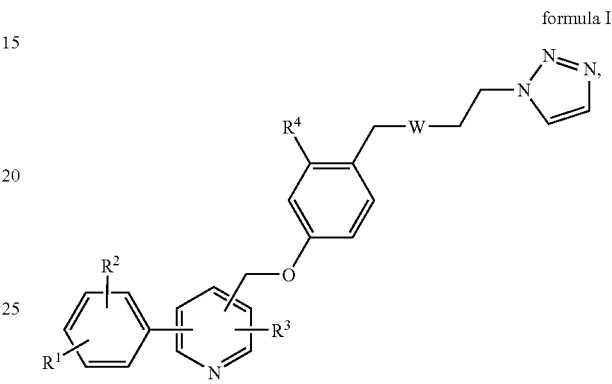

formula I wherein:
(a) R$^1$ is selected from the group consisting of: halogen, alkyl, alkoxy, halogenated alkyl and halogenated alkoxy;
(b) R$^2$ is hydrogen or halogen;
(c) R$^3$ is hydrogen or (C$_1$-C$_3$)alkyl;
(d) R$^4$ is hydrogen or (C$_1$-C$_3$)alkyl; and
(e) W is selected from the group consisting of: —CH$_2$—, —O—, —S—, —S(O)—, and —S(O)$_2$—;

or a pharmaceutically-acceptable salt thereof.

2. A compound according to claim 1, wherein:
(a) R$^1$ is selected from the group consisting of: halogen, halogenated alkyl, and halogenated alkoxy; and
(b) W is selected from the group consisting of: —CH$_2$—, —O—, —S—, and —S(O)—.

3. A compound according to claim 1 wherein said compound is a compound of formula I-a, formula I-a or a pharmaceutically-acceptable salt thereof.

4. A compound according to claim 1 wherein $R^1$ is selected from the group consisting of: halogen, halogenated alkyl and halogenated alkoxy.

5. A compound according claim 1 wherein W is —$CH_2$—.

6. A compound according to claim 1 wherein $R^2$ is hydrogen and W is —$CH_2$—.

7. A compound according to claim 1 wherein $R^2$ is hydrogen.

8. A compound according to claim 1, wherein $R^4$ is hydrogen.

9. A compound according to claim 1 wherein $R^4$ is ($C_1$-$C_3$) alkyl.

10. A compound according to claim 3, wherein:
(a) $R^1$ is halogen;
(b) $R^2$ is hydrogen; and
(c) W is —$CH_2$—.

11. A compound according to claim 1 selected from the group consisting of:
(a) 6-(4-Fluoro-phenyl)-2-methyl-3-[4-(4-[1,2,3]triazol-1-yl-butyl)-phenoxymethyl]-pyridine;
(b) 6-(4-Fluoro-phenyl)-2-methyl-3-[3-methyl-4-(4-[1,2,3]triazol-1-yl-butyl)-phenoxymethyl]-pyridine;
(c) 6-(4-Chloro-phenyl)-2-methyl-3-[4-(4-[1,2,3]triazol-1-yl-butyl)-phenoxymethyl]-pyridine;
(d) 6-(4-Chloro-phenyl)-2-methyl-3-[3-methyl-4-(4-[1,2,3]triazol-1-yl-butyl)-phenoxymethyl]-pyridine;
(e) 2-(4-Chloro-phenyl)-5-[4-(4-[1,2,3]triazol-1-yl-butyl)-phenoxymethyl]-pyridine; and
(f) 2-(4-Chloro-phenyl)-5-[3-methyl-4-(4-[1,2,3]triazol-1-yl-butyl)-phenoxymethyl]-pyridine.

12. A compound according to claim 3, wherein:
(a) $R^1$ is halogenated alkyl;
(b) $R^2$ is hydrogen; and
(c) W is —$CH_2$—.

13. A compound according to claim 1 selected from the group consisting of:
(a) 5-[4-(4-[1,2,3]Triazol-1-yl-butyl)-phenoxymethyl]-2-(4-trifluoromethyl-phenyl)-pyridine;
(b) 5-[3-Methyl-4-(4-[1,2,3]triazol-1-yl-butyl)-phenoxymethyl]-2-(4-trifluoromethyl-phenyl)-pyridine;
(c) 2-Methyl-3-[3-methyl-4-(4-[1,2,3]triazol-1-yl-butyl)-phenoxymethyl]-6-(4-trifluoromethyl-phenyl)-pyridine;
(d) 2-Methyl-3-[4-(4-[1,2,3]triazol-1-yl-butyl)-phenoxymethyl]-6-(4-trifluoromethyl-phenyl)-pyridine;
(e) 2-Methyl-3-[4-(4-[1,2,3]triazol-1-yl-butyl)-phenoxymethyl]-6-(3-trifluoromethyl-phenyl)-pyridine;
(f) 2-Methyl-3-[2-methyl-4-(4-[1,2,3]triazol-1-yl-butyl)-phenoxymethyl]-6-(3-trifluoromethyl-phenyl)-pyridine;
(g) 5-[4-(4-[1,2,3]Triazol-1-yl-butyl)-phenoxymethyl]-2-(3-trifluoromethyl-phenyl)-pyridine; and
(h) 5-[3-Methyl-4-(4-[1,2,3]triazol-1-yl-butyl)-phenoxymethyl]-2-(3-trifluoromethyl-phenyl)-pyridine.

14. A compound according to claim 3, wherein:
(a) $R^1$ is halogenated alkoxy;
(b) $R^2$ is hydrogen; and
(c) W is —$CH_2$—.

15. A compound according to claim 1 selected from the group consisting of:
(a) 5-[3-Methyl-4-(4-[1,2,3]triazol-1-yl-butyl)-phenoxymethyl]-2-(4-trifluoromethoxy-phenyl)-pyridine;
(b) 2-Methyl-3-[4-(4-[1,2,3]triazol-1-yl-butyl)-phenoxymethyl]-6-(4-trifluoromethoxy-phenyl)-pyridine;
(c) 2-Methyl-3-[3-methyl-4-(4-[1,2,3]triazol-1-yl-butyl)-phenoxymethyl]-6-(4-trifluoromethoxy-phenyl)-pyridine;
(d) 2-Methyl-3-[4-(4-[1,2,3]triazol-1-yl-butyl)-phenoxymethyl]-6-(3-trifluoromethoxy-phenyl)-pyridine; and
(e) 2-Methyl-3-[2-methyl-4-(4-[1,2,3]triazol-1-yl-butyl)-phenoxymethyl]-6-(3-trifluoromethoxy-phenyl)-pyridine.

16. A compound according to claim 3, wherein:
(a) $R^1$ is halogenated alkyl;
(b) $R^2$ is fluorine; and
(c) W is —$CH_2$—.

17. A compound according to claim 1 selected from the group consisting of:
(a) 6-(2-Fluoro-4-trifluoromethyl-phenyl)-2-methyl-3-[3-methyl-4-(4-[1,2,3]triazol-1-yl-butyl)-phenoxymethyl]-pyridine; and
(b) 6-(2-Fluoro-4-trifluoromethyl-phenyl)-2-methyl-3-[4-(4-[1,2,3]triazol-1-yl-butyl)-phenoxymethyl]-pyridine.

18. A compound according to claim 3, wherein W is —O—.

19. A compound according to claim 1 wherein the compound is:
2-Methyl-3-[4-(2-[1,2,3]triazol-1-yl-ethoxymethyl)-phenoxymethyl]-6-(4-trifluoromethyl-phenyl)-pyridine.

20. A compound according to claim 3, wherein W is —S(O)—.

21. A compound according to claim 1 wherein the compound is:
2-Methyl-3-[4-(2-[1,2,3]triazol-1-yl-ethanesulfinylmethyl)-phenoxymethyl]-6-(4-trifluoromethyl-phenyl)-pyridine.

22. A compound according to claim 3, wherein:
(a) $R^1$ is halogen or halogenated alkyl;
(b) $R^2$ is hydrogen; and
(c) W is —S—.

23. A compound according to claim 1 selected from the group consisting of:
(a) 2-Methyl-3-[4-(2-[1,2,3]triazol-1-yl-ethylsulfanylmethyl)-phenoxymethyl]-6-(4-trifluoromethyl-phenyl)-pyridine;
(b) 6-(4-Fluoro-phenyl)-2-methyl-3-[4-(2-[1, 2, 3]triazol-1-yl-ethylsulfanylmethyl)-phenoxymethyl]-pyridine;
(c) 6-(4-Chloro-phenyl)-2-methyl-3-[4-(2-[1,2,3]triazol-1-yl-ethylsulfanylmethyl)-phenoxymethyl]-pyridine; and
(d) 2-(4-Chloro-phenyl)-5-[4-(2-[1,2,3]triazol-1-yl-ethylsulfanylmethyl)-phenoxymethyl]-pyridine.

24. A compound according to claim 3, wherein:
(a) $R^1$ is selected from the group consisting of: halogen, halogenated alkyl, and halogenated alkoxy; and, with respect to the phenyl group to which $R^1$ is attached, $R^1$ is attached at the para position relative to the bond at which said phenyl group is attached to the adjacent pyridyl group;
(b) $R^2$ is hydrogen;
(c) $R^4$ is ($C_1$-$C_3$)alkyl; and
(d) W is —$CH_2$—.

25. A compound according to claim 3, wherein:
(a) $R^1$ is chlorine or halogenated alkyl; and, with respect to the phenyl group to which $R^1$ is attached, $R^1$ is attached at the para position relative to the bond at which said phenyl group is attached to the adjacent pyridyl group
(b) $R^2$ is hydrogen; and
(c) W is —$CH_2$—, —O— or —S—.

26. A compound according to claim 3, wherein:
(a) $R^1$ is chlorine or halogenated alkyl; and, with respect to the phenyl group to which $R^1$ is attached, $R^1$ is attached at the para position relative to the bond at which said phenyl group is attached to the adjacent pyridyl group
(b) $R^2$ is hydrogen; and
(c) W is —$CH_2$—.

27. A compound according to claim 1 wherein said compound is a compound

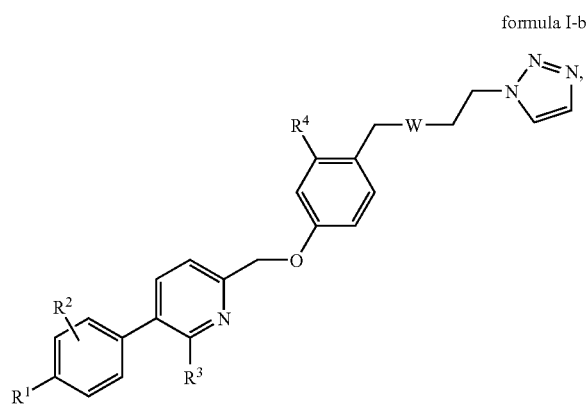

formula I-b or a pharmaceutically-acceptable salt thereof.

28. A compound according to claim 27, wherein:
(a) $R^1$ is halogenated alkyl;
(b) $R^2$ is hydrogen; and
(c) W is —CH$_2$—.

29. A compound according to claim 1, selected from the group consisting of:
(a) 2-[4-(4-[1,2,3]Triazol-1-yl-butyl)-phenoxymethyl]-5-(4-trifluoromethyl-phenyl)-pyridine; and
(b) 2-[3-Methyl-4-(4-[1,2,3]triazol-1-yl-butyl)-phenoxymethyl]-5-(4-trifluoromethyl-phenyl)-pyridine.

30. A compound according to claim 1 wherein said compound is a compound of formula I-d

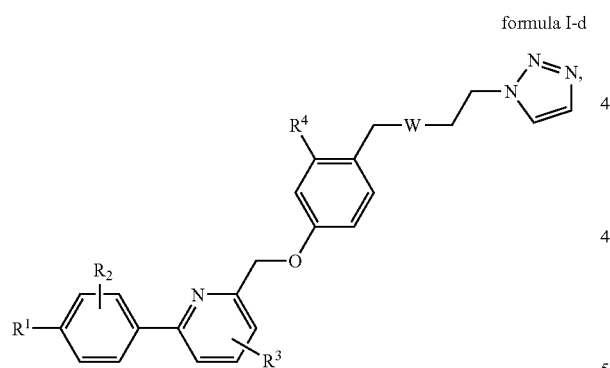

formula I-d or a pharmaceutically-acceptable salt thereof.

31. A compound according to claim 30, wherein:
(a) $R^1$ is selected from the group consisting of: halogen, halogenated alkyl, and halogenated alkoxy;
(b) $R^2$ is hydrogen;
(c) $R^3$ is hydrogen; and
(d) W is —CH$_2$—.

32. A compound according to claim 1 selected from the group consisting of:
(a) 2-[4-(4-[1,2,3]Triazol-1-yl-butyl)-phenoxymethyl]-6-(4-trifluoromethyl-phenyl)-pyridine;
(b) 2-[3-Methyl-4-(4-[1,2,3]triazol-1-yl-butyl)-phenoxymethyl]-6-(4-trifluoromethyl-phenyl)-pyridine;
(c) 2-[3-Methyl-4-(4-[1,2,3]triazol-1-yl-butyl)-phenoxymethyl]-6-(4-trifluoromethoxy-phenyl)-pyridine (d) 3-[4-(4-[1, 2, 3]Triazol-1-yl-butyl)-phenoxymethyl]-5-(4-trifluoromethyl-phenyl)-pyridine;
(e) 2-(4-Chloro-phenyl)-6-[3-methyl-4-(4-[1,2,3]triazol-1-yl-butyl)-phenoxymethyl]-pyridine;
(f) 2-(4-Chloro-phenyl)-6-[4-(4-[1,2,3]triazol-1-yl-butyl)-phenoxymethyl]-pyridine; and
(g) 2-(3-Chloro-phenyl)-6-[3-methyl-4-(4-[1,2,3]triazol-1-yl-butyl)-phenoxymethyl]-pyridine.

33. A compound according to claim 1 wherein said compound is a compound of formula I-e

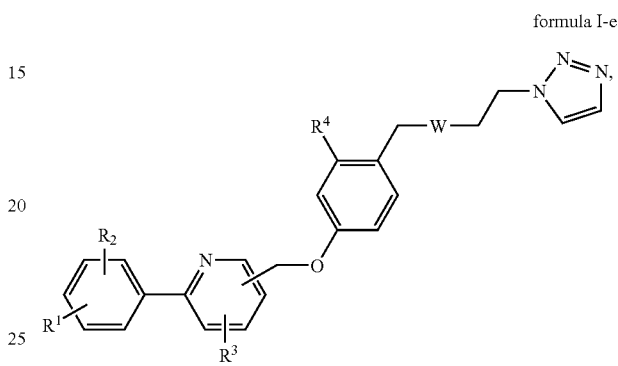

formula I-e or a Pharmaceutically-acceptable salt thereof.

34. A compound according to claim 33, wherein:
(a) $R^1$ is selected from the group consisting of: halogen, halogenated alkyl, and halogenated alkoxy; and
(b) W is selected from the group consisting of: —CH$_2$—, —O—, —S—, and —S(O)—.

35. A compound according to claim 1 wherein said compound is a compound of formula I-f

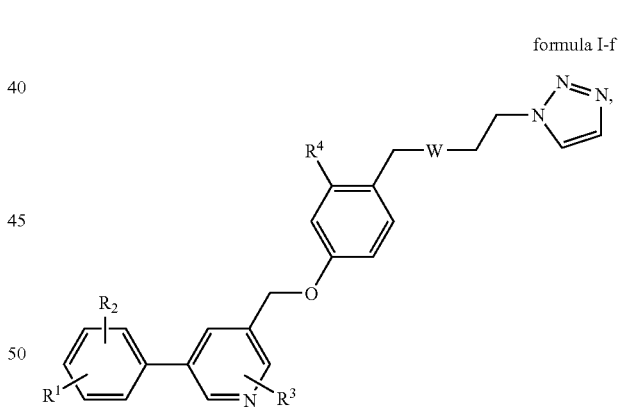

formula I-f or a pharmaceutically-acceptable salt thereof.

36. A compound according to claim 35, wherein:
(a) $R^1$ is halogen, halogenated alkyl or halogenated alkoxy;
(b) $R^2$ and $R^3$ are both hydrogen; and
(c) W is —CH$_2$—.

37. A compound according to claim 1 selected from the group consisting of:
(a) 2-[4-(4-[1,2,3]Triazol-1-yl-butyl)-phenoxymethyl]-6-(4-trifluoromethoxy-phenyl)-pyridine;
(b) 3-[3-Methyl-4-(4-[1,2,3]triazol-1-yl-butyl)-phenoxymethyl]-5-(4-trifluoromethyl-phenyl)-pyridine;
(c) 3-[3-Methyl-4-(4-[1,2,3]triazol-1-yl-butyl)-phenoxymethyl]-5-(4-trifluoromethoxy-phenyl)-pyridine;

(d) 3-[4-(4-[1,2,3]Triazol-1-yl-butyl)-phenoxymethyl]-5-(4-trifluoromethoxy-phenyl)-pyridine;

(e) 3-(4-Chloro-phenyl)-5-[3-methyl-4-(4-[1, 2, 3]triazol-1-yl-butyl)-phenoxymethyl]-pyridine;

(f) 3-(4-Chloro-phenyl)-5-[4-(4-[1,2,3]triazol-1-yl-butyl)-phenoxymethyl]-pyridine; and (g) 3-(3-Chloro-phenyl)-5-[3-methyl-4-(4-[1,2,3]triazol-1-yl-butyl)-phenoxymethyl]-pyridine.

38. A pharmaceutical composition comprising a therapeutically effective amount of a compound of claim 1 and a pharmaceutically acceptable carrier.

* * * * *